United States Patent
Chan et al.

(10) Patent No.: US 12,353,030 B2
(45) Date of Patent: Jul. 8, 2025

(54) OPTICAL COHERENT IMAGER HAVING SHARED INPUT-OUTPUT PATH AND METHOD FOR SENSING COHERENT LIGHT

(71) Applicant: OAM Photonics LLC, San Diego, CA (US)

(72) Inventors: Kam Wai Clifford Chan, San Diego, CA (US); Chung Ki Wong, San Diego, CA (US)

(73) Assignee: OAM Photonics LLC, Albuquerque, NM (US)

( * ) Notice: Subject to any disclaimer, the term of this patent is extended or adjusted under 35 U.S.C. 154(b) by 0 days.

(21) Appl. No.: 17/622,629

(22) PCT Filed: Jul. 21, 2021

(86) PCT No.: PCT/US2021/042533
§ 371 (c)(1),
(2) Date: Dec. 23, 2021

(87) PCT Pub. No.: WO2023/003550
PCT Pub. Date: Jan. 26, 2023

(65) Prior Publication Data
US 2024/0142705 A1    May 2, 2024

Related U.S. Application Data

(60) Provisional application No. 63/147,733, filed on Feb. 9, 2021.

(51) Int. Cl.
*G02B 6/42* (2006.01)
*G01S 7/499* (2006.01)
(Continued)

(52) U.S. Cl.
CPC ........... *G02B 6/4213* (2013.01); *G01S 7/499* (2013.01); *G01S 17/34* (2020.01); *G02B 6/2706* (2013.01);
(Continued)

(58) Field of Classification Search
CPC ...... G02B 6/27–2793; G02B 6/28–287; G02B 2006/2839; G02B 2006/2865;
(Continued)

(56) References Cited

U.S. PATENT DOCUMENTS

| | | | |
|---|---|---|---|
| 5,204,866 A * | 4/1993 | Block | H04B 10/803 398/118 |
| 6,900,899 B2 * | 5/2005 | Nevis | G02B 27/283 356/487 |

(Continued)

FOREIGN PATENT DOCUMENTS

WO    2020205450 A1    10/2020

OTHER PUBLICATIONS

Kersey, A.D.; Marrone, M.J.; Dandridge, A.,"Adaptive polarisation diversity receiver configuration for coherent optical fibre communications," Elec. Lett., 25, 275-277 (1989). (Year: 1989).*
(Continued)

*Primary Examiner* — Daniel Petkovsek
*Assistant Examiner* — Emma R. Oxford
(74) *Attorney, Agent, or Firm* — Hsuanyeh Law Group, PC

(57) ABSTRACT

The present disclosure provides an optical coherent imager implemented on a photonic integrated circuit (PIC) that enables shared path for transmitting and receiving optical signals by exploiting polarization diversity. The present disclosure also provides an optical coherent imager including an array of the optical coherent sensing units to simplify
(Continued)

the design and calibrations of the imager, and a method for coherent sensing by the optical coherent imager.

24 Claims, 23 Drawing Sheets

(51) Int. Cl.
    *G01S 17/34*     (2020.01)
    *G02B 6/27*     (2006.01)
    *G02B 6/34*     (2006.01)

(52) U.S. Cl.
    CPC ............ *G02B 6/274* (2013.01); *G02B 6/2773* (2013.01); *G02B 6/34* (2013.01)

(58) Field of Classification Search
    CPC .................. G02B 27/28; G02B 27/283; G01S 7/481–4818; G01S 17/32; G01S 17/34
    See application file for complete search history.

(56) References Cited

U.S. PATENT DOCUMENTS

| | | | |
|---|---|---|---|
| 7,006,732 B2* | 2/2006 | Gunn, III | G02B 6/1228 385/37 |
| 10,151,883 B2* | 12/2018 | Bauters | G02B 6/2706 |
| 10,401,480 B1* | 9/2019 | Gaalema | G01S 17/931 |
| 10,908,372 B2 | 2/2021 | Moebius et al. | |
| 10,948,598 B1 | 3/2021 | Prabhakar et al. | |
| 11,402,802 B2* | 8/2022 | Chan | G03H 1/2645 |
| 12,015,440 B2* | 6/2024 | Chan | H04B 10/61 |
| 2003/0016425 A1 | 1/2003 | Tan et al. | |
| 2003/0058499 A1* | 3/2003 | Reingand | H04B 10/2563 398/98 |
| 2007/0297054 A1* | 12/2007 | Yao | G02B 27/286 359/484.04 |
| 2017/0155225 A1* | 6/2017 | Villeneuve | H01S 3/06754 |
| 2019/0064457 A1* | 2/2019 | Roth | G02B 6/4206 |
| 2020/0150241 A1 | 5/2020 | Byrnes et al. | |
| 2020/0186258 A1 | 6/2020 | Brown et al. | |
| 2020/0256958 A1 | 8/2020 | Piggott | |
| 2020/0319314 A1 | 10/2020 | Behzadi et al. | |
| 2021/0055390 A1* | 2/2021 | LaChapelle | G01S 7/4865 |
| 2021/0055694 A1 | 2/2021 | Chan et al. | |
| 2021/0316756 A1 | 10/2021 | Davydenko | |
| 2022/0146645 A1* | 5/2022 | Michaels | G02B 5/1866 |
| 2022/0390578 A1* | 12/2022 | Chan | G01S 17/32 |
| 2023/0152537 A1* | 5/2023 | Witzens | G02B 6/34 385/33 |
| 2024/0085538 A1* | 3/2024 | Grudinin | G01S 7/4911 |

OTHER PUBLICATIONS

Xia Chen and Hon K. Tsang, "Polarization-independent grating couplers for silicon-on-insulator nanophotonic waveguides," Opt. Lett. 36, 796-798 (2011). (Year: 2011).*

B. Shen, P. Wang, R. Polson, and R. Menon, "Integrated metamaterials for efficient and compact free-space-to-waveguide coupling," Opt. Express 22, 27175-27182 (2014). (Year: 2014).*

Zhao, J., Zhang, L., Li, J. et al. A Wide-angle Multi-Octave Broadband Waveplate Based on Field Transformation Approach. Sci. Rep. 5, 17532 (2015). (Year: 2015).*

Paolo Pintus, Duanni Huang, Paul Adrian Morton, Yuya Shoji, Tetsuya Mizumoto, and John E. Bowers, "Broadband TE Optical Isolators and Circulators in Silicon Photonics Through Ce:YIG Bonding," J. Lightwave Technol. 37, 1463-1473 (2019). (Year: 2019).*

International Search Report and Written Opinion dated Oct. 19, 2021 in counterpart PCT application (12 pages).

* cited by examiner

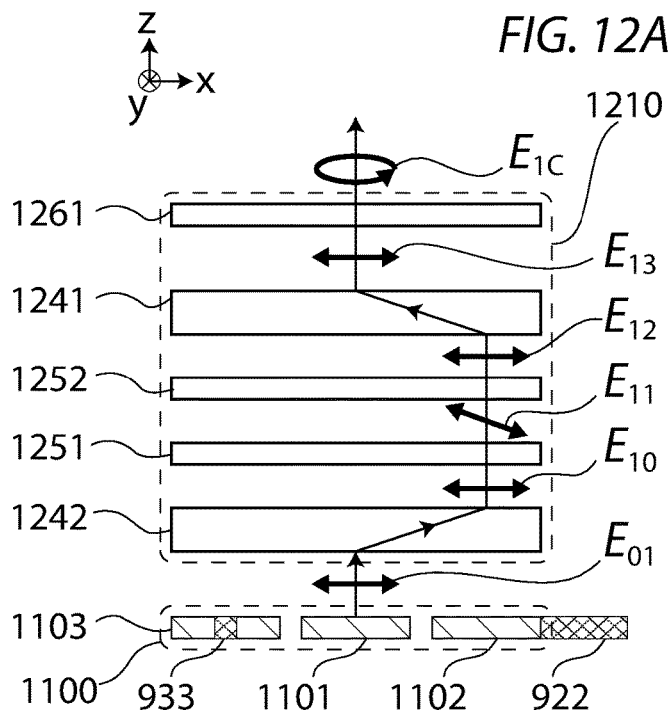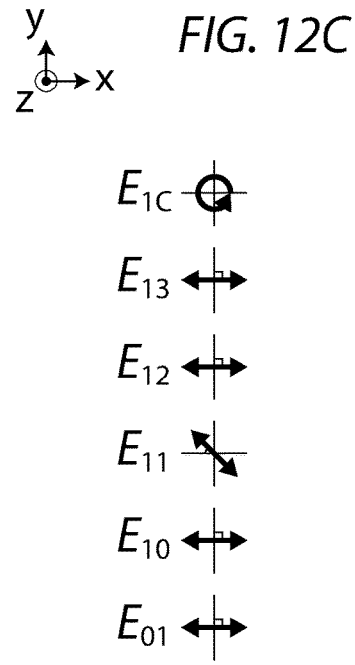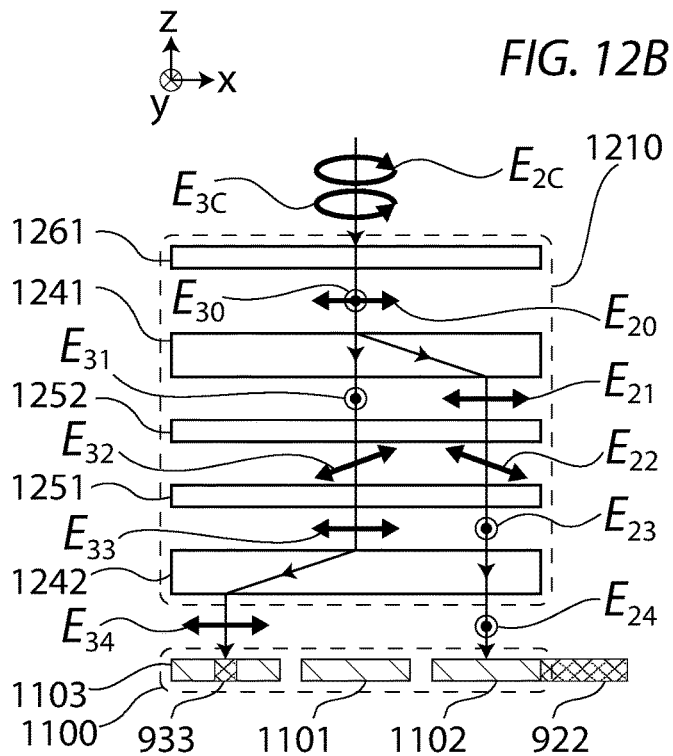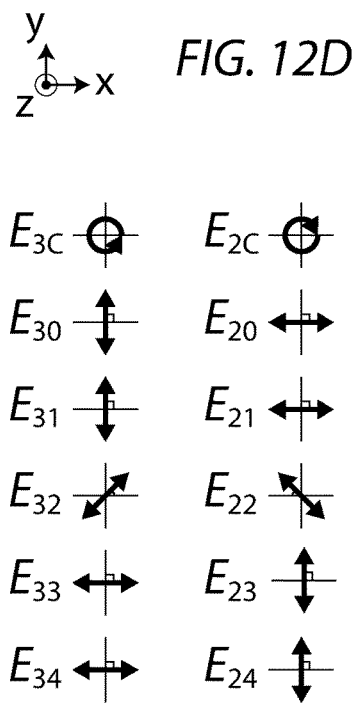

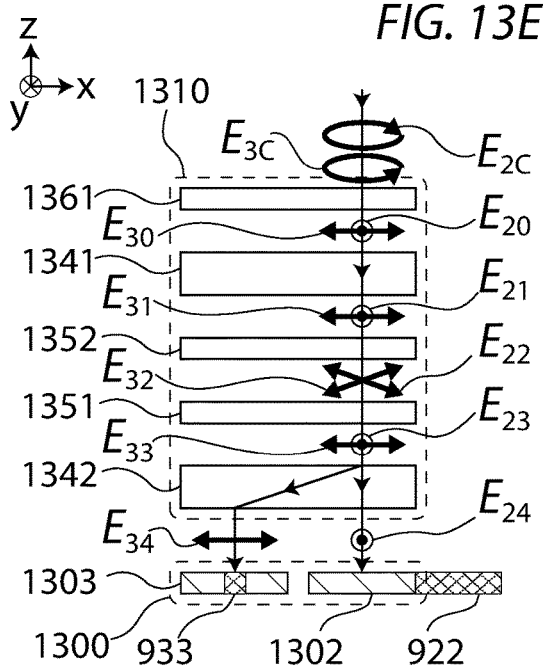
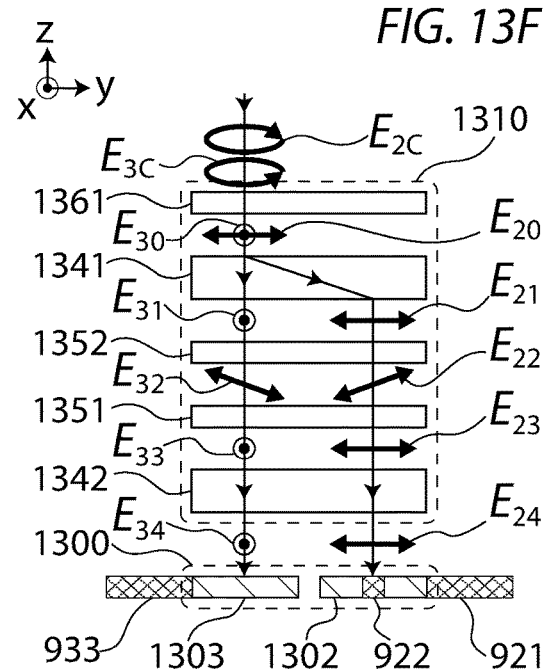
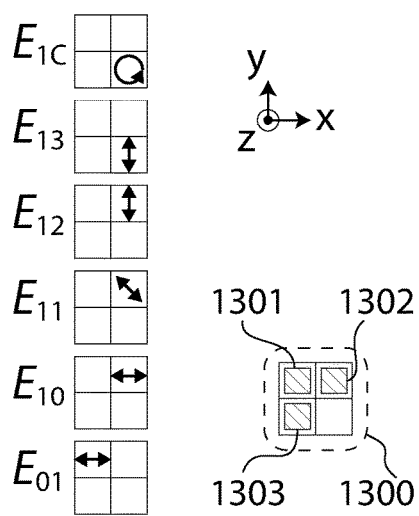
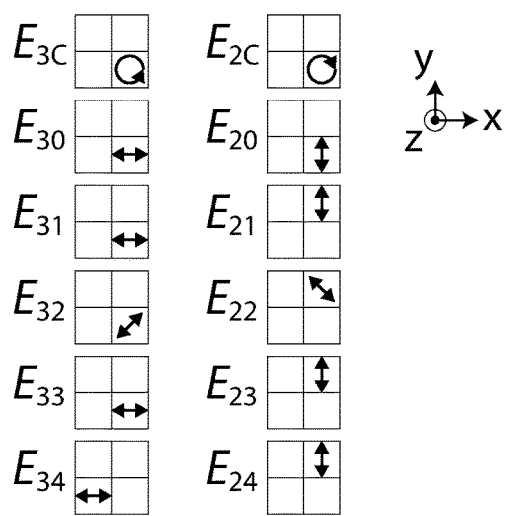

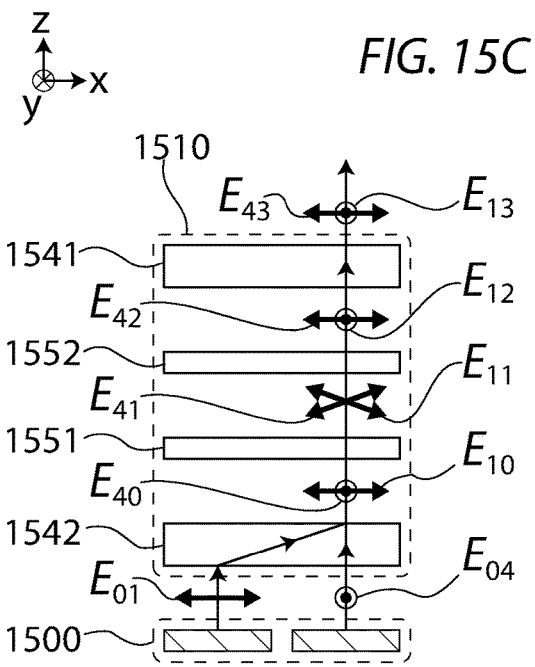
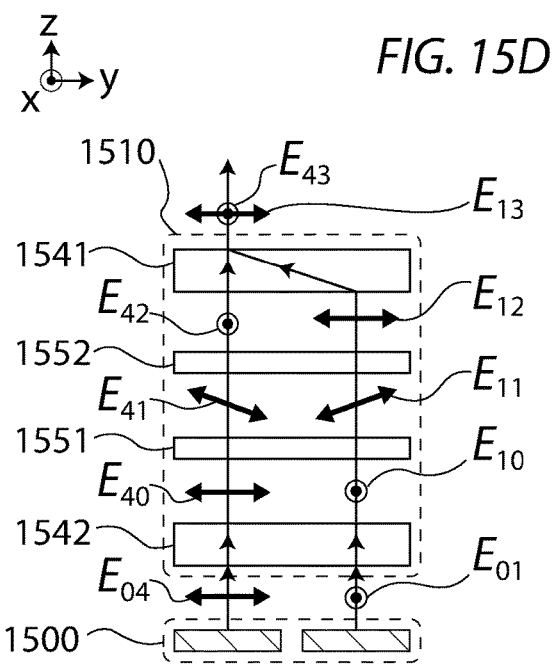
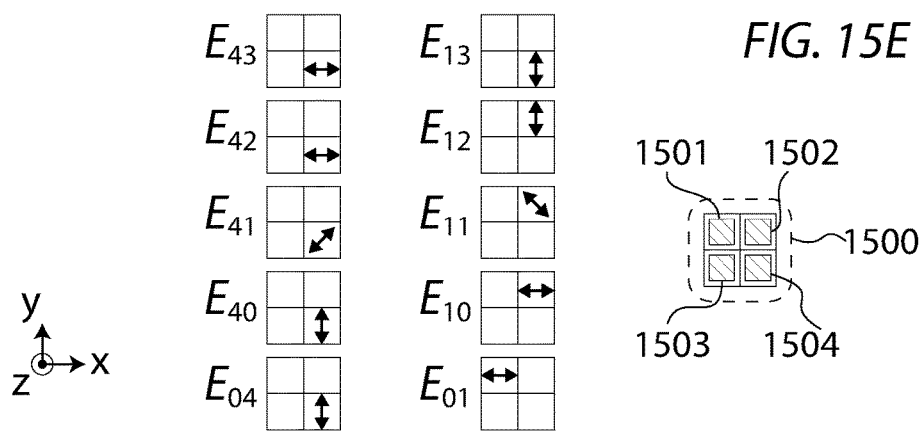

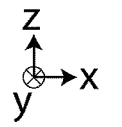
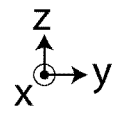
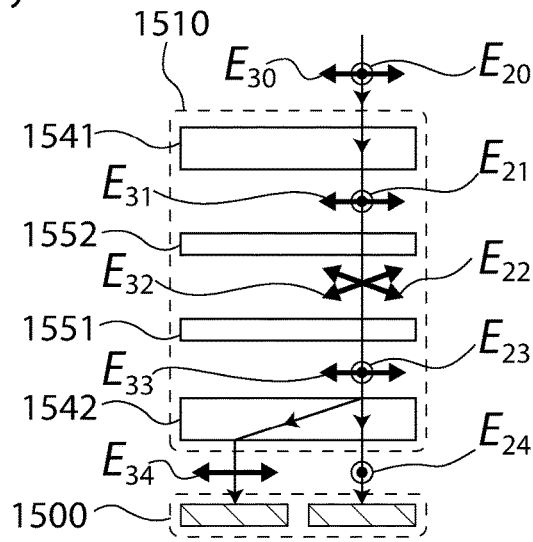
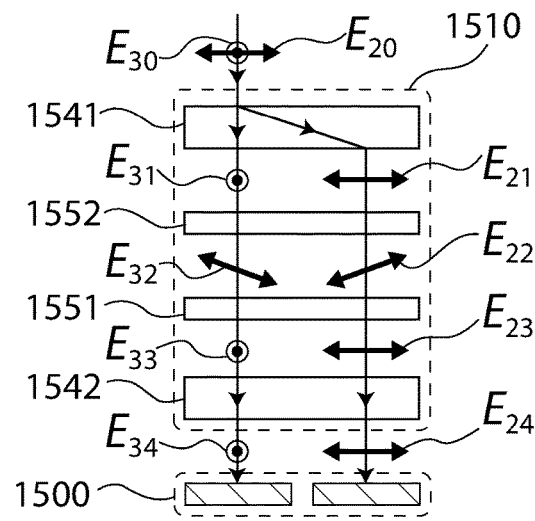
FIG. 15F
FIG. 15G
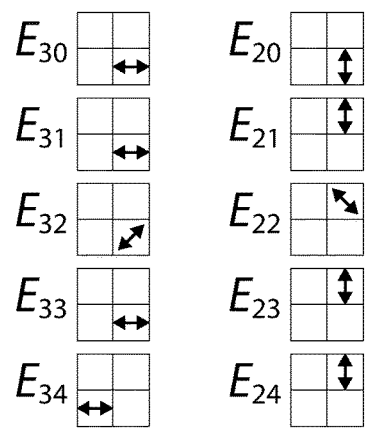
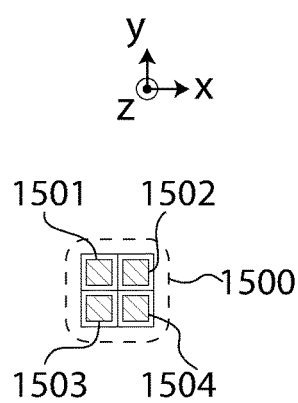
FIG. 15H

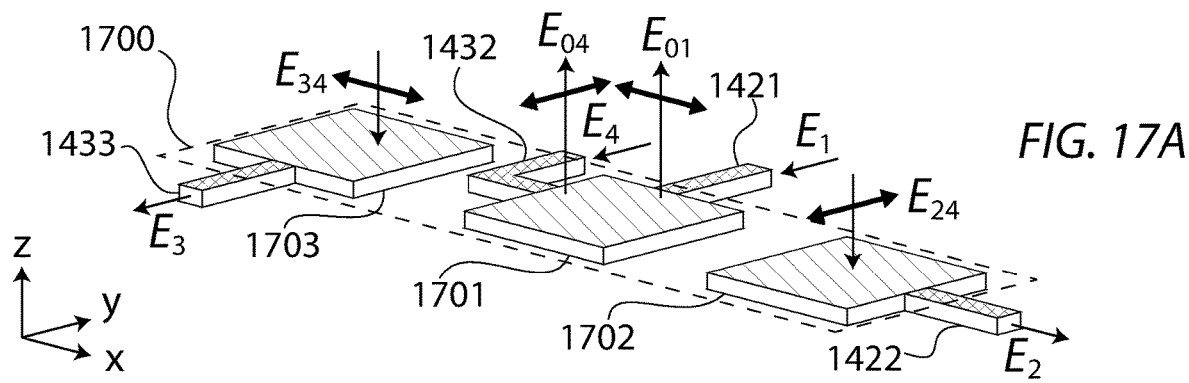
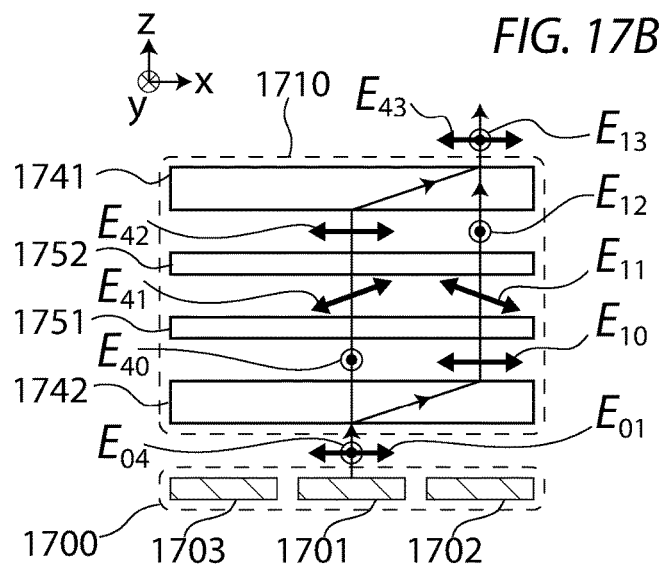
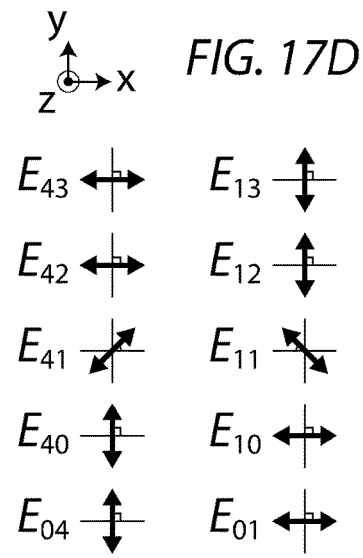
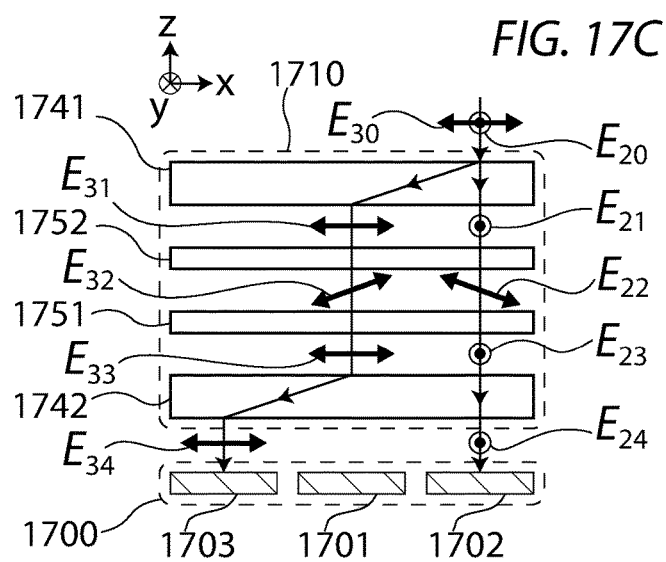
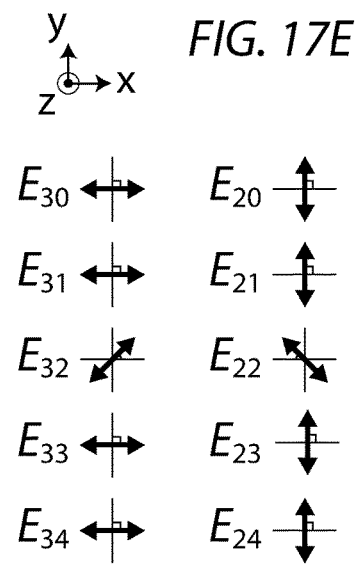

OPTICAL COHERENT IMAGER HAVING SHARED INPUT-OUTPUT PATH AND METHOD FOR SENSING COHERENT LIGHT

RELATED APPLICATION

This application is a national stage of International Application No. PCT/US21/42533, filed on Jul. 21, 2021, which claims the benefit of priority to U.S. Provisional Application No. 63/147,733, filed Feb. 9, 2021, the entire contents of which are incorporated herein by reference for all purposes.

STATEMENT REGARDING FEDERALLY SPONSORED RESEARCH OR DEVELOPMENT

This invention was made with Government support under Grant Number 2015160 awarded by the National Science Foundation. The Government has certain rights to this invention.

TECHNICAL FIELD

The present disclosure relates to an optical coherent imager having a shared input-output path and a method for sensing coherent light. More particularly, the present disclosure relates to a photonic integrated circuit having shared input-output path based on polarization diversity and a method for sensing coherent light.

BACKGROUND

An optical coherent imager is an active imaging system that comprises an array of optical detectors (herein referred to as a "sensor") and a light source (usually a coherent light source such as a laser). The light source serves the purposes of target illumination as well as providing a local oscillator (LO) for optical coherent detection (also called optical heterodyne detection). Such an optical coherent imager may be used in applications including 3D frequency-modulated continuous-wave (FMCW) LIDAR and optical coherence tomography (OCT). The illuminating light that is reflected (or scattered) by the target and received by the imager is hereby called the received optical target signal, or simply the target signal.

Conventionally, to perform optical coherent detection, the optical coherent imager operates by coherently combining the LO with the target signal in free-space using bulk optics before performing detection by the sensor of the imager. In contrast, an optical coherent imager with a detection sensor based on the photonic integrated circuit (PIC) technology permits the mixing of the LO and the target signal on a photonic chip (also called a PIC chip in this disclosure). More specifically, the PIC-based sensor comprises an array of coherent sensing units that plays the role of the active detection pixels of a conventional detection array such as a CCD or CMOS image sensor. Instead of performing photo-detection directly at the pixels as in a conventional detection array, the coherent sensing units of the PIC-based sensor couple the target signals from free space through free-space-to-waveguide couplers into a plurality of waveguides on the PIC chip. The target signals manifested as waveguide modes in the waveguides may then be manipulated and processed using the various photonic components that are implemented on the PIC chip, including the coherent mixing with the LO using 2×2 optical couplers and the detection by photodetectors. Here the LO may manifest as a waveguide mode by introducing the LO light into the PIC chip through couplers. With the recent developments of monolithic and heterogeneous integrations of lasers on a PIC chip, the light source may even be integrated on the same PIC chip of the PIC-based sensor.

For target illumination, two approaches are commonly used in active imagers: (1) full-field illumination and (2) finite-field illumination with a scanning beam.

For full-field illumination, the target scene is flooded with the illuminating light, so that the entire instantaneous field-of-view (FOV) of the sensor receives optical signals reflected or scattered from the scene. Advantages of the full-field approach include high frame rate and simplified output format for data post-processing, as it enables the sensor to acquire an image like an ordinary camera. A significant disadvantage of the full-field approach is that the illuminating laser power is spread over a large area, resulting in fewer photons reflected or scattered back to each sensing unit of the imager sensor. Consequently, the full-field approach demands the imager sensor to have higher sensitivity, which usually requires the use of exotic and expensive materials for the fabrication of the sensors. The full-field approach may also limit the active imager to operate in distances constrained by a maximal illuminating laser power due to practical factors such as eye safety.

For finite-field illumination with a scanning beam, the target scene is scanned by an illuminating laser beam by steering the laser beam using some scanning mechanism. At each scanning position, only a finite FOV of the imager sensor receives target signals. This finite FOV depends on the spot size of the illuminating laser beam and the imaging optics of the imager. Due to a smaller FOV used in the finite-field illumination approach, the laser power is concentrated in a smaller region, resulting in more photons received by the imager sensor at the corresponding FOV. Consequently, the finite-field illumination approach usually allows the active imager to operate in longer distances than the full-field illumination approach given the same illuminating laser power.

For an optical coherent imager utilizing a PIC-base sensor and operating with the finite-field illumination approach, the beam scanning mechanism may be implemented on the same PIC chip of the sensor to lower the manufacturing cost of the imager. Common beam scanning mechanisms implementable on a PIC chip include an optical phased array (OPA). The photonic components for the beam scanning mechanism (herein referred to as a "transmitter") nevertheless are usually implemented in a region of the PIC chip that is separate from the detection region comprising the free-space-to-waveguide couplers (herein referred to as a "receiver") of the PIC-based sensor. Due to such separation, separate optical systems may be needed for the transmitter and receiver, in order to respectively direct the illuminating light beam to the target and to maximize the coupling of the target signal to the receiver.

In an optical coherent imager utilizing finite-field illumination, it may be desirable that the transmitter and receiver share the same optical system for, respectively, illuminating the target and receiving target signals. Even more desirably, the optical paths of the outgoing probe beam and the incoming target signals are the same. Advantages of such an input-output-path-sharing imager include a simplified optical system and simplified calibrations between the transmitter and receiver. The simplified optical system may lead to a more efficient use of laser power by enabling the imager to supply the LO light more specifically only to those coherent sensing units that receive signals from the target during the beam scanning process.

REFERENCES

1. Lawrence C. Gunn, III, Thierry J. Pinguet, Maxime J. Rattier, and Jeremy Witzens, "POLARIZATION SPLITTING GRATING COUPLERS," U.S. Pat. No. 7,006,732 B2, filed Dec. 12, 2003.
2. Bing Shen, Peng Wang, Randy Polson, and Rajesh Menon, "Integrated metamaterials for efficient and compact free-sp ace-to-waveguide coupling," Optics Express, Vol. 22, pp. 27175-27182 (2014).
3. Xia Chen and Hon K. Tsang, "Polarization-independent grating couplers for silicon-on-insulator nanophotonic waveguides," Optics Letters, Vol. 36, No. 6, pp. 796-798 (2011).
4. Junming Zhao, Lianhong Zhang, Jensen Li, Yijun Feng, Any Dyke, Sajad Haq, and Yang Hao, "A Wide-angle Multi-Octave Broadband Waveplate Based on Field Transformation Approach," Scientific Reports, 5, 17532 (2015).
5. Paolo Pintus, Duanni Huang, Paul Adrian Morton, Yuya Shoji, Tetsuya Mizumoto, John E. Bowers, "Broadband TE Optical Isolators and Circulators in Silicon Photonics Through Ce:YIG Bonding," Journal of Lightwave Technology, Vol. 37, No. 5, p. 1463 (2019).

SUMMARY

The present disclosure provides an optical coherent imager implemented on a photonic integrated circuit (PIC) that enables shared path for transmitting and receiving optical signals by exploiting polarization diversity. The present disclosure also provides an optical coherent imager including an array of the optical coherent sensing units to simplify the design and calibrations of the imager, and a method for coherent sensing by the optical coherent imager.

In one aspect, the present disclosure provides an optical coherent sensor comprising a plurality of coherent sensing units and a polarization transformer disposed on the coherent sensing units. Each of the coherent sensing units comprises: a polarization diversified optical coupler capable of directing optical signals having a first polarization state to and from free space and a first waveguide and capable of directing optical signals having a second polarization state to and from free space and a second waveguide; one or more 2×2 optical couplers optically coupled to the polarization diversified optical coupler through at least one of the first and second waveguides; and one or more photodetectors optically coupled to the 2×2 optical couplers.

In one embodiment, the polarization diversified optical coupler comprises a first sub-coupler and a second sub-coupler.

In one embodiment, one of the first and second sub-couplers is polarization dependent which optimally couples with optical signals of a predefined polarization state, and wherein the other one of the first and second sub-couplers is polarization independent which optimally couples with optical signals of any polarization states.

In one embodiment, the second sub-coupler is disposed on and vertically separated from the first sub-coupler.

In one embodiment, the first and second sub-couplers are disposed on a photonic substrate and laterally separated from each other.

In one embodiment, the polarization transformer directs an outgoing optical signal from one of the first and second sub-couplers to an optical path in free space, and separates an incoming optical signal from the optical path into a first optical signal having the first polarization state and a second optical signal having the second polarization state, either one or both of the first and second optical signals being spatially displaced by the polarization transformer such that the first and second optical signals are incident respectively on the first and second sub-couplers.

In one embodiment, the polarization transformer comprises at least one polarization-dependent beam-separator.

In one embodiment, the polarization transformer comprises one or more polarization convertors that rotate a linearly polarized optical signal by a predefined angle.

In one embodiment, at least one of the polarization convertors is a Faraday rotator.

In one embodiment, the polarization transformer comprises one or more quarter-wave plates.

In one embodiment, the polarization diversified optical coupler further comprises a third sub-coupler. In one embodiment, the first, second, and third sub-couplers are disposed on a photonic substrate and laterally separated from each other.

In one embodiment, the polarization transformer directs an outgoing optical signal from one of the first, second, and third sub-couplers to an optical path in free space, and separates an incoming optical signal from the optical path into a first optical signal having the first polarization state and a second optical signal having the second polarization state, either one or both of the first and second optical signals being spatially displaced by the polarization transformer such that the first and second optical signals are incident respectively on two of the first, second, and third sub-couplers.

In one embodiment, the polarization diversified optical coupler further comprises a fourth sub-coupler.

In one embodiment, the polarization transformer directs an outgoing optical signal from two of the first, second, third, and fourth sub-couplers to an optical path in free space, and separates an incoming optical signal from the optical path into a first optical signal having the first polarization state and a second optical signal having the second polarization state, either one or both of the first and second optical signals being spatially displaced by the polarization transformer such that the first and second optical signals are incident respectively on two of the first, second, third, and fourth sub-couplers.

In another aspect, the present disclosure provides an optical coherent imager comprising an optical coherent sensor described above and an imaging optics system including a plurality of lenses, wherein the imaging optics system is disposed such that the optical coherent sensor is located proximate an image plane of the imaging optics system.

In still another aspect, the present disclosure provides a method for optical coherent imaging, comprising: emitting, from an optical coherent imager, one or more outgoing optical signals to one or more targets respectively along one or more optical paths corresponding respectively to one or more field-of-view positions of the optical coherent imager; receiving, by the optical coherent imager along the optical paths, one or more incoming optical signals reflected from the targets illuminated by the outgoing optical signals; converting, by a polarization transformer of the optical coherent imager, each of the incoming optical signals into a first optical component having a first polarization state and a second optical component having a second polarization state, wherein the first polarization state is orthogonal to the second polarization state; and guiding, by one or more polarization diversified optical couplers on an optical coherent sensor of the optical coherent imager, the first and second optical components of the incoming optical signals to one or more photodetectors of the optical coherent sensor so as to perform heterodyne detection with local oscillator light at each of the field-of-view positions of the optical coherent imager, thereby determining information of the targets at the field-of-view positions.

In one embodiment, emitting the outgoing optical signals comprises: generating one or more source optical signals from a light source; converting the source optical signals into the outgoing optical signals, wherein each outgoing optical signal has a first emission polarization state, by the polarization diversified optical couplers; and emitting the outgoing optical signals from the polarization diversified optical couplers.

In one embodiment, after emitting the outgoing optical signals from the polarization diversified optical couplers, the method further comprises transforming each of the outgoing optical signals from the first emission polarization state to a second emission polarization state by the polarization transformer of the optical coherent imager.

In one embodiment, converting the incoming optical signals comprises rotating the first polarization state of each of the incoming optical signals by a first predefined polarization angle and the second polarization state of each of the incoming optical signals by a second predefined polarization angle.

In one embodiment, converting the incoming optical signals comprises spatially displacing at least one of the first and second components of each of the incoming optical signals in accordance with the first and second polarization states such that the first and second components are incident respectively on first and second sub-couplers of each of the polarization diversified optical couplers.

BRIEF DESCRIPTION OF THE DRAWINGS

The skilled artisan will understand that the drawings are primarily for illustrative purposes and are not intended to limit the scope of the disclosed subject matter. The drawings are not necessarily to scale; in some instances, various aspects of the disclosed subject matter may be shown exaggerated or enlarged in the drawings to facilitate an understanding of different features.

FIG. 12A show a side view of a polarization transformation-separation configuration for use with a three-waveguide polarization-diversified free-space-to-waveguide coupler for out-coupling optical signals, in accordance with a further embodiment of the present disclosure.

FIG. 12B show a side view of the configuration illustrated in FIG. 12A used for in-coupling optical signals.

FIG. 12C shows a top view of the polarization states of the optical signals in FIG. 12A.

FIG. 12D shows a top view of the polarization states of the optical signals in FIG. 12B.

FIG. 13E shows a side view of the configuration as illustrated in FIG. 13C used for in-coupling optical signals.

FIG. 13F shows another side view of the configuration illustrated in FIG. 13E.

FIG. 13G shows a top view of the polarization states and path locations on the x-y plane of the optical signals in FIGS. 13C and 13D.

FIG. 13H shows a top view of the polarization states and path locations on the x-y plane of the optical signals in FIGS. 13E and 13F.

FIG. 15C shows a side view of a polarization transformation-separation configuration for use with a four-waveguide polarization-diversified free-sp ace-to-waveguide coupler for out-coupling optical signals, in accordance with an embodiment of the present disclosure.

FIG. 15D shows another side view of the configuration illustrated in FIG. 15C.

FIG. 15E shows a top view of the polarization states and path locations on the x-y plane of the optical signals in FIGS. 15C and 15D.

FIG. 15F shows a side view of the configuration as illustrated in FIG. 15C used for in-coupling optical signals.

FIG. 15G shows another side view of the configuration illustrated in FIG. 15F.

FIG. 15H shows a top view of the polarization states and path locations on the x-y plane of the optical signals in FIGS. 15F and 15G.

FIG. 17A shows a perspective view of a four-waveguide polarization-diversified free-space-to-waveguide coupler, in accordance with a further embodiment of the present disclosure.

FIG. 17B show a side view of a polarization transformation-separation configuration for use with a four-waveguide polarization-diversified free-sp ace-to-waveguide coupler for out-coupling optical signals, in accordance with a further embodiment of the present disclosure.

FIG. 17C show a side view of the configuration illustrated in FIG. 17B used for in-coupling optical signals.

FIG. 17D shows a top view of the polarization states of the optical signals in FIG. 17B.

FIG. 17E shows a top view of the polarization states of the optical signals in FIG. 17C.

DETAILED DESCRIPTION

The following detailed description includes systems, methods, techniques, and instruction sequences that illustrate embodiments of the present disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced with or without these specific details. In general, instruction instances, protocols, structures, and techniques well-known to those skilled in the art are not necessarily shown in detail.

Figure 1A:
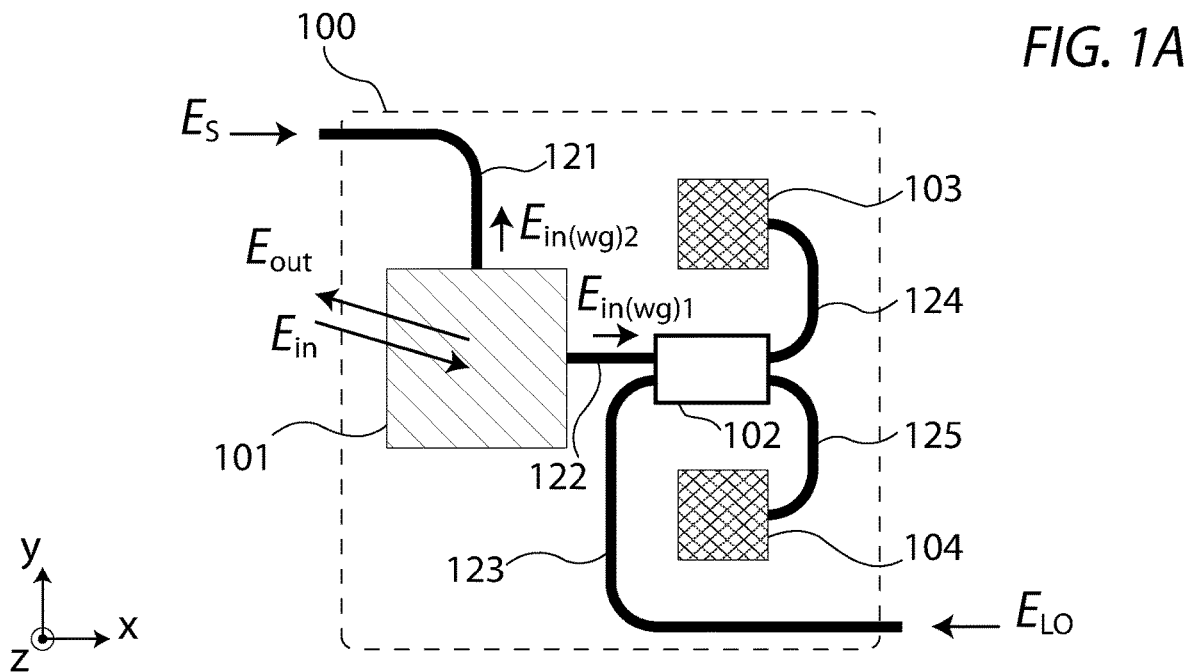
FIG. 1A shows a plan view of a coherent sensing unit for transmitting and receiving optical signals based on polarization diversity, in accordance with an embodiment of the present disclosure.
Figure 1B:
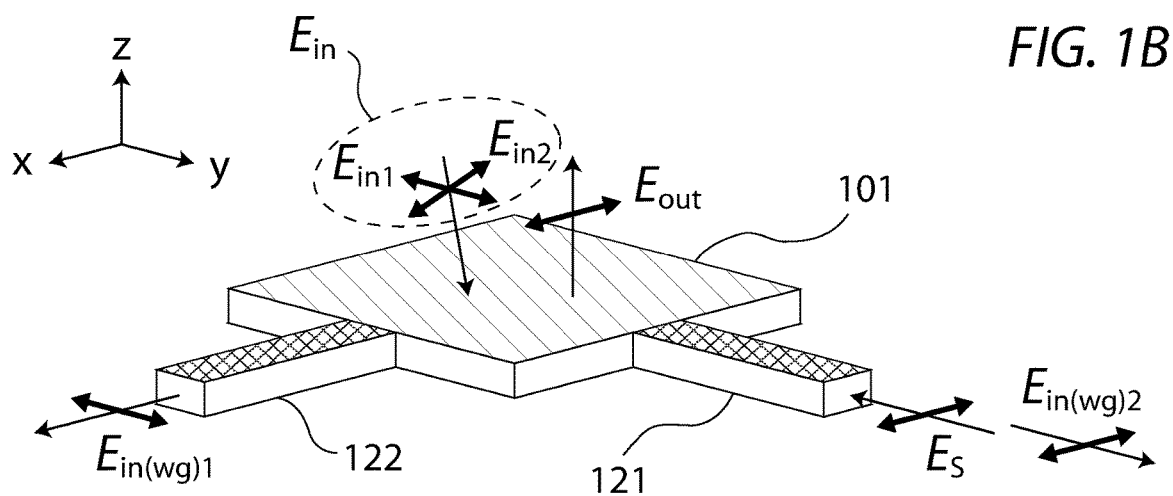
FIG. 1B shows a perspective view of a polarization-diversified free-space-to-wave guide coupler, in accordance with an embodiment of the present disclosure.

FIG. 1A shows a plan view of a coherent sensing unit 100 for transmitting and receiving optical signals based on polarization diversity, in accordance with an embodiment of the present disclosure. A plurality of coherent sensing units 100 may be used to form a coherent sensor array of an optical coherent imager. FIG. 1B shows a perspective view of a polarization-diversified free-space-to-waveguide coupler 101 of coherent sensing unit 100, in accordance with an embodiment of the present disclosure. Coherent sensing unit 100 may be implemented using photonic integrated circuit (PIC) technology on a photonic substrate. The surface of the photonic substrate may be represented by a plane spanned by the x and y axes of the coordinate system illustrated in FIGS. 1A and 1B. Photonic components of coherent sensing unit 100 implemented on the photonic substrate may or may not be covered by a cladding. Such components also may or may not be embedded in a cladding. For simplicity, the photonic substrate and the cladding are not shown in FIGS. 1A and 1B, as well as in other figures of the present disclosure. Additionally, in the following descriptions of the disclosure, a target that is to be detected by the optical coherent imager is taken to be located at a position along the positive z-direction away from the substrate surface and, if applicable, any optical components above the substrate surface. The target is not explicitly shown in the drawings for simplicity.

There are various common designs of photonic waveguides on a PIC chip, including but not limited to ridge waveguides, rib waveguides, buried waveguides, and slot waveguides. According to some embodiments, the waveguides of coherent sensing unit 100 of the present disclosure may be fabricated with the dimension along the z direction smaller than the dimensions on the x-y plane and are made to support various waveguide modes, including but not limited to transverse electric (TE) modes, transverse magnetic (TM) modes, and TE and TM modes, according to the coordinate system in the embodiments illustrated in FIGS. 1A and 1B. Here a TE mode may refer to a waveguide mode that has a dominant electric field component transverse to the propagation direction of the mode and the surface of the photonic substrate on which the waveguide resides, whereas a TM mode may refer to a waveguide mode that has a dominant magnetic field component transverse to the propagation direction of the mode and the surface of the photonic substrate on which the waveguide resides. Those skilled in the art should be familiar with such common designs of waveguides and the various modes supported by these waveguides.

Referring to FIG. 1A, optical source signal $E_S$ may be supplied to coherent sensing unit 100 through waveguide 121, while a local oscillator (LO) $E_{LO}$ may be supplied to coherent sensing unit 100 through waveguide 123. Optical source signal $E_S$ and LO $E_{LO}$ may or may not come from the same light source, where the light source may or may not be implemented on the same PIC chip comprising coherent sensing unit 100. According to some embodiments, optical source signal $E_S$ may be made to manifest as the fundamental TE mode in waveguide 121 and the LO $E_{LO}$ may be made to manifest as the fundamental TE mode in waveguide 123, by proper designs of system and method to couple the light source (or light sources) that gives rise to $E_S$ and $E_{LO}$ in the waveguides of the PIC chip comprising coherent sensing unit 100. Such designs are well-known to those skilled in the art. According to other embodiments, the optical source signal $E_S$ may intentionally be made to manifest as a TM mode or a TE mode other than the fundamental TE mode in waveguide 121. Similarly, according to some embodiments, the LO $E_{LO}$ may intentionally be made to manifest as a TM mode or a TE mode other than the fundamental TE mode in waveguide 123.

In FIG. 1A, polarization-diversified free-space-to-wave guide coupler 101 (hereafter referred to as coupler 101 for simplicity) may function as both a transmitter and a receiver. It is a two-waveguide coupler that is connected to waveguides 121 and 122, wherein a primary role of waveguide 121 is to direct signal light to coupler 101 and a primary role of waveguide 122 is to receive in-coupled light from coupler 101, even though in-coupled light from coupler 101 may also be directed to waveguide 121 according to some embodiments. Thus, with respect to coupler 101, waveguide 121 may be regarded as an out-coupling waveguide and waveguide 122 may be regarded as an in-coupling waveguide. A distinguishing feature of polarization-diversified free-space-to-waveguide coupler 101 is that, when the polarization state of an incoming optical signal ($E_{in}$ in FIG. 1A) arriving at coupler 101 is orthogonal to the polarization state of the outgoing optical signal ($E_{out}$ in FIG. 1A) output from coupler 101, the incoming optical signal may be in-coupled and directed to an in-coupling waveguide (waveguide 122 in FIG. 1A) that is distinct from the out-coupling waveguide (waveguide 121 in FIG. 1A). Here and hereafter, free space may refer to vacuum, air, a region above the surface of the coupler, or any homogenous medium with boundaries that have length-scales much larger (e.g., at least 10 times) than the wavelength of the optical signals propagating in it.

As a transmitter, coupler 101 may couple optical source signal $E_S$ from waveguide 121 into free space as an outgoing optical signal $E_{out}$, which may be used for target illumination by the optical coherent imager. The outgoing optical signal $E_{out}$ output by coupler 101 propagates in a direction that is out of the x-y plane (i.e., the propagation direction of $E_{out}$ has a nonzero z component) and is polarized with a polarization determined by the design of coupler 101. According to some embodiments, the polarization may be one of a pair of orthogonal linear polarizations according to a coordinate system defined by the design of coupler 101, wherein the coordinate system may or may not be the same as the coordinate system defined by the x, y, and z axes shown in FIGS. 1A and 1B. According to other embodiments, the polarization may be one of a pair of orthogonal polarizations other than a pair of linear polarizations, such as but not limited to, the right and left circular polarizations, and two orthogonal elliptical polarizations.

As a receiver, coupler 101 may couple an incoming optical signal $E_{in}$ into coherent sensing unit 100. Incoming optical signal $E_{in}$ is essentially an optical signal from a target (or a target signal) described previously. The incoming optical signal $E_{in}$ coupled by coupler 101 may be directed to either or both waveguides 121 and 122, depending on the polarization state of the incoming optical signal $E_{in}$. The polarization components of the incoming optical signal $E_{in}$ that are coupled to waveguides 121 and 122 depend on the design of coupler 101. According to some embodiments, a first polarization component of the incoming optical signal $E_{in}$ that is orthogonal to the polarization of the outgoing optical signal $E_{out}$ may be directed to waveguide 122 as an in-coupled optical signal $E_{in(wg)1}$, and a second polarization component of the incoming optical signal $E_{in}$ that is orthogonal to the first polarization of the incoming optical signal $E_{in}$ may be directed to waveguide 121 as an in-coupled optical signal $E_{in(wg)2}$. More details about the two polarization components in-coupled to coupler 101 will be described below with reference to FIG. 1B. The in-coupled optical signal $E_{in(wg)1}$ may be processed by the rest of the circuits of coherent sensing unit 100. In FIG. 1A, in-coupled optical signal $E_{in(wg)2}$ propagates in a direction opposite to the propagation direction of optical source signal $E_S$. According to some embodiments, in-coupled optical signal $E_{in(wg)2}$ may be left unattended without affecting the other parts of the PIC chip comprising the sensing unit 100. According to some embodiments such as but not limited to the embodiment illustrated in FIG. 7A, the in-coupled optical signal $E_{in(wg)2}$ may be processed by some other parts of the PIC chip comprising the sensing unit 700.

Figure 2:
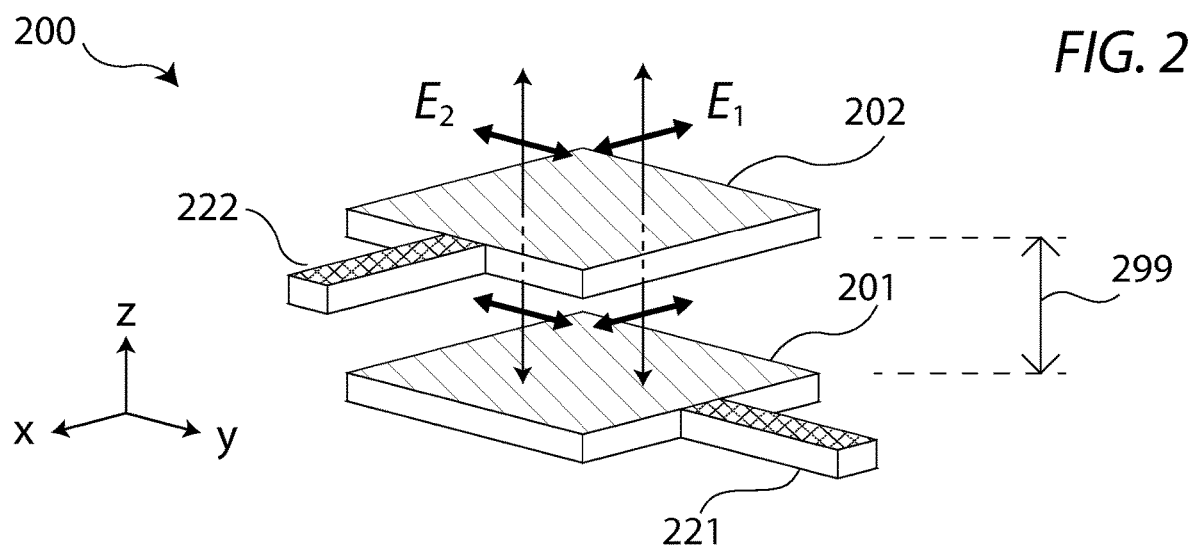
FIG. 2 shows a perspective view of a polarization-diversified free-space-to-waveguide coupler, in accordance with another embodiment of the present disclosure.
Figure 3:
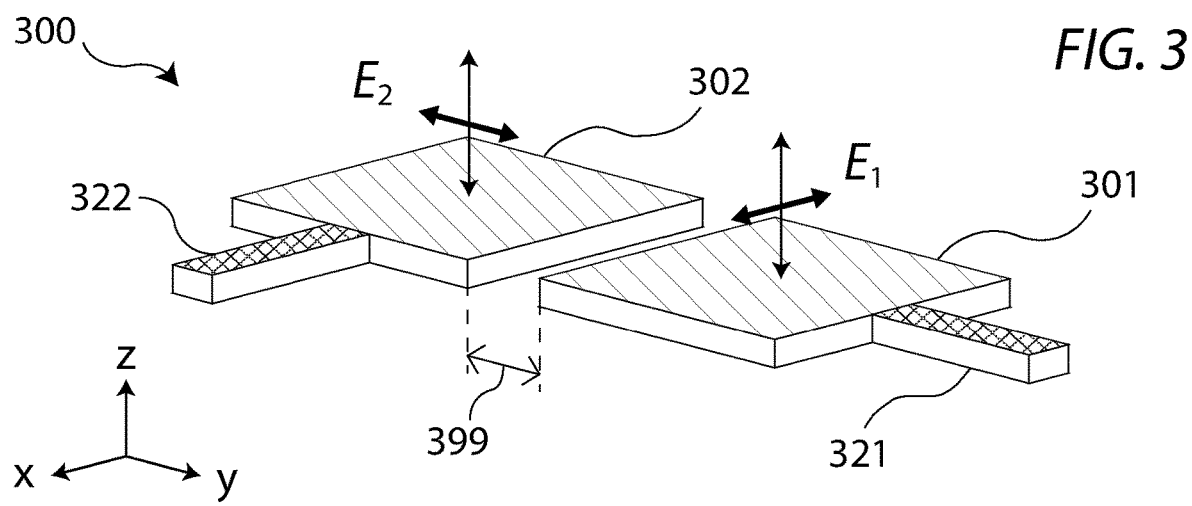
FIG. 3 shows a perspective view of a polarization-diversified free-space-to-waveguide coupler, in accordance with a further embodiment of the present disclosure.

In FIG. 1A, although coupler 101 is drawn as a single entity, coupler 101 may comprise a single photonic component or multiple photonic components. In some aspects, coupler 101 may be realized by a polarization-splitting free-space-to-waveguide coupler. Examples of a polarization-splitting free-sp ace-to-waveguide coupler include, but not limited to, a polarization-splitting grating coupler as described in "POLARIZATION SPLITTING GRATING COUPLERS," U.S. Pat. No. 7,006,732 and a metamaterial-based polarization-splitting free-space-to-wave guide coupler as described in "Integrated metamaterials for efficient and compact free-space-to-waveguide coupling," Optics Express 22, 27175-27182 (2014). Other examples of a polarization-splitting free-sp ace-to-waveguide coupler may include, but not limited to, those realized through either the plasmonic effect, or photonic micro/nano-structures, or both. Other embodiments of coupler 101 are illustrated in FIGS. 2 and 3 as described below. According to some embodiments, coupler 101 may also comprise any of TE-TM mode converters, splitters, and combiners. In some aspects, coupler 101 may comprise a single layer of photonic material. In other aspects, coupler 101 may comprise multiple layers of photonic materials, wherein the photonic materials of the different layers may be the same or different.

With reference to FIG. 1B, according to some embodiments, the optical source signal $E_S$ that propagates towards coupler 101 may manifest as a transverse electric (TE) mode in waveguide 121. As an example, optical source signal $E_S$ in FIG. 1B propagates towards the negative y direction with a dominant electric field component along the x direction. Coupler 101 may then couple optical source signal $E_S$ into free space to give rise to an outgoing optical signal $E_{out}$ that is polarized according to a polarization determined by the design of coupler 101. For example, outgoing optical signal $E_{out}$ can be linearly polarized along the x direction in FIG. 1B. In some cases, outgoing optical signal $E_{out}$ may propagate in a direction perpendicular to the substrate surface. For example, $E_{out}$ as shown in FIG. 1B propagates in the z direction. In other cases, outgoing optical signal $E_{out}$ may propagate in a direction not perpendicular to the substrate surface, that is, $E_{out}$ may propagate in a direction at a slanted angle with respect to the substrate surface.

As shown in FIG. 1B, an incoming optical signal $E_{in}$ may comprise either one or both of two orthogonal polarization components: a first polarization component $E_{LO,1}$ and a second polarization component $E_{in2}$. It is appreciated that when incoming optical signal $E_{in}$ comprises only first polarization component $E_{in1}$, the amplitude of second polarization component $E_{in2}$ is zero, and vice versa. Coupler 101 may be designed in such a way that the first polarization component $E_{LO,1}$ may be in-coupled and directed to waveguide 122 as in-coupled optical signal $E_{in(wg)1}$, wherein the first polarization component $E_{LO,1}$ is orthogonal to the polarization of outgoing optical signal $E_{out}$. Similarly, coupler 101 may be designed in such a way that the second polarization component $E_{in2}$ may be in-coupled and directed to waveguide 121 as in-coupled optical signal $E_{in(wg)2}$, which propagates in a direction opposite to the propagation direction of optical source signal $E_S$. The first polarization component $E_{LO,1}$ that is in-coupled and directed to waveguide 122 is orthogonal to the polarization of outgoing optical signal $E_{out}$, whereas the second polarization component $E_{in2}$ that is in-coupled and directed to waveguide 121 is orthogonal to the first polarization Emi. The second polarization $E_{in2}$ may or may not be the same as (up to a proportionality factor) the polarization of the outgoing optical signal $E_{out}$, as outgoing optical signal $E_{out}$ and incoming optical signal $E_{in}$ may propagate along the same or different directions. The specific polarization components of incoming optical signal $E_{in}$ that are coupled to waveguides 121 and 122 depend on the design of coupler 101.

According to some embodiments, coupler 101 may be designed to optimally in-couple optical signals according to a preferred polarization basis, which is referred to as the coupling polarization basis. According to some embodiments, one of the components of the coupling polarization basis may be the same as the polarization of outgoing optical signal $E_{out}$ output by coupler 101. As shown in FIG. 1B, for example, the coupling polarization basis may be a linear polarization basis (e.g., x and y polarizations), and coupler 101 may in-couple a first linear polarization component $E_{LO,1}$ (e.g., polarized along the y direction) of the incoming optical signal $E_{in}$ and direct it to waveguide 122, wherein the first linear polarization component $E_{LO,1}$ is orthogonal to the polarization of the linearly-polarized outgoing optical signal $E_{out}$ (e.g., x direction) and lies on a plane (e.g., y-z plane) parallel to a first component of the coupling polarization basis (i.e., y direction). Similarly, according to the linear polarization basis, coupler 101 may in-couple a second linear polarization component $E_{in2}$ (e.g., along a direction on the x-z plane in FIG. 1B) of the incoming optical signal $E_{in}$ and direct it to waveguide 121, wherein the second linear polarization component $E_{in2}$ lies on a plane (i.e., x-z plane) parallel to the polarization of the linearly-polarized outgoing optical signal $E_{out}$ (i.e., x direction) and a second component of the coupling polarization basis (i.e., x direction), and the second polarization $E_{in2}$ is orthogonal to the first polarization $E_{in1}$.

Coupler 101 may couple the incoming optical signal component $E_{LO,1}$ from free space to give rise to the in-coupled optical signal $E_{in(wg)1}$ in waveguide 122. According to some embodiments, in-coupled optical signal $E_{in(wg)1}$ may manifest as a TE mode in waveguide 122. As an example, in-coupled optical signal $E_{in(wg)1}$ propagates towards the positive x direction in FIG. 1B with a dominant electric field component along the y direction. Similarly, coupler 101 may couple incoming optical signal component $E_{in2}$ from free space to give rise to in-coupled optical signal $E_{in(wg)2}$ in waveguide 121. According to some embodiments, the in-coupled optical signal $E_{in(wg)2}$ may manifest as a TE mode in waveguide 121. As an example, in-coupled optical signal $E_{in(wg)2}$ propagates towards the positive y direction in FIG. 1B with a dominant electric field component along the x direction.

In some aspects, in-coupled optical signal $E_{in(wg)1}$ in waveguide 122, if present, may manifest as a single waveguide mode. According to some embodiments, the single waveguide mode may be the fundamental TE mode. According to other embodiments, the single waveguide mode may be the fundamental TM mode. According to further embodiments, the single waveguide mode may be a mode other than the fundamental TE mode or the fundamental TM mode. In other aspects, the in-coupled optical signal $E_{in(wg)1}$ in waveguide 122, if present, may manifest as a combination of multiple waveguide modes.

Similarly, in some aspects, in-coupled optical signal $E_{in(wg)2}$ in waveguide 121, if present, may manifest as a single waveguide mode. According to some embodiments, the single waveguide mode may be the fundamental TE mode. According to other embodiments, the single waveguide mode may be the fundamental TM mode. According to further embodiments, the single waveguide mode may be a mode other than the fundamental TE mode or the fundamental TM mode. In other aspects, in-coupled optical signal $E_{in(wg)2}$ in waveguide 121, if present, may manifest as a combination of multiple waveguide modes.

Although coupler 101 is intended to separate orthogonal polarization components of optical signals into two separate waveguides 121 and 122, it is not uncommon that cross-couplings may occur in some embodiments of coupler 101. For example, referring to FIG. 1B, even though the incoming optical signal $E_{in}$ may be linearly polarized along a direction that is orthogonal to the polarization of $E_{out}$ and lies on a plane parallel to the first component of the linear polarization basis (e.g., the incoming optical signal is $E_{in1}$), a nonzero fraction of $E_{in}$ may be directed to waveguide 121 in addition to the fraction of $E_{in}$ directed to waveguide 122. Similarly, for some embodiments, even though incoming optical signal $E_{in}$ may be linearly polarized along a direction that lies on a plane parallel to the polarization of $E_{out}$ and the second component of the linear polarization basis (e.g., the incoming optical signal is $E_{in2}$), a nonzero fraction of $E_{in}$ may be directed to waveguide 122 in addition to the fraction of $E_{in}$ directed to waveguide 121. Additionally, for some embodiments, a nonzero fraction of $E_S$ in waveguide 121 may propagate to waveguide 122 directly through coupler 101 in addition to the fraction of $E_S$ coupled to free space as the outgoing optical signal $E_{out}$ by coupler 101. Such cross-couplings may be regarded as imperfections of the design of coupler 101. According to some embodiments, coupler 101 may be designed to maximize the couplings of the respective polarization components with their intended waveguides while the cross-couplings may be minimized.

According to some embodiments, incoming optical signal $E_{in}$ may be coupled to coupler 101 at a spatial location on the surface of coupler 101 that is the same as the spatial location of outgoing optical signal $E_{out}$ emitted from coupler 101, even though $E_{out}$ and $E_{in}$ are drawn at different spatial locations on the surface of coupler 101 in FIG. 1B. According to other embodiments, incoming optical signal $E_{in}$ may be coupled to coupler 101 at a spatial location on the surface of coupler 101 different from the spatial location of outgoing optical signal $E_{out}$ emitted from coupler 101.

In some aspects, coupler 101 may emit outgoing optical signal $E_{out}$ into free space and couple incoming optical signal $E_{in}$ into sensing unit 100 at the same time. In other aspects, coupler 101 may emit outgoing optical signal $E_{out}$ into free space and couple incoming optical signal $E_{in}$ into sensing unit 100 at different times. In general, optical signals $E_{in}$ and $E_{out}$ may propagate along the same or different directions, though optical signals $E_{in}$ and $E_{out}$ are drawn to propagate along different directions in FIG. 1B.

Referring back to FIG. 1A, component 102 is a 2×2 optical coupler that mixes in-coupled optical signal $E_{in(wg)1}$ from waveguide 122 and the LO $E_{LO}$ from waveguide 123, and splits and directs the mixed signal to waveguides 124 and 125. Embodiments of 2×2 optical coupler 102 include, but not limited to, a directional coupler and a multi-mode interferometer (MMI). The mixing and splitting ratios of 2×2 optical coupler 102 depend on the design of coupler 102. In some aspects, 2×2 optical coupler 102 may have a splitting ratio of 50/50. In other aspects, 2×2 optical coupler 102 may have a splitting ratio other than 50/50.

In some aspects, in-coupled optical signal $E_{in(wg)1}$ propagating in waveguide 122 and the LO $E_{LO}$ propagating in waveguide 123 may manifest as the same waveguide mode. In other aspects, in-coupled optical signal $E_{in(wg)1}$ propagating in waveguide 122 and LO $E_{LO}$ propagating in waveguide 123 may manifest as different waveguide modes. When the in-coupled optical signal $E_{in(wg)1}$ propagating in waveguide 122 and the LO $E_{LO}$ propagating in waveguide 123 manifest as different waveguide modes, according to some embodiments, 2×2 optical coupler 102 may additionally include one or more mode converters at one or both of its input ports (i.e., waveguides 122 and 123), so as to convert one or both of in-coupled optical signal $E_{in(wg)1}$ propagating in waveguide 122 and LO $E_{LO}$ propagating in waveguide 123 to manifest as the same waveguide mode. According to other embodiments, 2×2 optical coupler 102 may not include such mode converters and may still mix, split and direct in-coupled optical signal $E_{in(wg)1}$ propagating in waveguide 122 and LO $E_{LO}$ propagating in waveguide 123 that manifest as different waveguide modes.

In FIG. 1A, component 103 is a square-law photodetector (responding to the power of an optical signal proportional to the square of its electric field) that receives and detects the optical signal from waveguide 124. Similarly, in FIG. 1A, component 104 is a square-law photodetector that receives and detects the optical signal from waveguide 125. According to some embodiments, 2×2 optical coupler 102 may be a 50/50 2×2 optical coupler, and coupler 102 together with photodetectors 103 and 104 may form a balanced optical heterodyne detection setup. According to some embodiments, one of photodetectors 103 and 104 may be omitted from coherent sensing unit 100 wherein the other remaining photodetector together with coupler 102, which may or may not be a 50/50 coupler, may form a single-detector optical heterodyne detection setup.

According to some embodiments, photodetectors 103 and 104 may manifest as a single combined photodetector with two optical inputs connecting to waveguides 124 and 125. The combined photodetector with two optical inputs may measure any one or more of the intensities, the sum of the intensities, and the difference of the intensities of the optical signals from the two inputs.

According to some embodiments, photodetectors 103 and 104 may be connected to an output electronic circuit comprising electronic components such as, but not limited to, any one or more of transimpedance amplifiers (TIA), transistors, diodes, resistors, capacitors, and electrical switches, that are used to process the electrical outputs of photodetectors 103 and 104. This output electronic circuit is not shown in FIG. 1A.

In FIG. 1A, coherent sensing unit 100 may comprise components not explicitly shown, including but not limited to any one or more of electro-optical components and thermo-optical components, for any one or more of phase, amplitude, frequency, wavelength, and temporal controls.

FIG. 2 shows a perspective view of a polarization-diversified free-space-to-waveguide coupler 200, in accordance with another embodiment of the present disclosure. Coupler 200 comprises two sub-couplers 201 and 202 implemented on different layers of the PIC chip. According to some embodiments, one of the two sub-couplers 201 or 202 may be designed to optimally couple optical signals with a specific polarization state and the other sub-coupler may be designed to optimally couple optical signals with a corresponding orthogonal polarization state. For example, sub-coupler 201 may be designed to optimally couple incoming or outgoing optical signal $E_1$ that is linearly polarized along a certain direction (e.g., along the x direction), whereas sub-coupler 202 may be designed to optimally couple incoming or outgoing optical signal $E_2$ that is linearly polarized along a direction orthogonal to the polarization of $E_1$ (e.g., along the y direction). Sub-couplers 201 and 202 may or may not be aligned to the same x-y positions.

Referring to FIG. 2, sub-coupler 201 may be a free-space-to-waveguide coupler, such as but not limited to a grating coupler, that may optimally couple with optical signal $E_1$ polarized according to a polarization (e.g., linear polarization along the x direction) and minimally couple with optical signal $E_2$ polarized according to a polarization (e.g., linear polarization along the y direction) orthogonal to the polarization of $E_1$. Similarly, sub-coupler 202 may be a free-space-to-waveguide coupler, such as but not limited to a grating coupler, that may optimally couple with optical signal $E_2$ polarized according to a polarization (e.g., linear polarization along the y direction) and minimally couple with optical signal $E_1$ polarized according to a polarization (e.g., linear polarization along the x direction) orthogonal to the polarization of $E_2$. Sub-couplers 201 and 202 may or may not be of the same design. In general, the pair of orthogonally polarized optical signals $E_1$ and $E_2$ that are optimally coupled with one and minimally coupled with the other of sub-couplers 201 and 202 may be any of a pair of orthogonal linear polarizations, right and left circular polarizations, and a pair of orthogonal elliptical polarizations.

In FIG. 2, orthogonal optical signals $E_1$ and $E_2$ are drawn at different spatial locations on the surface of sub-couplers 201 and 202 for illustrative purpose. In general, sub-coupler 201 may optimally couple with optical signal $E_1$ and minimally couple with $E_2$ at the same spatial location or at different spatial locations on the surface of sub-coupler 201. Similarly, in general, sub-coupler 202 may optimally couple with optical signal $E_2$ and minimally couple with $E_1$ at the same spatial location or at different spatial locations on the surface of sub-coupler 202.

In FIG. 2, optical signals $E_1$ and $E_2$ are drawn to propagate along a direction perpendicular to the plane of the substrate surface, i.e., along the z direction. In general, optical signals $E_1$ and $E_2$ may propagate along directions that may or may not be perpendicular to the plane of the substrate surface. Additionally, optical signals $E_1$ and $E_2$ may propagate along different directions, though optical signals $E_1$ and $E_2$ are drawn to propagate along the same direction in FIG. 2.

In FIG. 2, the cross coupling between sub-couplers 201 and 202 may be minimized by choosing an appropriate vertical separation 299 between them. Vertical separation 299 may be formed by disposing a photonic material layer (or an air gap) between sub-couplers 201 and 202 having a thickness from 50 nanometers to 5 millimeters. In general, the choice of separation 299 may depend on a combination of factors, including but not limited to the PIC technology, fabrication process, photonic materials used between sub-couplers 201 and 202, the wavelength of signal $E_1$, the wavelength of signal $E_2$, the design of sub-coupler 201, and the design of sub-coupler 202.

According to some embodiments, sub-coupler 201 may comprise a single layer of photonic material. According to other embodiments, sub-coupler 201 may comprise multiple layers of photonic materials, wherein the photonic materials of the different layers may be the same or different. Similarly, according to some embodiments, sub-coupler 202 may comprise a single layer of photonic material. According to other embodiments, sub-coupler 202 may comprise multiple layers of photonic materials, wherein the photonic materials of the different layers may be the same or different.

According to some embodiments, for use in coherent sensing unit 100 in FIG. 1A, sub-coupler 201 in FIG. 2 may be used as a transmitter whereas sub-coupler 202 in FIG. 2 may be used as a receiver, wherein sub-coupler 201 as a transmitter is farther away from the target and sub-coupler 202 as a receiver is closer to the target. In such a circumstance, waveguide 221 in FIG. 2 may be the same as (or equivalently connected to) waveguide 121 in FIG. 1A as an out-coupling waveguide, whereas waveguide 222 in FIG. 2 may be the same as (or equivalently connected to) waveguide 122 in FIG. 1A as an in-coupling waveguide. According to other embodiments, for use in coherent sensing unit 100 in FIG. 1A, sub-coupler 201 in FIG. 2 may be used as a receiver whereas sub-coupler 202 in FIG. 2 may be used as a transmitter, wherein sub-coupler 201 as a receiver is farther away from the target and sub-coupler 202 as a transmitter is closer to the target. In such a circumstance, waveguide 221 in FIG. 2 may be the same as (or equivalently connected to) waveguide 122 in FIG. 1A as an in-coupling waveguide, whereas waveguide 222 in FIG. 2 may be the same as (or equivalently connected to) waveguide 121 in FIG. 1A as an out-coupling waveguide.

FIG. 3 shows a perspective view of a polarization-diversified free-space-to-waveguide coupler 300, in accordance with a further embodiment of the present disclosure. Coupler 300 comprises two sub-couplers 301 and 302 implemented as two separate couplers on the same layer of the PIC chip. According to some embodiments, one of the two sub-couplers may be designed to optimally couple with optical signals with a polarization state and the other sub-coupler may be designed to optimally couple with optical signals with another polarization state. According to some embodiments, the two polarization states may be orthogonal to each other. According to other embodiments, the two polarization states may not be orthogonal to each other. For example, sub-coupler 301 may be designed to optimally couple with optical signal $E_1$ that is linearly polarized along the x direction, whereas sub-coupler 302 may be designed to optimally couple with optical signal $E_2$ that is linearly polarized along the y direction.

Referring to FIG. 3, sub-coupler 301 may be a free-space-to-waveguide coupler, such as but not limited to a grating coupler, that may optimally couple with optical signal $E_1$ polarized according to a certain polarization (e.g., linear polarization along the x direction) and minimally couple with optical signal with a polarization (e.g., linear polarization along y direction) orthogonal to that of $E_1$. Similarly, sub-coupler 302 may be a free-space-to-waveguide coupler, such as but not limited to a grating coupler, that may optimally couple with optical signal $E_2$ polarized according to a certain polarization (e.g., linear polarization along the y direction) and minimally couple with optical signal with a polarization (e.g., linear polarization along the x direction) orthogonal to that of $E_2$. Sub-couplers 301 and 302 may or may not be of the same design.

According to other embodiments, one of sub-couplers 301 and 302 may be designed to optimally couple with optical signals with a polarization state and the other sub-coupler may be a polarization-independent free-space-to-waveguide coupler that is designed to optimally couple with optical signals with any polarization state. An example of a polarization-independent free-space-to-waveguide coupler is described in "Polarization-independent grating couplers for silicon-on-insulator nanophotonic waveguides," Optics Letters Vol. 36, No. 6, p. 796 (2011). With reference to FIG. 3, on one hand, sub-coupler 301 may be a free-space-to-waveguide coupler, such as but not limited to a grating coupler, that may optimally couple with optical signal $E_1$ polarized according to one polarization (e.g., linear polarization along the x direction) and minimally couple with optical signal with a polarization (e.g., linear polarization along y direction) orthogonal to that of $E_1$. On the other hand, sub-coupler 302 may be a polarization-independent free-space-to-waveguide coupler that may optimally couple with optical signal $E_2$ with any polarization, wherein optical signal $E_2$ may or may not be orthogonal to optical signal $E_1$.

In FIG. 3, the cross coupling between sub-couplers 301 and 302 may be minimized by choosing an appropriate lateral separation 399 between the sub-couplers. Lateral separation 399 may be formed by disposing sub-couplers 301 and 302 on the same substrate surface but separated by a distance from 50 nanometers to 5 millimeters. In general, the choice of lateral separation 399 may depend on a combination of factors, including but not limited to the PIC technology, fabrication process, photonic materials used for the medium between sub-couplers 301 and 302, the wavelength of the signal $E_1$, the wavelength of the signal $E_2$, the design of coupler 301, and the design of coupler 302.

According to some embodiments, sub-coupler 301 may comprise a single layer of photonic material. According to other embodiments, sub-coupler 301 may comprise multiple layers of photonic materials, wherein the photonic materials of the different layers may be the same or different. Similarly, according to some embodiments, sub-coupler 302 may comprise a single layer of photonic material. According to other embodiments, sub-coupler 302 may comprise multiple layers of photonic materials, wherein the photonic materials of the different layers may be the same or different.

In FIG. 3, optical signals $E_1$ and $E_2$ are drawn to propagate along a direction perpendicular to the plane of the substrate surface, i.e., along the z direction. In general, optical signals $E_1$ and $E_2$ may propagate along directions that may or may not be perpendicular to the plane of the substrate surface. Additionally, optical signals $E_1$ and $E_2$ may propagate along different directions, though optical signals $E_1$ and $E_2$ are drawn to propagate along the same direction in FIG. 3.

According to some embodiments, for use in coherent sensing unit 100 in FIG. 1A, sub-coupler 301 in FIG. 3 may be used as a transmitter whereas sub-coupler 302 in FIG. 3 may be used as a receiver. In such a circumstance, waveguide 321 in FIG. 3 may be the same as (or equivalently connected to) waveguide 121 in FIG. 1A as an out-coupling waveguide whereas waveguide 322 in FIG. 3 may be the same as (or equivalently connected to) waveguide 122 in FIG. 1A as an in-coupling wave guide.

Figure 4A:
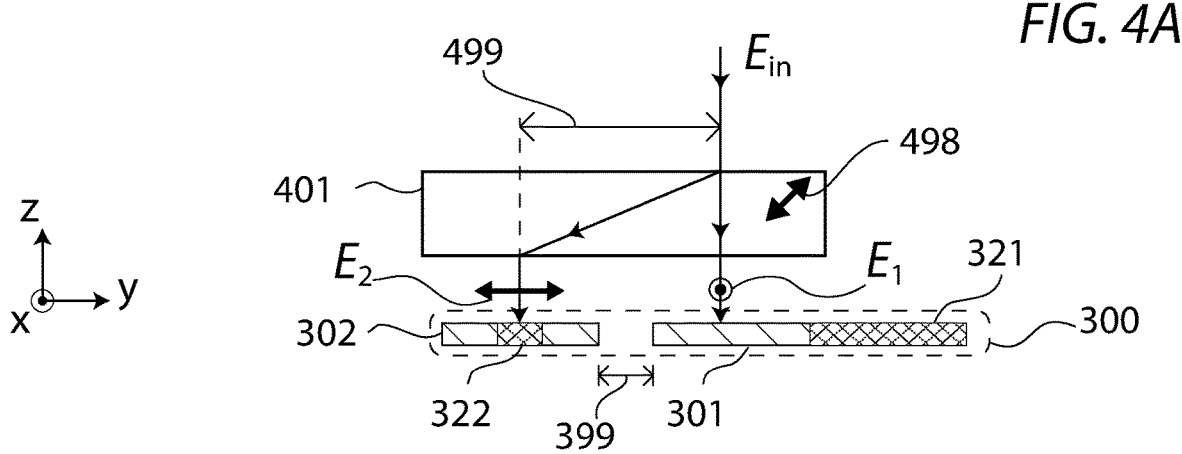
FIG. 4A shows a side view of a polarization-separation configuration for in-coupling optical signals, in accordance with an embodiment of the present disclosure.
Figure 4B:
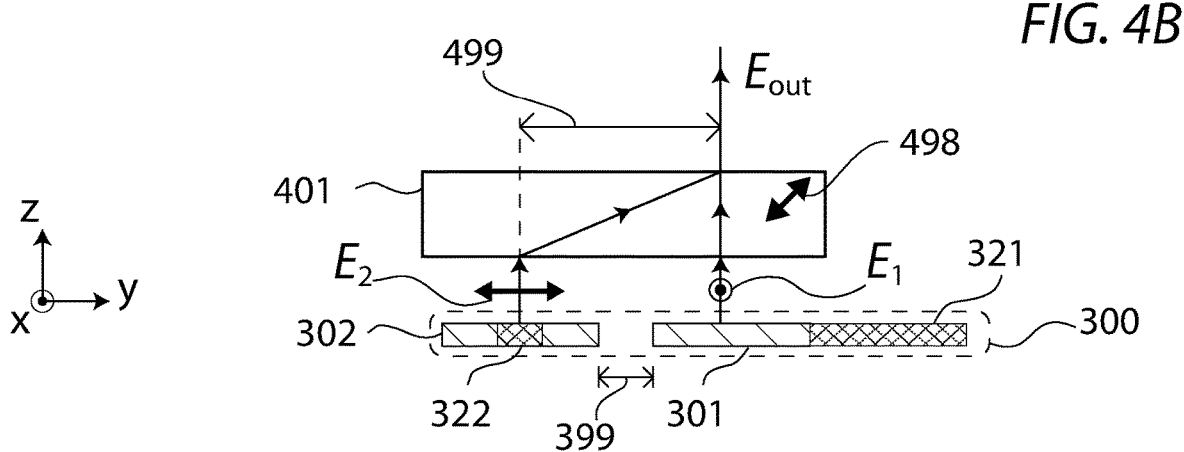
FIG. 4B shows a side view of the polarization-separation configuration in FIG. 4A for out-coupling optical signals.
Figure 4C:
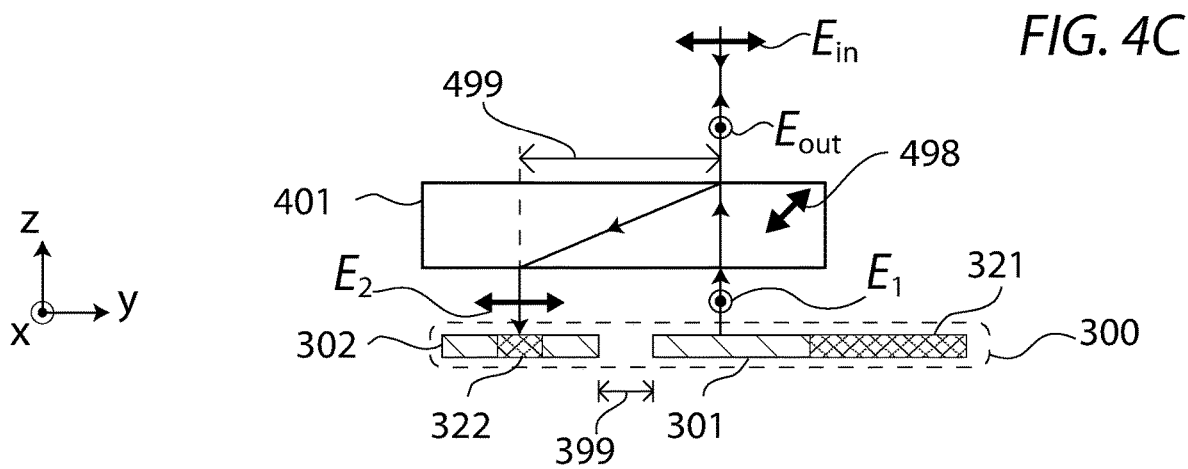
FIG. 4C shows a side view of the polarization-separation configuration in FIG. 4A for in-coupling and out-coupling optical signals.

FIG. 4A shows a side view of a polarization-separation configuration for in-coupling optical signals, in accordance with an embodiment of the present disclosure. FIG. 4B shows a side view of the polarization-separation configuration in FIG. 4A for out-coupling optical signals. FIG. 4C shows a side view of the polarization-separation configuration in FIG. 4A for in-coupling and out-coupling optical signals. The polarization-separation configuration, as shown in FIGS. 4A, 4B and 4C, may be used with polarization-diversified free-space-to-waveguide coupler 300 in FIG. 3 to direct optical signal $E_1$ (coupled with sub-coupler 301) and optical signal $E_2$ (coupled with sub-coupler 302) to propagate along a common optical path in free space, wherein the common optical path lies between an optical component 401 and the target.

The polarization-separation configuration, as illustrated in FIG. 4A, comprises a polarization-dependent beam-separator 401. According to some embodiments, polarization-dependent beam-separator 401 may be a birefringent beam displacer. According to some embodiments, a birefringent beam displacer may be made of one or more materials such as, but not limited to, calcite crystal, alpha barium borate crystal, yttrium vanadate crystal, or rutile crystal. A birefringent beam displacer is well-known in the art. According to other embodiments, polarization-dependent beam-separator 401 may be a polarization-dependent beam-separator other than a birefringent beam displacer, such as but not limited to a birefringent wedge, a polarization beam splitter, a polarization-dependent grating, or a polarization-dependent metalens.

According to some embodiments, polarization-dependent beam-separator 401 may be a component that is separate from the PIC chip comprising polarization-diversified free-space-to-waveguide coupler 300 as illustrated in FIG. 4A. According to other embodiments, polarization-dependent beam-separator 401 may be attached to the surface of the PIC chip comprising coupler 300. According to further embodiments, polarization-dependent beam-separator 401 may be within or be part of the PIC chip comprising coupler 300.

For optical signal reception, according to the embodiment in FIG. 4A, an incoming optical signal $E_{in}$ may arrive at the polarization-dependent beam-separator 401 from a target. Polarization-dependent beam-separator 401 may split the incoming optical signal $E_{in}$ into two optical signals $E_1$ and $E_2$, wherein the polarizations of optical signals $E_1$ and $E_2$ are orthogonal to each other. The splitting of the optical signal may depend on the polarization of the incoming optical signal. One of optical signals $E_1$ and $E_2$ is the ordinary ray (o-ray) and the other is the extraordinary ray (e-ray). For example, optical signal $E_1$ may be the o-ray whereas optical signal $E_2$ may be the e-ray. It is appreciated that, in addition to their common usages for the case of a birefringent beam-separator, the terms o-ray and e-ray used herein may generally be referred to two orthogonally polarized light rays that are split by polarization-dependent beam-separator 401, wherein the splitting is defined by the characteristics of the polarization-dependent beam-separator.

The polarizations of optical signals $E_1$ and $E_2$ depend on the permittivities of the materials of polarization-dependent beam-separator 401, the orientation of optic axis 498 and the incident angle of incoming optical signal $E_{in}$. In this embodiment, the incident angle of incoming optical signal $E_{in}$ is close to the normal of the surface of polarization-dependent beam-separator 401. As such, polarization-dependent beam-separator 401 may be fabricated and optic axis 498 may be oriented in such a way that the o-ray ($E_1$) is polarized along the x direction and the e-ray ($E_2$) is polarized along the y direction upon emerging from and exiting polarization-dependent beam-separator 401.

According to some embodiments, the o-ray and e-ray (e.g., optical signals $E_1$ and $E_2$ in FIG. 4A) may be laterally displaced upon emergence from polarization-dependent beam-separator 401. The lateral displacements may depend on any one or more of the factors including but not limited to the geometries (e.g., shape and thickness), permittivities of the materials, and orientation of optic axis 498 of polarization-dependent beam-separator 401, and the wavelength and incident angle of incoming optical signal $E_{in}$. For near normal incidence of incoming optical signal $E_{in}$, o-ray $E_1$ may propagate along a first optical path with a first lateral displacement (e.g., $E_1$ continues the path of the incoming optical signal $E_{in}$ with null lateral displacement as illustrated in FIG. 4A), whereas the e-ray $E_2$ may propagate along a second optical path with a second lateral displacement 499 with respect to the path of incoming optical signal $E_{in}$ as illustrated in FIG. 4A, wherein the second optical path of e-ray $E_2$ is distinct from the first optical path of o-ray $E_1$, and the second lateral displacement of e-ray $E_2$ is different from the first lateral displacement of o-ray $E_1$.

According to some embodiments, optical signals $E_1$ and $E_2$ may be incident on sub-couplers 301 and 302 at angles close to normal incidence, as shown in FIG. 4A. According to other embodiments, optical signals $E_1$ and $E_2$ may be incident on sub-couplers 301 and 302 at angles other than normal incidence. With any incident angle of incoming optical signal Ern and the properties of polarization-dependent beam-separator 401 (such as its geometries, permittivities, and orientation of the optic axis), the polarizations and propagation directions of o-ray $E_1$ and e-ray $E_2$ may be determined through the Maxwell's equations.

According to some embodiments, sub-coupler 301 may be configured to optimally couple with o-ray $E_1$ based on its polarization and propagation direction, wherein the polarization and propagation direction of o-ray $E_1$ may be pre-determined. Similarly, according to some embodiments, sub-coupler 302 may be configured to optimally couple with e-ray $E_2$ based on its polarization and propagation direction, wherein the polarization and propagation direction of e-ray $E_2$ may be pre-determined. For example, as shown in FIG. 4A, the incident angle of incoming optical signal $E_{in}$ may be close to the normal of the surface of polarization-dependent beam-separator 401 and optic axis 498 may be oriented at an angle on the y-z plane. As such, sub-coupler 301 may be configured to optimally couple with o-ray $E_1$ propagating along the z direction and polarized along the x direction, whereas sub-coupler 302 may be configured to optimally couple with e-ray $E_2$ propagating along the z direction and polarized along the y direction. Lateral separation 399 between sub-couplers 301 and 302 may be determined by incorporating the information of lateral separation 499 between o-ray $E_1$ and e-ray $E_2$.

According to other embodiments, sub-coupler 301 may not be configured to optimally couple with o-ray $E_1$ based on its polarization. That is, the optimal polarization for coupling with sub-coupler 301 may not be the same as the polarization of o-ray $E_1$. Similarly, according to other embodiments, sub-coupler 302 may not be configured to optimally couple with e-ray $E_2$ based on its polarization. That is, the optimal polarization for coupling with sub-coupler 302 may not be the same as the polarization of e-ray $E_2$. According to further embodiments, sub-coupler 301 may not be configured to optimally couple with o-ray $E_1$ based on the propagation direction of o-ray $E_1$. Similarly, according to further embodiments, sub-coupler 302 may not be configured to optimally couple with e-ray $E_2$ based on the propagation direction of e-ray $E_2$.

According to some embodiments, sub-coupler 301 may be a polarization-independent coupler and may be configured to optimally couple with o-ray $E_1$ based only on the propagation direction of o-ray $E_1$. Similarly, according to some embodiments, sub-coupler 302 may be a polarization-independent coupler and may be configured to optimally couple with e-ray $E_2$ based only on the propagation direction of e-ray $E_2$.

For optical signal transmission, as shown in FIG. 4B, optical signal $E_1$ outgoing from sub-coupler 301 may be polarized according to the polarization of the o-ray defined by polarization-dependent beam-separator 401 (e.g., linear polarization along the x direction as shown in FIG. 4B) and optical signal $E_2$ outgoing from sub-coupler 302 may be polarized according to the polarization of the e-ray defined by polarization-dependent beam-separator 401 (e.g., linear polarization along the y direction as shown in FIG. 4B). Propagation of optical signals through polarization-dependent beam-separator 401 is reversible. Thus, after passing through polarization-dependent beam-separator 401, optical signals $E_1$ and $E_2$ may be combined to give rise to an outgoing optical signal $E_{out}$ that propagates along an optical path away from an upper surface of polarization-dependent beam-separator 401 (e.g., a path that continues the path of optical signal $E_1$ with null lateral displacement as illustrated in FIG. 4B), wherein optical signals $E_1$ and $E_2$ are coherent with respect to each other and the outgoing optical signal $E_{out}$ is polarized according to the polarizations, amplitudes, and relative phase of optical signals $E_1$ and $E_2$.

According to some embodiments, optical signals $E_1$ and $E_2$ emerging from and exiting polarization-dependent beam-separator 401 may not perfectly overlap spatially. This may give rise to spatially varying polarization of outgoing optical signal $E_{out}$. According to some embodiments, polarization-dependent beam-separator 401 and sub-couplers 301 and 302 may be configured in such a way that the spatial overlap between optical signals $E_1$ and $E_2$ may give rise to an outgoing optical signal $E_{out}$ that has a dominant (i.e., greater than 50%) polarization state.

Polarization-dependent beam-separator 401 may be used with coupler 300 to transmit and receive optical signals, wherein one of sub-couplers 301 and 302 may be used for transmitting an outgoing optical signal $E_{out}$, while the other one of sub-couplers 301 and 302 may be used for receiving an incoming optical signal $E_{in}$. Optical signals $E_{out}$ and $E_{in}$ may propagate along a common optical path that lies between optical component 401 and the target. As shown in FIG. 4C, on one hand, optical signal $E_1$ outgoing from sub-coupler 301 may be polarized according to the polarization of the o-ray defined by polarization-dependent beam-separator 401. After passing through polarization-dependent beam-separator 401, optical signal $E_1$ may give rise to outgoing optical signal $E_{out}$, wherein the polarizations of optical signals $E_1$ and $E_{out}$ are the same. For example, if optical signal $E_1$ outgoing from sub-coupler 301 is polarized along the polarization of the o-ray of polarization-dependent beam-separator 401 (i.e., linearly polarized along the x direction), outgoing optical signal $E_{out}$ may emerge from and exit polarization-dependent beam-separator 401 with a polarization that is the same as the polarization of optical signal $E_1$ (i.e., along the x direction) and propagate along an optical path away from polarization-dependent beam-separator 401 (e.g., a path that continues the path of optical signal $E_1$ without lateral displacement as illustrated in FIG. 4C).

On the other hand, according to some embodiments, an incoming optical signal EH, may be polarized according to the polarization of the e-ray defined by polarization-dependent beam-separator 401 and propagate along the same optical path as the outgoing optical signal $E_{out}$, but in a reversed direction. After passing through polarization-dependent beam-separator 401, incoming optical signal $E_{in}$ may give rise to optical signal $E_2$ that may be coupled with sub-coupler 302, wherein the polarizations of optical signals $E_{in}$ and $E_2$ are the same. For example, as shown in FIG. 4C, an incoming optical signal $E_{in}$ linearly polarized along the y direction incident at a direction normal to an upper surface of polarization-dependent beam-separator 401 may give rise to optical signal $E_2$ that is linearly polarized along the y direction and couples with sub-coupler 302, wherein optical signal $E_2$ is laterally displaced by polarization-dependent beam-separator 401. As illustrated in FIG. 4C, the polarizations of outgoing optical signal $E_{out}$ and incoming optical signal $E_{in}$ are orthogonal to each other, and the polarizations of optical signals $E_1$ and $E_2$ are orthogonal to each other. In one embodiment, when the polarization of incoming optical signal $E_{in}$ is not orthogonal to the polarization of outgoing optical signal $E_{out}$, incoming optical signal $E_{in}$ may be split into an o-ray and an e-ray, wherein the o-ray may couple with sub-coupler 301 and the e-ray may couple with sub-coupler 302, as illustrated in the embodiment in FIG. 4A.

According to some embodiments, the roles of sub-couplers 301 and 302 may be interchanged, so that the outgoing optical signal may be e-ray $E_2$, instead of o-ray $E_1$ as illustrated in FIG. 4C.

As shown in FIG. 4C, a coupling polarization basis may be formed by a pair of polarizations of optical signals which couple with sub-couplers 301 and 302 optimally. According to some embodiments, the coupling polarization basis may be the same as the polarizations of the o-ray and e-ray corresponding to polarization-dependent beam-separator 401. According to other embodiments, the coupling polarization basis may be different from the polarizations of the o-ray and e-ray corresponding to polarization-dependent beam-separator 401.

According to some embodiments, the difference between the coupling polarization basis and the polarizations of the o-ray and e-ray corresponding to polarization-dependent beam-separator 401 may be minimized by proper designs of the optical coherent imager. Such proper designs may comprise an optical component (such as one or more lenses) to ensure incoming optical signals and outgoing optical signals to propagate along directions that maintain near normal incidence upon the surfaces of polarization-dependent beam-separator 401. Such proper designs may also comprise an optical component (such as one or more lenses) to ensure incoming optical signals and outgoing optical signals to couple with sub-couplers 301 and 302 at incident angles close to the optimal coupling directions of sub-couplers 301 and 302.

Referring to FIG. 4C, when the coupling polarization basis may be different from the polarizations of the o-ray and e-ray corresponding to polarization-dependent beam-separator 401, the optical signal out-coupled by coupler 300 may give rise to two outgoing optical signals emerging from polarization-dependent beam-separator 401, wherein the two outgoing optical signals are optical signals corresponding to the o-ray and the e-ray. Under such a circumstance, optical signal $E_1$ emitted by sub-coupler 301 may give rise to an outgoing o-ray that is the same as the outgoing optical signal $E_{out}$ and an outgoing e-ray that propagates along an optical path different from that of outgoing optical signal $E_{out}$ (not shown). For an optical coherent imager using polarization diversity to enable shared path for transmitting and receiving optical signals, the outgoing e-ray in this circumstance may be disregarded, as an incoming optical signal that shares the same optical path as the outgoing e-ray may not be able to be coupled with in-coupling sub-coupler 302 as exemplified in FIG. 4C.

According to some embodiments, either one or both of sub-couplers 301 and 302 in FIG. 4C may be a polarization-independent free-space-to-waveguide coupler. Using a polarization-independent free-space-to-waveguide coupler may be able to optimally couple an incoming optical signal Ern irrespective of the polarizations of the o-ray and the e-ray corresponding to polarization-dependent beam-separator 401.

In some circumstances of optical coherent sensing, the optical signal reflected by the target has a dominant polarization component that is the same as the optical signal that illuminates the target. Such circumstances include but not limited to specular reflection and light reflection off a shiny target surface. To optimize the signal received, a polarization transformation mechanism may thus be desirable to be used with a coherent sensing unit that utilizes polarization diversity for out-coupling and in-coupling optical signals.

Figure 5A:
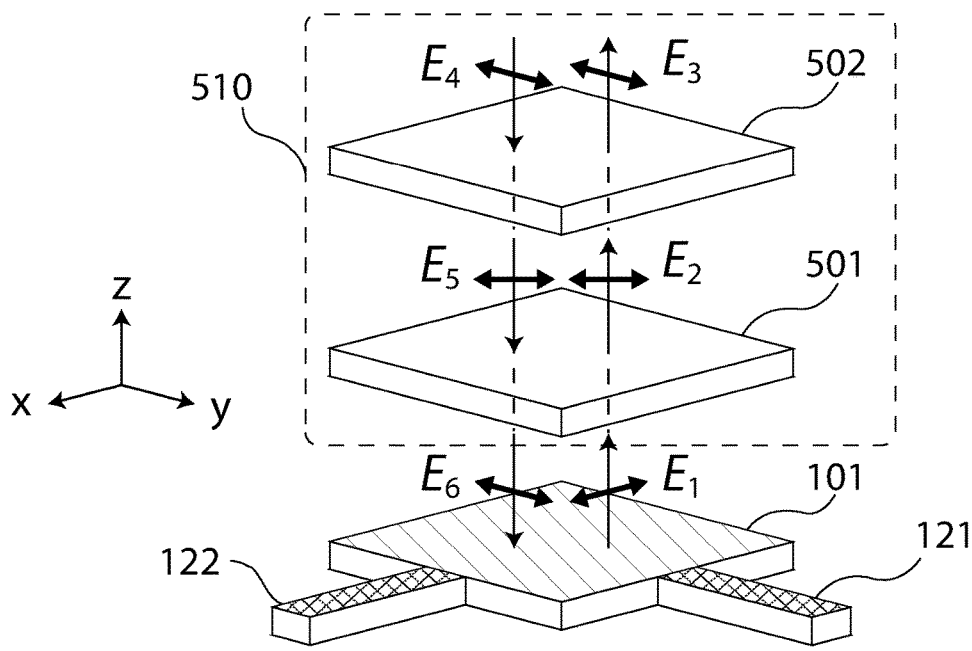
FIG. 5A shows a perspective view of a polarization transformation configuration realized by the Faraday effect, in accordance with an embodiment of the present disclosure.
Figure 5B:
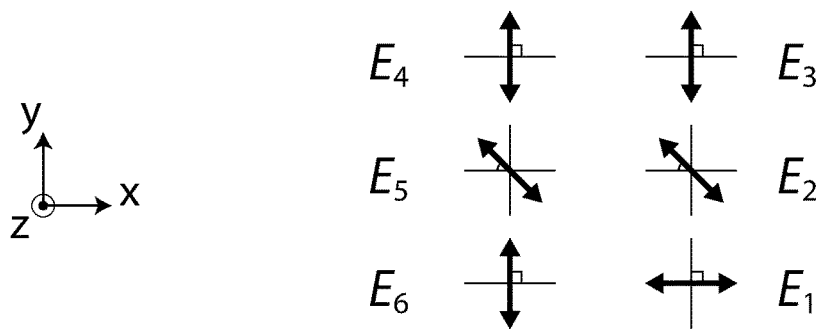
FIG. 5B shows a top view of the polarization states of optical signals in FIG. 5A.

FIG. 5A shows a perspective view of a polarization transformation configuration 510 realized by the Faraday effect, in accordance with an embodiment of the present disclosure. Polarization transformation configuration 510 is arranged for in-coupling and out-coupling optical signals with coupler 101 and comprises Faraday rotator 501 and an optional polarization rotator 502. FIG. 5B shows a top view of the polarization states of optical signals in FIG. 5A.

In FIG. 5A, Faraday rotator 501 is an optical component disposed between the target and polarization-diversified free-space-to-waveguide coupler 101. Faraday rotator 501 may be configured to rotate a linearly polarized optical signal by an angle (e.g., 45 degrees). As shown in FIG. 5A, for example, coupler 101 may emit optical signal $E_1$ that is linearly polarized along the x direction. Faraday rotator 501 may then rotate the polarization of optical signal $E_1$ by 45 degrees to give rise to optical signal $E_2$ that is linearly polarized along a direction that makes an angle of 45 degrees with respect to the x direction.

In FIG. 5A, optional polarization rotator 502 (herein referred to as polarization rotator for simplicity) is disposed between the target and Faraday rotator 501. Examples of polarization rotator 502 may include but not limited to a quartz rotator. In FIG. 5A, polarization rotator 502 may be configured in such a way that further rotates the polarization of optical signal $E_2$ by an angle. As shown in FIG. 5A, for example, polarization rotator 502 rotates the polarization of optical signal $E_2$, that is linearly polarized along a direction that makes an angle of 45 degrees with respect to the x direction, by 45 degrees to give rise to optical signal $E_3$ that is linearly polarized along the y direction.

Polarization rotator 502 is a reciprocal optical component, that is, the polarization rotation by polarization rotator 502 does not depend on the propagation direction of the optical signal. According to FIG. 5A, polarization rotator 502 may rotate the polarization of an incoming optical signal $E_4$, that has the same linear polarization as $E_3$, by an angle (e.g., 45 degrees) to give rise to optical signal $E_5$ that has the same polarization as $E_2$. In contrast, Faraday rotator 501 is a nonreciprocal optical component. Due to the reversed propagation direction of $E_5$ with respect to $E_2$, Faraday rotator 501 may rotate the polarization of optical signal $E_5$ by an angle (e.g., 45 degrees) to give rise to an optical signal $E_6$ that is linearly polarized along a direction (i.e., y direction according to FIG. 5A) orthogonal to the polarization of the optical signal $E_1$. According to some embodiments, the angular rotation effected by Faraday rotator 501 may not be sensitive to the incident angle of the optical signal onto Faraday rotator 501, as the effects of the length of the propagation path of the optical signal inside Faraday rotator 501 and the magnetic field strength along the propagation path on polarization rotation may compensate each other. The operation principle of a Faraday rotator is well-known to those skilled in the art.

According to some embodiments, optional polarization rotator 502 may be used to transform the polarization of $E_3$ to one of the polarization basis components defined by coupler 101. As an example, the polarization basis defined by coupler 101 in FIG. 5A are the linear polarizations along the x and y directions. According to other embodiments, optional polarization rotator 502, which may be a quartz rotator, may be used to enable a broadband polarization rotation when using together with Faraday rotator 501. Conventional polarization rotators such as quartz rotators are sensitive to the incident angle of the incident optical signal. According to some embodiments, polarization rotator 502 may be a polarization rotator that may accept incident optical signal with a large angular range while the intended phase shift may be maintained. Examples of such a wide-angle polarization rotator include but not limited to artificial photonic structures designed with the field transformation approach as described in "A Wide-angle Multi-Octave Broadband Waveplate Based on Field Transformation Approach," Scientific Reports, 5, 17532 (2015).

According to some embodiments, the components of polarization transformation configuration 510 may exhibit as separate components as illustrated in FIG. 5A. According to other embodiments, some or all components of polarization transformation configuration 510 may exhibit as a single combined component. Additionally, according to some embodiments, polarization transformation configuration 510 may be an optical assembly that is separate from the PIC chip comprising polarization-diversified free-space-to-wave guide coupler 101 as illustrated in FIG. 5A. According to other embodiments, some or all components of polarization transformation configuration 510 may be attached to the surface of the PIC chip comprising coupler 101. According to further embodiments, some or all components of polarization transformation configuration 510 may be within or be part of the PIC chip comprising coupler 101.

In FIG. 5A, for illustrative purpose, the propagation path of in-coupling optical signals $E_1$, $E_2$, and $E_3$ and the propagation path of out-coupling optical signals $E_4$, $E_5$, and $E_6$ are distinctly drawn. In general, the propagation paths of the in-coupling and out-coupling signals may or may not be spatially distinct. Additionally, in FIG. 5A, for illustrative purpose, optical signals $E_1$, $E_2$, $E_3$, $E_4$, $E_5$ and $E_6$ are depicted to propagate along the z direction and are at normal incident on coupler 101, Faraday rotator 501 and polarization rotator 502. In general, the propagation directions of the optical signals may be at normal incidence or at incident angles other than normal incidence with respect to these components.

Figure 5C:
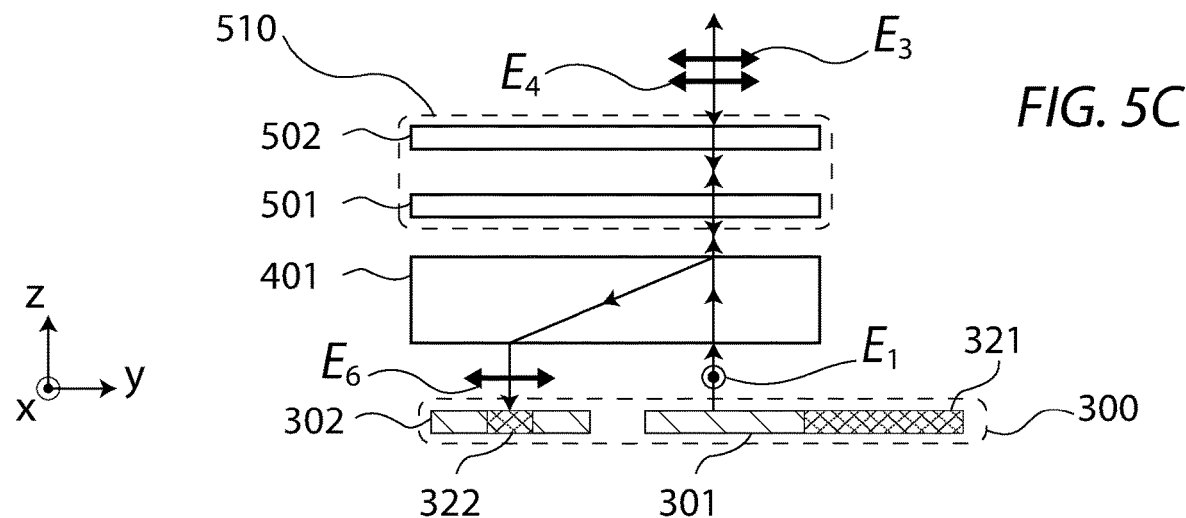
FIG. 5C shows a side view of a polarization transformation-separation configuration incorporating the polarization transformation configuration in FIG. 5A and the polarization-separation configuration in FIG. 4C, in accordance with an embodiment of the present disclosure.

FIG. 5C shows a side view of a polarization transformation-separation configuration for use with coupler 300, in accordance with an embodiment of the present disclosure, wherein the polarization transformation configuration 510 in FIG. 5A is incorporated with the polarization-separation configuration in FIG. 4C. As shown in FIG. 5C, polarization-dependent beam-separator 401 is disposed between coupler 300 (comprising sub-couplers 301 and 302) and polarization transformation configuration 510 (comprising Faraday rotator 501 and polarization rotator 502). Polarization-dependent beam-separator 401 in FIG. 5C may be used to enable optical signals that are coupled with sub-couplers 301 and 302 to propagate along a common optical path, wherein the common optical path lies between polarization-dependent beam-separator 401 and the target. For example, as shown in FIG. 5C, sub-coupler 301 may output optical signal $E_1$ into free space, wherein $E_1$ is linearly polarized along a direction defined by sub-coupler 301 (e.g., the x direction in FIG. 5C). According to FIG. 5C and with reference to FIGS. 4C and 5A, on one hand, optical signal $E_1$ may give rise to optical signal $E_3$ that is linearly polarized along a direction orthogonal to that of $E_1$ (e.g., the y direction). On the other hand, incoming optical signal $E_4$, that has the same polarization as $E_3$ and propagates along a common optical path as the outgoing optical signal $E_3$, but in a reversed direction, through polarization rotator 502, Faraday rotator 501 and polarization-dependent beam-separator 401, may give rise to optical signal $E_6$ that is linearly polarized along a direction orthogonal to the polarization of $E_1$ (i.e., the y direction) and is spatially separated from the path of $E_1$ so that optical signal $E_6$ may couple with sub-coupler 302.

According to some embodiments, the components of polarization transformation configuration 510 and polarization-dependent beam-separator 401 may exhibit as separate components as illustrated in FIG. 5C. According to other embodiments, some or all components of polarization transformation configuration 510 and polarization-dependent beam-separator 401 may exhibit as a single combined component. Additionally, according to some embodiments, polarization transformation configuration 510 and polarization-dependent beam-separator 401 may be an optical assembly that is separate from the PIC chip comprising polarization-diversified free-space-to-waveguide coupler 300 as illustrated in FIG. 5C. According to other embodiments, some or all components of polarization transformation configuration 510 and polarization-dependent beam-separator 401 may be attached to the surface of the PIC chip comprising coupler 300. According to further embodiments, some or all components of polarization transformation configuration 510 and polarization-dependent beam-separator 401 may be within or be part of the PIC chip comprising coupler 300.

In FIG. 5C, for illustrative purpose, optical signals $E_1$, $E_3$, $E_4$, and $E_6$ are depicted to propagate along the z direction and are at normal incident on coupler 300, polarization-dependent beam-separator 401, Faraday rotator 501, and polarization rotator 502. In general, the propagation directions of the optical signals may be at normal incidence or at incident angles other than normal incidence with respect to these components.

Figure 6A:
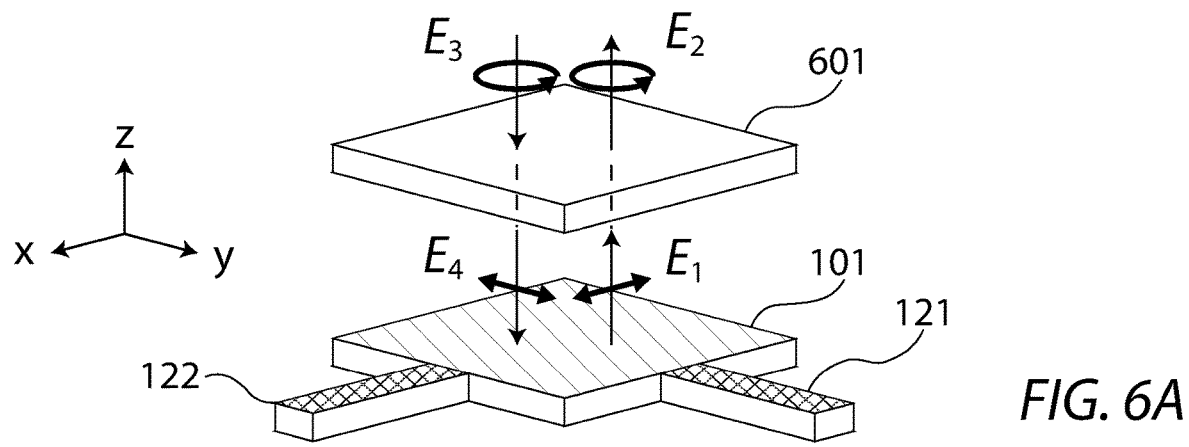
FIG. 6A shows a perspective view of a polarization transformation configuration realized by a quarter-wave plate, in accordance with another embodiment of the present disclosure.
Figure 6B:
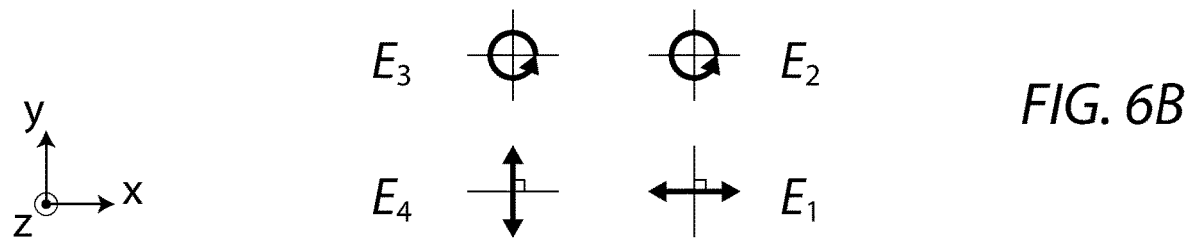
FIG. 6B shows a top view of the polarization states of optical signals in FIG. 6A.

FIG. 6A shows a perspective view of a polarization transformation configuration realized by a quarter-wave plate 601, in accordance with another embodiment of the present disclosure. In this embodiment, the polarization transformation is realized by means of phase retardation through quarter-wave plate. In FIG. 6A, quarter-wave plate 601 is an optical component disposed between the target and polarization-diversified free-space-to-waveguide coupler 101. Quarter-wave plate 601 may be configured, through an appropriate orientation of its optic axis, to transform a linearly polarized optical signal into a circularly polarized optical signal. For example, as shown in FIG. 6A, quarter-wave plate 601 may transform optical signal $E_1$, that is linearly polarized along the x direction, into optical signal $E_2$ that is right-circularly polarized with respect to the propagation direction of $E_2$ (the positive z direction). FIG. 6B shows a top view of the polarization states of optical signals in FIG. 6A.

As shown in FIG. 6A, optical signal $E_3$ has a polarization with the same circular rotation direction as the polarization rotation direction of $E_2$, but propagates in a direction opposite to the propagation direction of $E_2$ (i.e., $E_2$ and $E_3$ effectively have opposite handedness). Quarter-wave plate 601 may be used to transform optical signal $E_3$ to give rise to optical signal $E_4$ that is linearly polarized along a direction orthogonal to the polarization of $E_1$. For example, as shown in FIG. 6A, quarter-wave plate 601 transforms optical signal $E_3$, that is left-circularly polarized with respect to its propagation direction (negative z direction), into optical signal $E_4$ that is linearly polarized along the y direction.

According to some embodiments, quarter-wave plate 601 may be a component that is separate from the PIC chip comprising polarization-diversified free-space-to-waveguide coupler 101 as illustrated in FIG. 6A. According to other embodiments, quarter-wave plate 601 may be attached to the surface of the PIC chip comprising coupler 101. According to further embodiments, quarter-wave plate 601 may be within or be part of the PIC chip comprising coupler 101.

In FIG. 6A, for illustrative purpose, the propagation path of in-coupling optical signals $E_1$ and $E_2$ and the propagation path of out-coupling optical signals $E_3$ and $E_4$ are distinctly drawn. In general, the propagation paths of the in-coupling and out-coupling signals may or may not be spatially distinct. Additionally, in FIG. 6A, for illustrative purpose, optical signals $E_1$, $E_2$, $E_3$, and $E_4$ are depicted to propagate along the z direction and are at normal incident on coupler 101 and quarter-wave plate 601. In general, the propagation directions of the optical signals may be at normal incidence or at incident angles other than normal incidence with respect to these components.

Figure 6C:
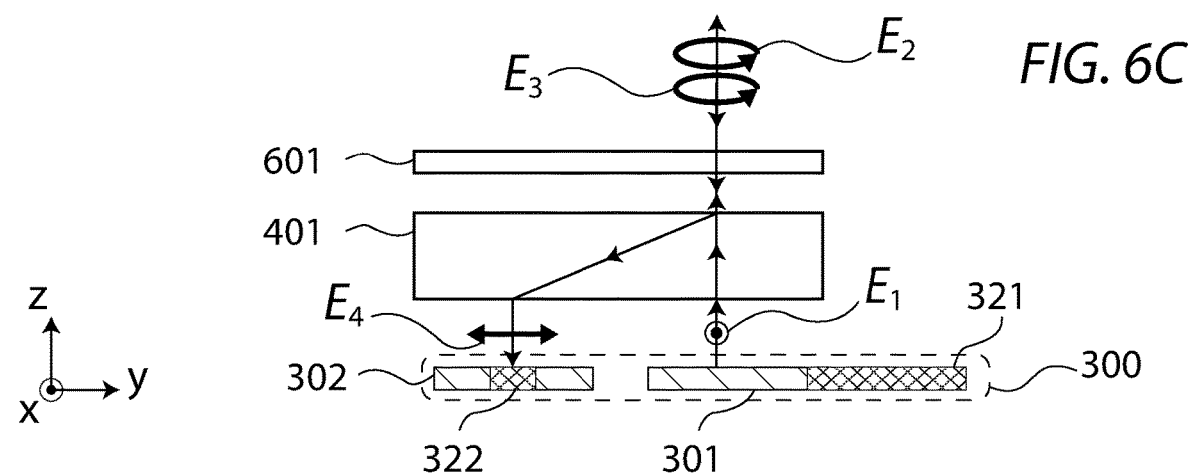
FIG. 6C shows a side view of a polarization transformation-separation configuration incorporating the polarization transformation configuration in FIG. 6A and the polarization-separation configuration in FIG. 4C, in accordance with another embodiment of the present disclosure.

FIG. 6C shows a side view of a polarization transformation-separation configuration for use with coupler 300, in accordance with another embodiment of the present disclosure, wherein the polarization transformation configuration in FIG. 6A is incorporated with the polarization-separation configuration in FIG. 4C. As shown in FIG. 6C, polarization-dependent beam-separator 401 is disposed between coupler 300 (comprising sub-couplers 301 and 302) and quarter-wave plate 601. Polarization-dependent beam-separator 401 in FIG. 6C may be used to enable optical signals that are coupled with sub-couplers 301 and 302 to propagate along a common optical path, wherein the common optical path lies between polarization-dependent beam-separator 401 and the target. For example, as shown in FIG. 6C, sub-coupler 301 may output optical signal $E_1$ into free space, wherein $E_1$ is linearly polarized along a direction defined by the design of sub-coupler 301 (e.g., the x direction in FIG. 6C). According to FIG. 6C and with reference to FIGS. 4C and 6A, on one hand, optical signal $E_1$ may give rise to optical signal $E_2$ that is right-circularly polarized with respect to the propagation direction of $E_2$ (e.g., along the positive z direction). On the other hand, incoming optical signal $E_3$ has a polarization with the same circular rotation direction as the polarization rotation direction of $E_2$ and propagates along a common optical path as the outgoing optical signal $E_2$, but in a reversed direction (i.e., $E_3$ is left-circularly polarized with respect to its propagation direction). Incoming optical signal $E_3$, through quarter-wave plate 601 and polarization-dependent beam-separator 401, may give rise to optical signal $E_4$ that is linearly polarized along a direction orthogonal to the polarization of $E_1$ (e.g., the y direction in FIG. 6C) and is spatially separated from the path of $E_1$, so that optical signal $E_4$ may couple with sub-coupler 302.

According to some embodiments, quarter-wave plate 601 and polarization-dependent beam-separator 401 may exhibit as separate components as illustrated in FIG. 6C. According to other embodiments, quarter-wave plate 601 and polarization-dependent beam-separator 401 may exhibit as a single combined component. Additionally, according to some embodiments, quarter-wave plate 601 and polarization-dependent beam-separator 401 may be an optical assembly that is separate from the PIC chip comprising polarization-diversified free-space-to-waveguide coupler 300 as illustrated in FIG. 6C. According to other embodiments, either one or both of quarter-wave plate 601 and polarization-dependent beam-separator 401 may be attached to the surface of the PIC chip comprising coupler 300. According to further embodiments, either one or both of quarter-wave plate 601 and polarization-dependent beam-separator 401 may be within or be part of the PIC chip comprising coupler 300.

In FIG. 6C, for illustrative purpose, optical signals $E_1$, $E_2$, $E_3$, and $E_4$ are depicted to propagate along the z direction and are at normal incident on coupler 300, polarization-dependent beam-separator 401 and quarter-wave plate 601. In general, the propagation directions of the optical signals may be at normal incidence or at incident angles other than normal incidence with respect to these components.

In some applications of optical coherent sensing, the target may reflect or scatter the optical signal that illuminates the target, in such a way that the returning optical signal is polarized with a polarization substantially different from the polarization of the illuminating optical signal. To optimize the signal received, it may be desirable for a coherent sensing unit to be able to detect incoming optical signals with any polarization states.

Figure 7A:
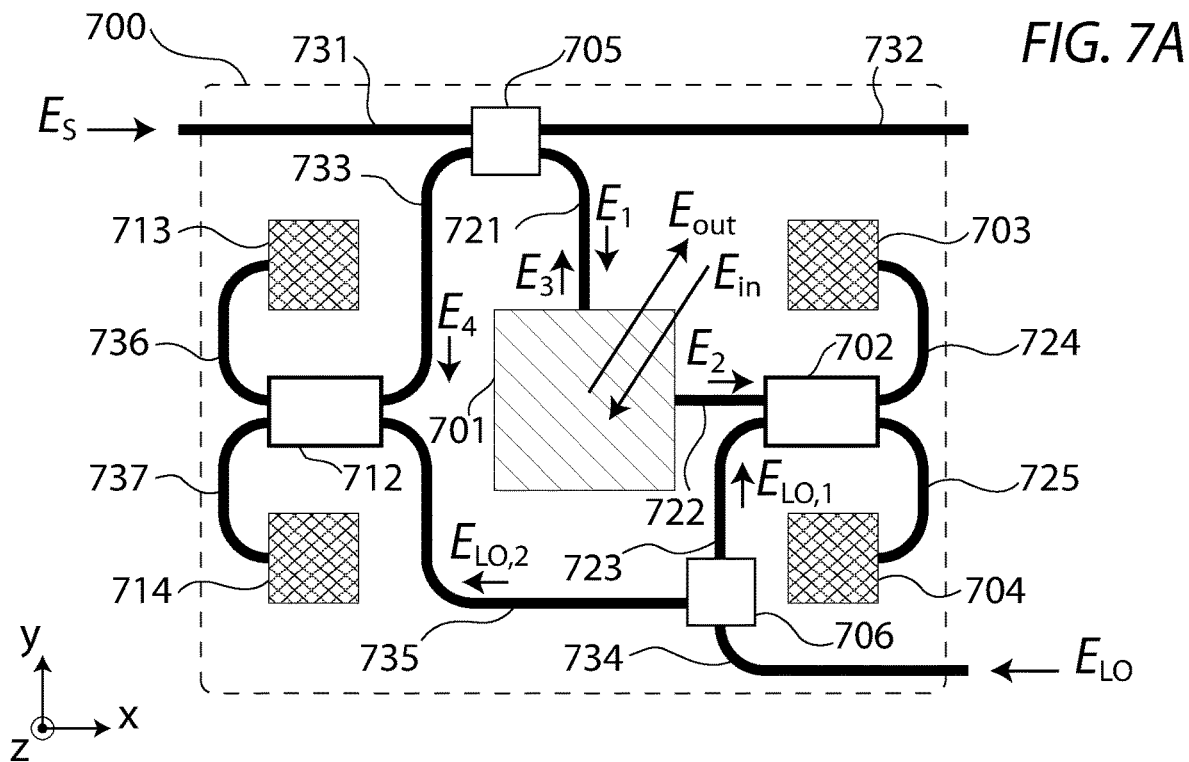
FIG. 7A shows a plan view of a coherent sensing unit for transmitting and receiving optical signals based on polarization diversity, in accordance with another embodiment of the present disclosure.

FIG. 7A shows a plan view of a coherent sensing unit 700 for transmitting and receiving optical signals based on polarization diversity, in accordance with another embodiment of the present disclosure. Coherent sensing unit 700 in FIG. 7A is similar to coherent sensing unit 100 in FIG. 1A. The primary difference between coherent sensing unit 700 and coherent sensing unit 100 is that coherent sensing unit 700 may also process the component of the incoming optical signal $E_{in}$ that is coupled by coupler 101 and directed to waveguide 121 according to the embodiment of coherent sensing unit 100 in FIG. 1A.

More specifically, referring to FIG. 7A, optical source signal $E_S$ is supplied to coherent sensing unit 700 through waveguide 731 and local oscillator (LO) $E_{LO}$ is supplied to coherent sensing unit 700 through waveguide 734. In FIG. 7A, component 705 is a 2×2 optical coupler. Since there is no signal input from waveguide 733, 2×2 optical coupler 705 may function as a splitting coupler that splits the optical source signal $E_S$ from waveguide 731 and directs a fraction of $E_S$ as an optical signal Et through waveguide 721 into polarization-diversified free-space-to-waveguide coupler 701. A fraction of $E_S$ may also pass to waveguide 732. The fraction of $E_S$ passed into waveguide 732 may be used for other purposes (for example, as in coherent sensing unit 710 in FIG. 7B) or may simply be regarded as a loss. For the latter situation, the fraction of $E_S$ passed to waveguide 732 may need to be attenuated properly to avoid any back reflection. The fractions of $E_S$ that are passed to waveguides 721 and 732 respectively depend on the splitting ratio and loss of 2×2 optical coupler 705. According to some embodiments, 2×2 optical coupler 705 may be a 50/50 2×2 optical coupler. According to other embodiments, 2×2 optical coupler 705 may have a splitting ratio other than 50/50.

In FIG. 7A, polarization-diversified free-space-to-waveguide coupler 701 (herein referred to as coupler 701 for simplicity) is similar to coupler 101 of coherent sensing unit 100 in FIG. 1A that functions as both a transmitter and a receiver. It is a two-waveguide coupler that is connected to waveguides 721 and 722.

As a transmitter, with reference to FIG. 7A, coupler 701 may couple optical signal Et from waveguide 721 into free space as an outgoing optical signal $E_{out}$, which may be used for target illumination by the optical coherent imager. The outgoing optical signal $E_{out}$ output by coupler 701 propagates in a direction that is out of the x-y plane (i.e., the propagation direction of $E_{out}$ has a nonzero z component) and is polarized with a polarization defined by the design of coupler 701.

As a receiver, with reference to FIG. 7A, coupler 701 may couple an incoming optical signal $E_{in}$ into coherent sensing unit 700. The incoming optical signal $E_{in}$ coupled by coupler 701 may be directed to either or both waveguides 721 and 722, depending on the polarization state of the incoming optical signal $E_{in}$. The polarization components of the incoming optical signal $E_{in}$ that are coupled to waveguides 721 and 722 depend on the design of coupler 701. According to some embodiments, the polarization component of incoming optical signal $E_{in}$ that is orthogonal to the polarization of outgoing optical signal $E_{out}$ may be directed to waveguide 722 as an in-coupled optical signal $E_2$, and the polarization component of the incoming optical signal $E_{in}$ that is orthogonal to the polarization component of the incoming optical signal $E_{in}$ directed to waveguide 722 may be directed to waveguide 721 as an in-coupled optical signal $E_3$. The in-coupled optical signal $E_3$ propagates in a direction opposite to the propagation direction of optical signal $E_1$. Since there is no signal input from waveguide 732, 2×2 optical coupler 705 may function as a splitting coupler that splits the in-coupled optical signal $E_3$ from waveguide 721 and directs a fraction of $E_3$ as an optical signal $E_4$ through waveguide 733 into 2×2 optical coupler 712. A fraction of $E_3$ may also pass to waveguide 731 and propagate in a direction opposite to the propagation direction of optical source signal $E_S$. According to some embodiments, the component of $E_3$ in waveguide 731 may be left unattended without affecting the other parts of the PIC chip comprising the sensing unit 700. The fractions of $E_3$ that are passed respectively to waveguides 731 and 733 depend on the splitting ratio and loss of 2×2 optical coupler 705.

In FIG. 7A, although coupler 701 is drawn as a single entity, coupler 701 in general may comprise a single photonic component or multiple photonic components. According to some embodiments, similar to coupler 101 as illustrated in FIGS. 1A and 1B, coupler 701 may be realized by a polarization-splitting free-space-to-waveguide coupler. According to other embodiments, coupler 701 may be realized by coupler 200 in FIG. 2, wherein waveguides 221 and 222 may be the same as waveguides 721 and 722 (i.e., waveguide 721 being waveguide 221 and waveguide 722 being waveguide 222, or waveguide 721 being waveguide 222 and waveguide 722 being waveguide 221). According to further embodiments, coupler 701 may be realized by coupler 300 in FIG. 3, wherein waveguides 321 and 322 may be the same as waveguides 721 and 722 (i.e., waveguide 721 being waveguide 321 and waveguide 722 being waveguide 322, or waveguide 721 being waveguide 322 and waveguide 722 being waveguide 321). According to yet further embodiments wherein coupler 701 is realized by coupler 300, polarization-dependent beam-separator 401 in FIG. 4C may be used with coherent sensing unit 700 to enable outgoing optical signal $E_{out}$ and incoming optical signal $E_{in}$ to propagate along a common optical path, wherein the common optical path lies between polarization-dependent beam-separator 401 and the target. According to some embodiments, similar to coupler 101 in FIGS. 1A and 1B, coupler 701 may also comprise any of TE-TM mode converters, splitters, and combiners.

Additionally, according to some embodiments, Faraday rotator 501 and optional polarization rotator 502 illustrated in FIGS. 5A and 5C may be used with coupler 701, to rotate the polarizations of the outgoing and incoming optical signals. According to some embodiments, quarter-wave plate 601 illustrated in FIGS. 6A and 6C may be used with coupler 701 to transform the outgoing optical signal into a linearly-polarized, circularly-polarized or elliptically-polarized optical signal, depending on the polarization of the outgoing optical signal.

In FIG. 7A, component 706 is a splitting coupler that splits the LO from waveguide 734 and directs a fraction of the LO to waveguide 723 as the LO $E_{LO,1}$ and a fraction of the LO to waveguide 735 as the LO $E_{LO,2}$. The fractions of the LO that are passed respectively to waveguides 723 and 735 depend on the splitting ratio and loss of splitting coupler 706. According to some embodiments, splitting coupler 706 may be a 50/50 splitting coupler. According to other embodiments, splitting coupler 706 may have a splitting ratio other than 50/50.

In FIG. 7A, component 702 is a 2×2 optical coupler that mixes the in-coupled optical signal $E_2$ from waveguide 722 and the LO $E_{LO,1}$ from waveguide 723, and splits and directs the mixed signal to waveguides 724 and 725. According to some embodiments, 2×2 optical coupler 702 may be similar to 2×2 optical coupler 102 of coherent sensing unit 100 in FIG. 1.

In FIG. 7A, component 703 is a square-law photodetector that receives and detects the optical signal from waveguide 724. Similarly, in FIG. 7A, component 704 is a square-law photodetector that receives and detects the optical signal from waveguide 725. According to some embodiments, photodetectors 703 and 704 may be similar to photodetectors 103 and 104 of coherent sensing unit 100 in FIG. 1.

According to some embodiments, photodetectors 703 and 704 may be connected to an output electronic circuit comprising electronic components, such as, but not limited to, any one or more of transimpedance amplifiers (TIA), transistors, diodes, resistors, capacitors, and electrical switches, that are used to process the electrical outputs of photodetectors 703 and 704. This output electronic circuit is not shown in FIG. 7A.

In FIG. 7A, component 712 is a 2×2 optical coupler that mixes the in-coupled signal $E_4$ from waveguide 733 and the LO $E_{LO,2}$ from waveguide 735, and splits and directs the mixed signal to waveguides 736 and 737.

In FIG. 7A, component 713 is a square-law photodetector that receives and detects the optical signal from waveguide 736. Similarly, in FIG. 7A, component 714 is a square-law photodetector that receives and detects the optical signal from waveguide 737. According to some embodiments, photodetectors 713 and 714 may be similar to photodetectors 703 and 704.

According to some embodiments, photodetectors 713 and 714 may be connected to an output electronic circuit comprising electronic components, such as, but not limited to, any one or more of transimpedance amplifiers (TIA), transistors, diodes, resistors, capacitors, and electrical switches, that are used to process the electrical outputs of photodetectors 713 and 714. This output electronic circuit is not shown in FIG. 7A. According to some embodiments, the output electronic circuit connected to photodetectors 713 and 714 may form a single electronic circuit with the output electronic circuit connected to photodetectors 703 and 704. According to other embodiments, the output electronic circuit connected to photodetectors 713 and 714 may be separate from the output electronic circuit connected to photodetectors 703 and 704.

According to some embodiments, coherent sensing unit 700 may comprise components not explicitly shown, including but not limited to any one or more of electro-optical components and thermo-optical components, for any one or more of phase, amplitude, frequency, wavelength, and temporal controls.

Figure 7B:
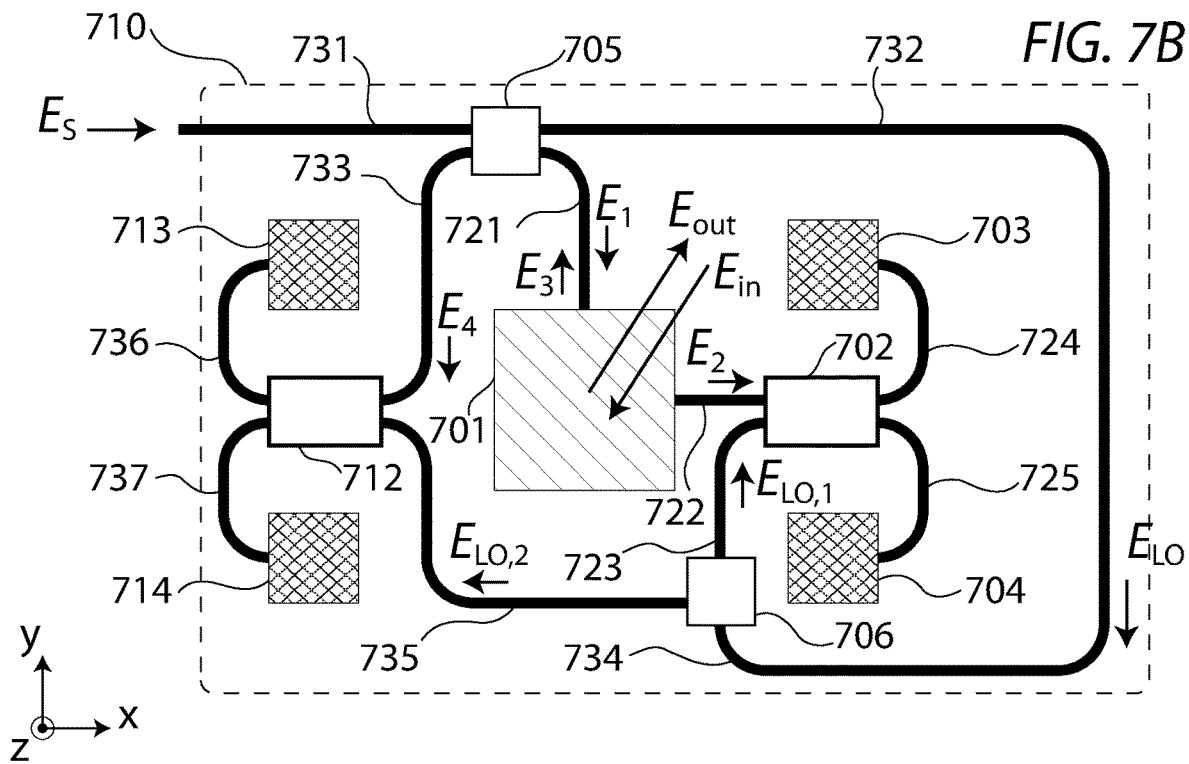
FIG. 7B shows a plan view of a coherent sensing unit for transmitting and receiving optical signals based on polarization diversity, in accordance with yet another embodiment of the present disclosure.

FIG. 7B shows a plan view of a coherent sensing unit 710 for transmitting and receiving optical signals based on polarization diversity, in accordance with yet another embodiment of the present disclosure. Coherent sensing unit 710 in FIG. 7B is similar to coherent sensing unit 700 in FIG. 7A. The primary difference between coherent sensing unit 700 and coherent sensing unit 710 is that, in coherent sensing unit 710, waveguide 734 is connected to waveguide 732 so that the LO $E_{LO}$ comes from a fraction of optical source signal $E_S$ that is passed into waveguide 732.

Figure 8:
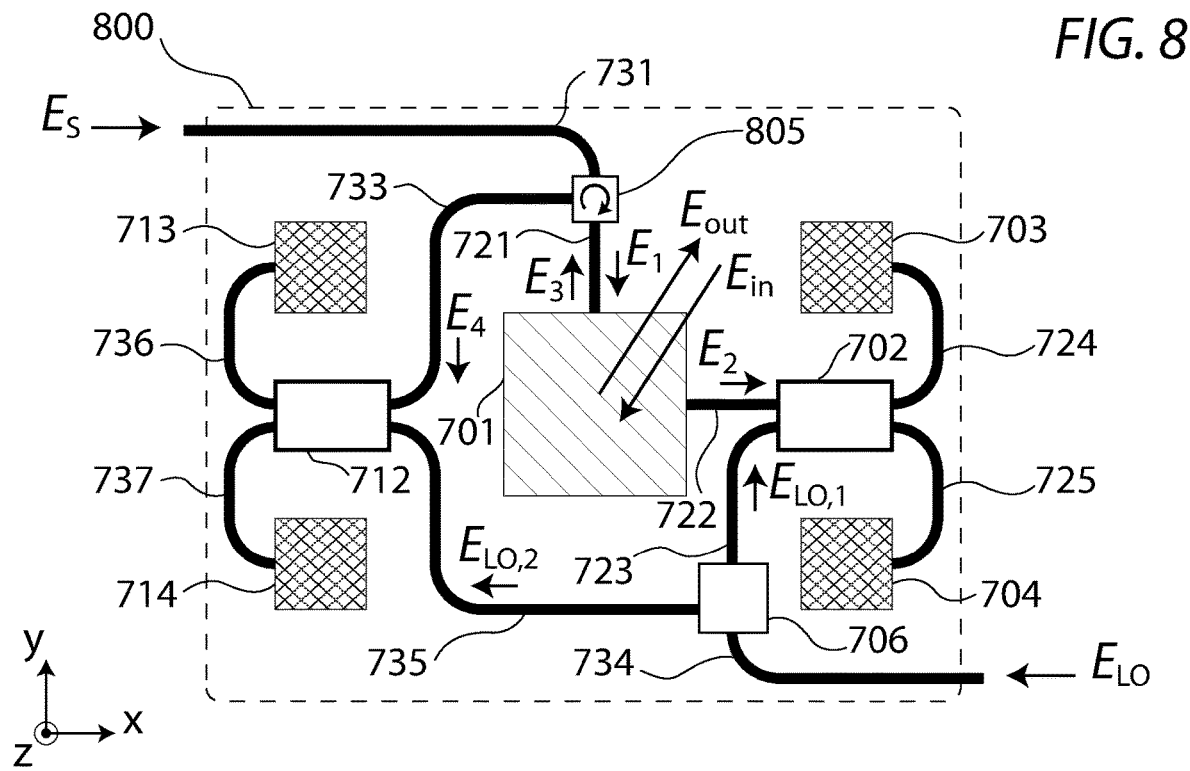
FIG. 8 shows a plan view of a coherent sensing unit for transmitting and receiving optical signals based on polarization diversity, in accordance with a further embodiment of the present disclosure.

FIG. 8 shows a plan view of a coherent sensing unit 800 for transmitting and receiving optical signals based on polarization diversity, in accordance with a further embodiment of the present disclosure. Coherent sensing unit 800 in FIG. 8 is similar to coherent sensing unit 700 in FIG. 7A. The primary difference between coherent sensing unit 800 and coherent sensing unit 700 is that an optical circulator 805 is used in coherent sensing unit 800 to replace 2×2 optical coupler 705 in coherent sensing unit 700 to direct the flow of optical signals. Examples of optical circulator 805 may include but not limited to an optical circulator based on heterogeneous Ce:YIG/silicon waveguides in a Mach-Zehnder interferometer (MZI) configuration as described in "Broadband TE Optical Isolators and Circulators in Silicon Photonics Through Ce:YIG Bonding," Journal of Lightwave Technology, Vol. 37, No. 5, p. 1463 (2019).

According to the embodiment in FIG. 8, optical circulator 805 is a three-port optical circulator that routes optical signals in a circular direction. More specifically, optical circulator 805 may route optical signals in a clockwise direction: optical signal inputting from waveguide 731 is directed to waveguide 721, optical signal inputting from waveguide 721 is directed to waveguide 733, and optical signal inputting from waveguide 733 is directed to waveguide 731.

In FIG. 8, optical circulator 805 couples with waveguides 721, 731, and 733. Waveguide 732 of coherent sensing unit 700 in FIG. 7 may then be omitted from coherent sensing unit 800 in FIG. 8. Optical circulator 805 may route the optical source signal $E_S$ in waveguide 731 to give rise to optical signal $E_1$ in waveguide 721. In-coupled optical signal $E_3$ received by coupler 701 may be directed through waveguide 721 to optical circulator 805, where optical circulator 805 may route the in-coupled optical signal $E_3$ to waveguide 733 to give rise to the optical signal $E_4$.

According to some embodiments, a four-port optical circulator, such as one realized by a four-port MZI-based optical circulator, may be used instead of a three-port optical circulator for optical circulator 805, and waveguide 732 of coherent sensing unit 700 in FIG. 7 may be retained in coherent sensing unit 800 in FIG. 8. In such a circumstance, the four-port optical circulator may be coupled to waveguides 721, 731, 732, and 733, wherein the four-port optical circulator routes optical signals from waveguide 731 to waveguide 721, from waveguide 721 to waveguide 733, from waveguide 733 to waveguide 732, and from waveguide 732 to waveguide 731.

In FIG. 8, the use of optical circulator 805 in coherent sensing unit 800 to replace 2×2 optical coupler 705 in coherent sensing unit 700, ideally, may have the advantage of avoiding the loss of a fraction of optical source signal $E_S$ that is passed into waveguide 732. Nevertheless, current state-of-the-art on-chip optical circulator has an insertion loss (>10 dB) that may still be too high to impose an advantage over the use of 2×2 optical coupler 705 in the configuration of coherent sensing unit 700.

Figure 9:
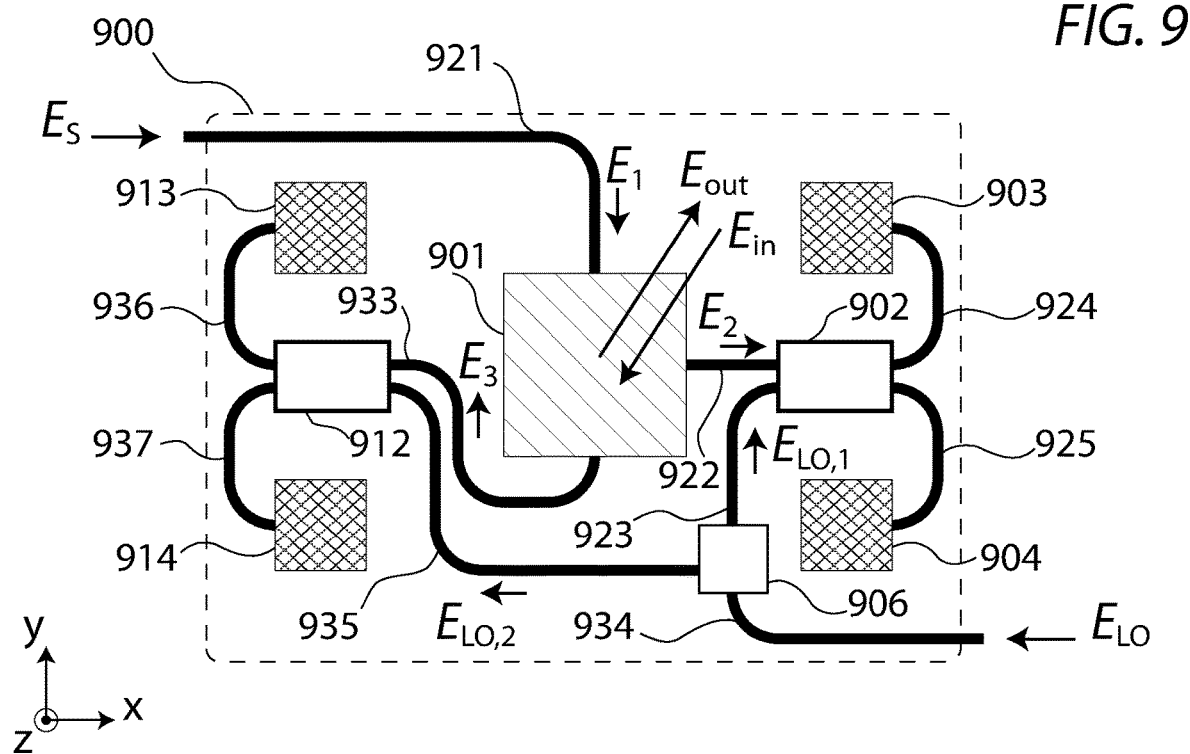
FIG. 9 shows a plan view of a coherent sensing unit for transmitting and receiving optical signals based on polarization diversity, in accordance with a yet further embodiment of the present disclosure.

FIG. 9 shows a plan view of a coherent sensing unit 900 for transmitting and receiving optical signals based on polarization diversity, in accordance with a yet further embodiment of the present disclosure. Coherent sensing unit 900 is similar to coherent sensing units 700, 710, and 800 that detect an incoming optical signal with any polarization state. The primary difference between coherent sensing unit 900 and coherent sensing units 100, 700, 710, and 800 is that coherent sensing unit 900 comprises a polarization-diversified free-space-to-waveguide coupler that directs in-coupled optical signals with any polarization states to waveguides that are distinct from the waveguide carrying an outgoing optical signal.

More specifically, referring to FIG. 9, optical source signal $E_S$ is supplied to coherent sensing unit 900 through waveguide 921 and local oscillator (LO) $E_{LO}$ is supplied to coherent sensing unit 900 through waveguide 934.

In FIG. 9, polarization-diversified free-space-to-waveguide coupler 901 (herein referred to as coupler 901 for simplicity) is a three-waveguide coupler that is connected to waveguides 921, 922, and 933. Coupler 901 may function as both a transmitter and a receiver.

As a transmitter, with reference to FIG. 9, coupler 901 may couple outgoing optical signal $E_1$ (which is essentially the same as the optical source signal $E_S$) from waveguide 921 into free space as an outgoing optical signal $E_{out}$, which may be used for target illumination by the optical coherent imager. Outgoing optical signal $E_{out}$ output by coupler 901 propagates in a direction that is out of the x-y plane (i.e., the propagation direction of $E_{out}$ has a nonzero component) and is polarized with a polarization state defined by the design of coupler 901.

As a receiver, coupler 901 may couple an incoming optical signal $E_{in}$ into coherent sensing unit 900. Incoming optical signal $E_{in}$ coupled by coupler 901 may be directed to either or both waveguides 922 and 933, depending on the polarization state of incoming optical signal $E_{in}$. The polarization components of the incoming optical signal $E_{in}$ that are coupled to waveguides 922 and 933 depend on the design of coupler 901. According to some embodiments, the polarization component of incoming optical signal $E_{in}$ that is orthogonal to the polarization of the outgoing optical signal $E_{out}$ may be directed to waveguide 922 as an in-coupled optical signal $E_2$, and the polarization component of incoming optical signal $E_{in}$ that is orthogonal to the polarization component of incoming optical signal $E_{in}$ directed to waveguide 922 may be directed to waveguide 933 as an in-coupled optical signal $E_3$.

Figure 10A:
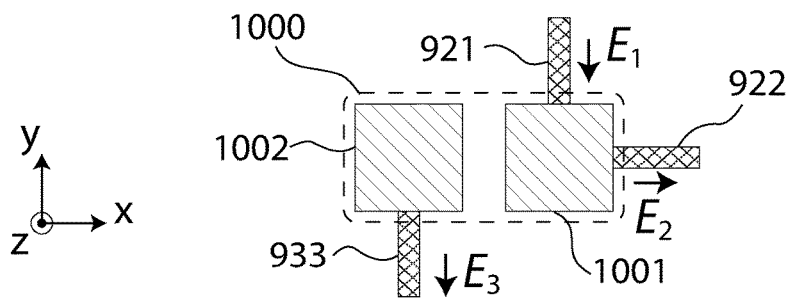
FIG. 10A shows a top view of a three-waveguide polarization-diversified free-space-to-wave guide coupler, in accordance with an embodiment of the present disclosure.
Figure 11A:
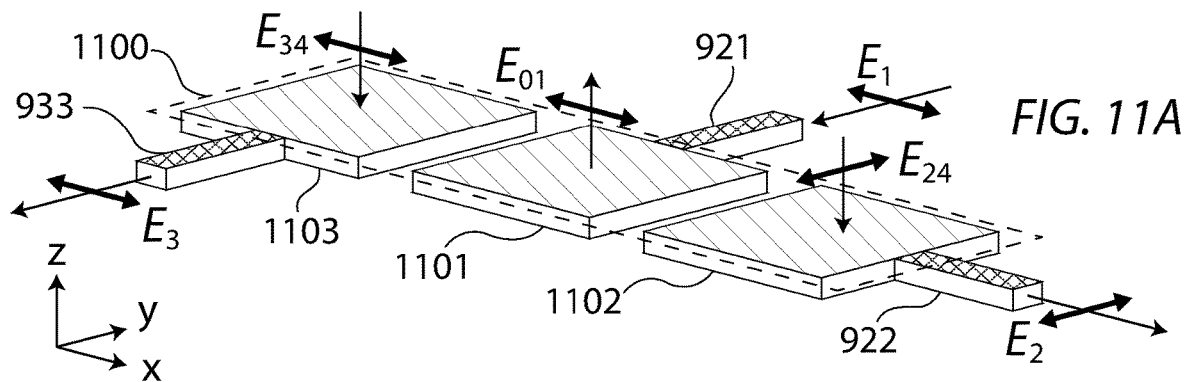
FIG. 11A shows a perspective view of a three-waveguide polarization-diversified free-space-to-waveguide coupler, in accordance with another embodiment of the present disclosure.
Figure 13A:
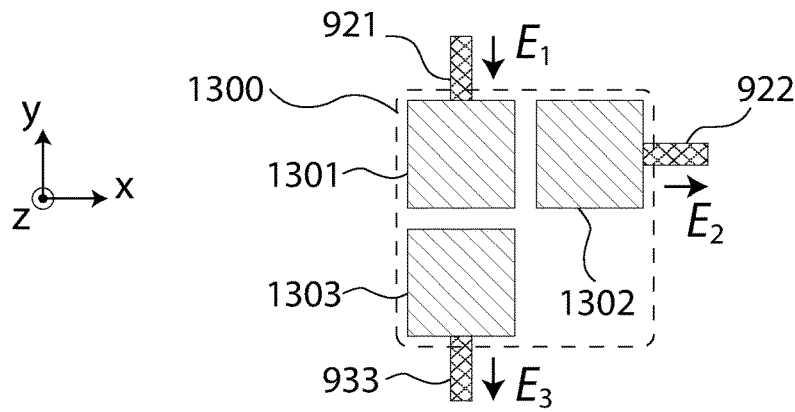
FIG. 13A shows a top view of a three-waveguide polarization-diversified free-space-to-waveguide coupler, in accordance with a further embodiment of the present disclosure.

In FIG. 9, although coupler 901 is drawn as a single entity, coupler 901 in general may comprise a single photonic component or multiple photonic components. Embodiments of coupler 901 are illustrated in FIGS. 10A, 11A, and 13A to be described in further detail below. According to some embodiments, similar to coupler 101 in FIGS. 1A and 1B, coupler 901 may also comprise any of TE-TM mode converters, splitters, and combiners.

In FIG. 9, splitting coupler 906 splits the LO $E_{LO}$ from waveguide 934 and directs a fraction of the LO to waveguide 923 as the LO $E_{LO,1}$ and a fraction of the LO to waveguide 935 as the LO $E_{LO,2}$. The fractions of the LO that are passed respectively to waveguides 923 and 935 depend on the splitting ratio and loss of splitting coupler 906. According to some embodiments, splitting coupler 906 may be a 50/50 splitting coupler. According to other embodiments, splitting coupler 906 may have a splitting ratio other than 50/50.

In FIG. 9, component 902 is a 2×2 optical coupler that mixes the in-coupled optical signal $E_2$ from waveguide 922 and the LO $E_{LO,1}$ from waveguide 923, and splits and directs the mixed signal to waveguides 924 and 925. According to some embodiments, 2×2 optical coupler 902 may be similar to 2×2 optical coupler 702 of coherent sensing unit 700 in FIG. 7A.

In FIG. 9, component 903 is a square-law photodetector that receives and detects the optical signal from waveguide 924. Similarly, in FIG. 9, component 904 is a square-law photodetector that receives and detects the optical signal from waveguide 925. According to some embodiments, photodetectors 903 and 904 may be similar to photodetectors 703 and 704 of coherent sensing unit 700 in FIG. 7A.

In FIG. 9, similar to 2×2 optical coupler 712 of coherent sensing unit 700 in FIG. 7A, component 912 is a 2×2 optical coupler that mixes the in-coupled optical signal $E_3$ from waveguide 933 and the LO $E_{LO,2}$ from waveguide 935, and splits and directs the mixed signal to waveguides 936 and 937.

In FIG. 9, component 913 is a square-law photodetector that receives and detects the optical signal from waveguide 936. Similarly, in FIG. 9, component 914 is a square-law photodetector that receives and detects the optical signal from waveguide 937. According to some embodiments, photodetectors 913 and 914 may be similar to photodetectors 713 and 714 of coherent sensing unit 700 in FIG. 7A.

Figure 10B:
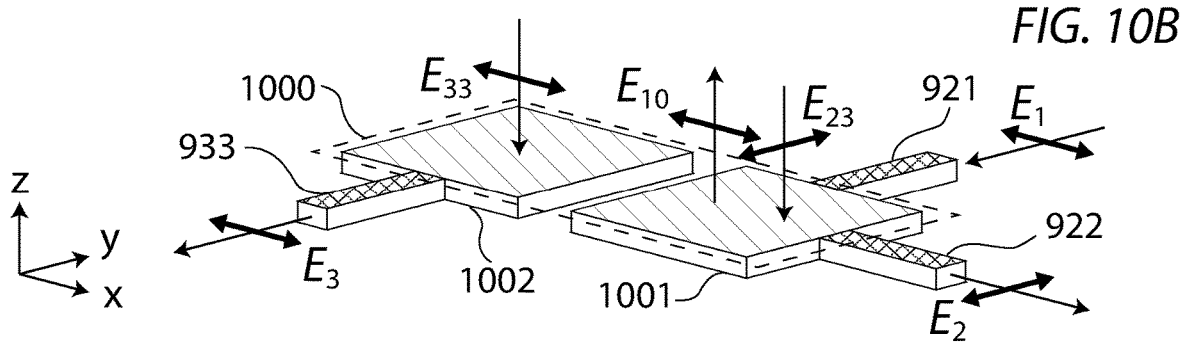
FIG. 10B shows a perspective view of the coupler illustrated in FIG. 10A.

FIG. 10A shows a top view of a three-waveguide polarization-diversified free-space-to-waveguide coupler 1000, in accordance with an embodiment of the present disclosure. FIG. 10B shows a perspective view of coupler 1000 illustrated in FIG. 10A. FIG. 10B additionally shows polarized outgoing and incoming optical signals $E_{10}$, $E_{23}$, and $E_{33}$ coupling with sub-couplers 1001 and 1002. Coupler 1000, as indicated by the dash line in FIG. 10A, comprises two sub-couplers 1001 and 1002. According to some embodiments, sub-coupler 1001 may be realized by either polarization-diversified free-space-to-waveguide coupler 101 as illustrated in FIG. 1B or polarization-diversified free-space-to-waveguide coupler 200 as illustrated in FIG. 2, whereas sub-coupler 1002 may be realized by a free-space-to-waveguide coupler, including but not limited to a grating coupler, that is coupled to a single waveguide. According to other embodiments, sub-coupler 1002 may be realized by a polarization-independent free-space-to-waveguide coupler.

With reference to FIG. 10A, on one hand, waveguide 921 is connected to sub-coupler 1001 as an out-coupling waveguide and waveguide 922 is connected to sub-coupler 1001 as a first in-coupling waveguide. On the other hand, waveguide 933 is connected to sub-coupler 1002 as a second in-coupling waveguide. Here waveguides 921, 922, and 933 are the same waveguides 921, 922, and 933 of coherent sensing unit 900 as illustrated in FIG. 9.

As shown in FIGS. 10A and 10B, one primary function of sub-coupler 1001 is to act as a transmitter to out-couple an optical signal for target illumination. Optical signal $E_1$ in waveguide 921 may be out-coupled by sub-coupler 1001 into free space as an outgoing optical signal $E_{10}$. Similar to coupler 101 in FIG. 1B, outgoing optical signal $E_{10}$ is polarized according to the design of sub-coupler 1001. For example, as shown in FIG. 10B, optical signal $E_{10}$ is linearly polarized along the x direction.

As shown in FIGS. 10A and 10B, another primary function of sub-coupler 1001 is to act as a receiver to in-couple an incoming optical signal into coherent sensing unit 900, wherein the polarization state of the incoming optical signal is orthogonal to the polarization of the outgoing optical signal. An incoming optical signal $E_{23}$ that has a polarization orthogonal to outgoing optical signal $E_{10}$ is in-coupled by sub-coupler 1001 to give rise to in-coupled optical signal $E_2$ in waveguide 922. Similar to coupler 101 in FIG. 1, the polarization of incoming optical signal $E_{23}$ that is optimally in-coupled by sub-coupler 1001 is determined according to the design of sub-coupler 1001. For example, as shown in FIG. 10B, optical signal $E_{23}$ that is optimally in-coupled is linearly polarized along the y direction.

As shown in FIGS. 10A and 10B, a primary function of sub-coupler 1002 is to act as a receiver to in-couple an incoming optical signal into coherent sensing unit 900, wherein the polarization state of the incoming optical signal is orthogonal to the polarization of the incoming optical signal coupled by sub-coupler 1001 into waveguide 922. An incoming optical signal $E_{33}$ that has a polarization orthogonal to that of optical signal $E_{23}$ is in-coupled by sub-coupler 1002 to give rise to the in-coupled optical signal $E_3$ in waveguide 933. Similar to sub-coupler 1001, the polarization of incoming optical signal $E_{33}$ that is optimally in-coupled by sub-coupler 1002 is determined according to the design of sub-coupler 1002. For example, as shown in FIG. 10B, optical signal $E_{33}$ that is optimally in-coupled is linearly polarized along the x direction, which is the same as the polarization of outgoing optical signal $E_{10}$.

Figure 10C:
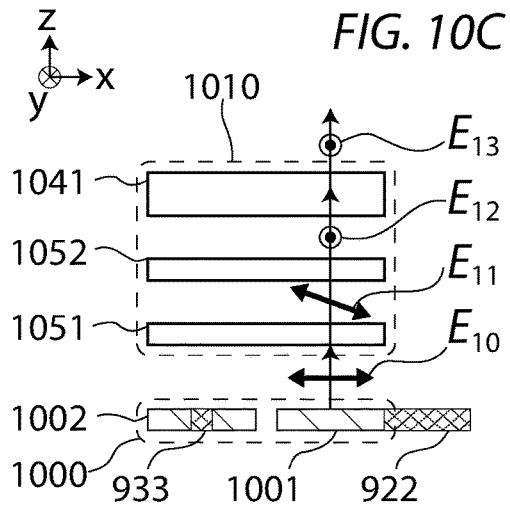
FIG. 10C shows a side view of a polarization transformation-separation configuration for use with a three-waveguide polarization-diversified free-sp ace-to-wave guide coupler for out-coupling optical signals, in accordance with an embodiment of the present disclosure.
Figure 10D:
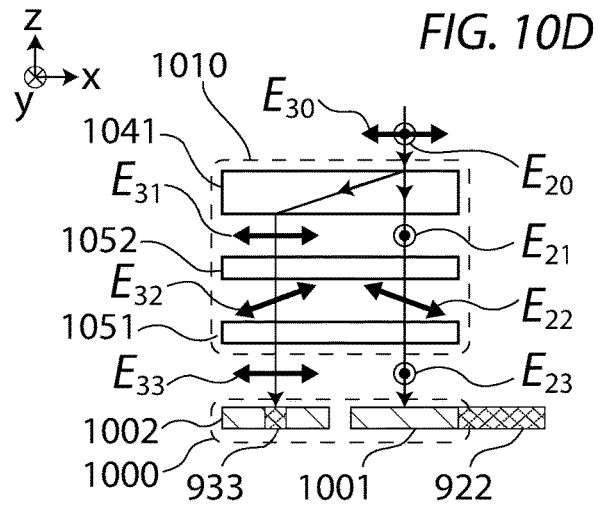
FIG. 10D shows a side view of the configuration illustrated in FIG. 10C used for in-coupling optical signals.
Figure 10E:
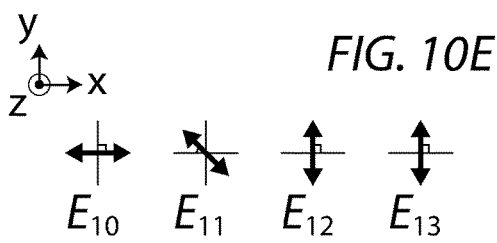
FIG. 10E shows a top view of the polarization states of the optical signals in FIG. 10C.
Figure 10F:
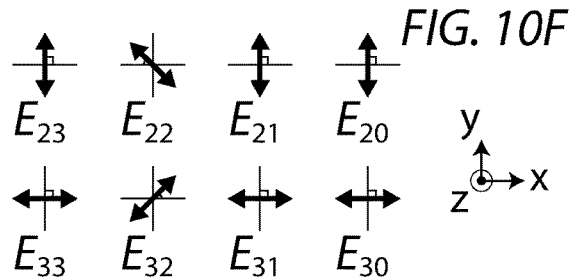
FIG. 10F shows a top view of the polarization states of the optical signals in FIG. 10D.

FIG. 10C shows a side view of a polarization transformation-separation configuration 1010 for use with a three-waveguide polarization-diversified free-space-to-waveguide coupler for out-coupling optical signals, in accordance with an embodiment of the present disclosure. FIG. 10D shows a side view of configuration 1010 illustrated in FIG. 10C used for in-coupling optical signals. Polarization transformation-separation configuration 1010 enables incoming optical signals $E_{23}$ and $E_{33}$ arriving at coupler 1000 and outgoing optical signal $E_{10}$ emitted by coupler 1000 to propagate along a common optical path, wherein the common optical path lies between configuration 1010 and the target. The polarization transformation-separation configuration 1010 comprises Faraday rotator 1051, an optional polarization rotator 1052, and polarization-dependent beam-separator 1041 as illustrated in FIGS. 10C and 10D. For illustrative purpose, FIG. 10E shows a top view of the polarization states of the optical signals in FIG. 10C. Similarly, FIG. 10F shows a top view of the polarization states of the optical signals in FIG. 10D.

For optical signal transmission, as illustrated in FIGS. 10B and 10C, sub-coupler 1001 of coupler 1000 may out-couple optical signal $E_1$ from waveguide 921 to give rise to optical signal $E_{10}$, which is linearly polarized according to the design of sub-coupler 1001 (e.g., linearly polarized along the x direction) and propagates out of sub-coupler 1001 (e.g., towards the positive z direction) into free space. As illustrated in FIGS. 10C and 10E, Faraday rotator 1051 may rotate the polarization of optical signal $E_{10}$ by an angle (e.g., 45 degrees) to give rise to optical signal $E_{11}$ (e.g., $E_{11}$ is linearly polarized along a direction at an angle of 45 degrees with respect to the x direction). Optional polarization rotator 1052, which is similar to polarization rotator 502 in FIG. 5C, may further rotate the polarization of $E_{11}$ by an angle (e.g., 45 degrees) to give rise to optical signal $E_{12}$ (e.g., $E_{12}$ is linearly polarized along the y direction). Polarization-dependent beam-separator 1041, which is similar to polarization-dependent beam-separator 401 in FIG. 4C, may be configured in such a way that through which optical signal $E_{12}$ (which may manifest as the o-ray according to the configuration of polarization-dependent beam-separator 1041) may give rise to optical signal E1a that propagates along an intended optical path (e.g., along the same optical path as $E_{12}$ without lateral displacement). According to some embodiments, optical signal E1a may be polarized with the same polarization as $E_{12}$ (i.e., linearly polarized along the y direction). Optical signal $E_{13}$ may then be used for target illumination. Similar to polarization rotator 502 in FIGS. 5A and 5C, according to some embodiments, a function of the optional polarization rotator 1052 may be to enable the optical signal emerging from polarization-dependent beam-separator 1041 for target illumination to be polarized along a direction the same as one of the polarization basis components defined by coupler 1000 (e.g., orthogonal to the polarization of optical signal $E_{10}$ according to the embodiment in FIG. 10C).

According to some embodiments, optional polarization rotator 1052 in polarization transformation-separation configuration 1010 may be omitted, so that an outgoing optical signal with a polarization state that is the same as optical signal $E_{11}$ may be used for target illumination. In such a circumstance, polarization-dependent beam-separator 1041 may need to be configured, such as by orientating the optic axis of polarization-dependent beam-separator 1041 in accordance with the polarization direction of optical signal $E_{11}$, in such a way that optical signal $E_{11}$ may emerge from polarization-dependent beam-separator 1041 as a single optical signal that propagates along an intended optical path (e.g., continues with the path of $E_{11}$ without lateral displacement). According to some embodiments, polarization-dependent beam-separator 1041 may be configured with respect to sub-coupler 1001 such that optical signal $E_{11}$ may manifest as an o-ray according to the configuration of polarization-dependent beam-separator 1041.

For optical signal reception, an incoming optical signal from a target that propagates along an optical path that is the same as, but in an opposite direction to, optical signal E1a in FIG. 10C may comprise either one or both of two incoming optical signal components with polarizations the same as that of incoming optical signals Ego and $E_{30}$ illustrated in FIG. 10D, wherein optical signal $E_{20}$ is linearly polarized along the same direction as the polarization of optical signal $E_{13}$ and optical signal $E_{30}$ is linearly polarized along a direction orthogonal to the polarization of optical signal $E_{20}$. For example, as shown in FIG. 10D, $E_{20}$ is linearly polarized along the y direction and $E_{30}$ is linearly polarized along the x direction.

With reference to FIGS. 10D and 10F, incoming optical signal $E_{20}$ may pass through polarization-dependent beam-separator 1041 to give rise to optical signal $E_{21}$ with the same polarization as $E_{11}$ in FIG. 10C (i.e., linearly polarized along the y direction), wherein optical signal $E_{21}$ may manifest as an o-ray with respect to polarization-dependent beam-separator 1041. In view of optical propagation reciprocity, polarization rotator 1052 may then rotate the polarization of $E_{21}$ by an angle (e.g., 45 degrees) to give rise to optical signal $E_{22}$ which is linearly polarized along a direction the same as the polarization of optical signal $E_{11}$ in FIG. 10C. However, since the propagation direction of optical signal $E_{22}$ is opposite to that of optical signal $E_{11}$, Faraday rotator 1051, which breaks optical propagation reciprocity, may rotate the polarization of optical signal $E_{22}$ by an angle (e.g., 45 degrees) to give rise to optical signal $E_{23}$ with a linear polarization (i.e., along the y direction) that is orthogonal to the polarization of optical signal $E_{10}$. Optical signal $E_{23}$ may then be in-coupled by sub-coupler 1001 to give rise to in-coupled optical signal $E_2$ that is directed to waveguide 922 as illustrated in FIG. 10B.

With reference to FIGS. 10D and 10F, since optical signal $E_{30}$ is linearly polarized along a direction orthogonal to the polarization of $E_{20}$, through polarization-dependent beam-separator 1041, optical signal $E_{30}$ may give rise to optical signal $E_{31}$ that propagates along an optical path spatially distinct from the optical path of optical signal $E_{21}$ and is polarized with a polarization orthogonal to that of $E_{21}$. According to the embodiment in FIG. 10D, incoming optical signal $E_{31}$ is linearly polarized along the x direction and propagates along an optical path in the same direction as optical signal $E_{21}$ but laterally displaced towards the negative x direction. As illustrated in FIG. 10D, optical signal $E_{31}$ may manifest as an e-ray with respect to polarization-dependent beam-separator 1041. Polarization rotator 1052 may then rotate the polarization of $E_{31}$ by an angle (e.g., 45 degrees) to give rise to optical signal $E_{32}$ which is linearly polarized along a direction orthogonal to the polarization of optical signal $E_{22}$. Faraday rotator 1051 may rotate the polarization of optical signal $E_{32}$ by an angle (e.g., 45 degrees) to give rise to optical signal $E_{33}$ with a linear polarization (i.e., along the x direction) that is orthogonal to the polarization of optical signal $E_{23}$. Optical signal $E_{33}$ may then be in-coupled by sub-coupler 1002 to give rise to the in-coupled optical signal $E_3$ that is directed to waveguide 933 as illustrated in FIG. 10B.

According to some embodiments as described earlier, wherein the optional polarization rotator 1052 may be omitted so that an optical signal with a polarization the same as that of $E_{11}$ may be used for target illumination. Accordingly, an incoming optical signal from a target that propagates along an optical path the same as, but in an opposite direction to, optical signal $E_{11}$ in FIG. 10C may comprise either one or both of two incoming optical signal components with polarizations the same as that of optical signals $E_{22}$ and $E_{32}$ illustrated in FIG. 10D, wherein optical signal $E_{22}$ is linearly polarized along the same direction as the polarization of optical signal $E_{11}$ and optical signal $E_{32}$ is linearly polarized along a direction orthogonal to the polarization of optical signal $E_{22}$. In such a circumstance, polarization-dependent beam-separator 1041 that is configured in accordance with the polarization direction of optical signal $E_{11}$ may give rise to an optical path for optical signal $E_{22}$ that is the same as, but in opposite direction to, the optical path of $E_{11}$, whereas optical signal $E_{32}$ may propagate along another spatially distinct optical path that is displaced differently from the situation with the polarization rotator 1052. For example, incoming optical signal $E_{32}$ may now propagate along an optical path in the same direction as optical signal $E_{22}$ but laterally displaced towards a direction on the x-y plane that is no longer the negative x direction as in FIG. 10D. To compensate for the different direction of lateral displacement, the position of sub-coupler 1002 may need to be adjusted on the substrate surface accordingly.

According to some embodiments, the components of polarization transformation-separation configuration 1010 may exhibit as separate components as illustrated in FIG. 10C. According to other embodiments, some or all components of polarization transformation-separation configuration 1010 may exhibit as a single combined component. Additionally, according to some embodiments, polarization transformation-separation configuration 1010 may be an optical assembly that is separate from the PIC chip comprising polarization-diversified free-space-to-waveguide coupler 1000 as illustrated in FIG. 10C. According to other embodiments, some or all components of polarization transformation-separation configuration 1010 may be attached to the surface of the PIC chip comprising coupler 1000. According to further embodiments, some or all components of polarization transformation-separation configuration 1010 may be within or be part of the PIC chip comprising coupler 1000.

In FIGS. 10B, 10C, and 10D, for illustrative purpose, the optical signals are depicted to propagate along the z direction and are at normal incident on coupler 1000, polarization-dependent beam-separator 1041, Faraday rotator 1051, and polarization rotator 1052. In general, the propagation directions of the optical signals may be at normal incidence or at incident angles other than normal incidence with respect to these components.

FIG. 11A shows a perspective view of a three-waveguide polarization-diversified free-space-to-waveguide coupler 1100, in accordance with another embodiment of the present disclosure. Three-waveguide polarization-diversified free-space-to-wave guide coupler 1100 (herein referred to as coupler 1100 for simplicity), as indicated by the dash line in FIG. 11A, comprises three sub-couplers 1101, 1102, and 1103. According to some embodiments, each of sub-couplers 1101, 1102, and 1103 may be realized by a free-space-to-waveguide coupler, including but not limited to a grating coupler, that is coupled to a single waveguide. According to other embodiments, each of sub-couplers 1102 and 1103 may be realized by a polarization-independent free-space-to-waveguide coupler.

With reference to FIG. 11A, waveguide 921 is connected to sub-coupler 1101 as an out-coupling waveguide, waveguide 922 is connected to sub-coupler 1102 as a first in-coupling waveguide, and waveguide 933 is connected to sub-coupler 1103 as a second in-coupling waveguide. Here, waveguides 921, 922, and 933 in FIG. 11A are the same waveguides 921, 922, and 933 of coherent sensing unit 900 in FIG. 9.

As shown in FIG. 11A, a primary function of sub-coupler 1101 is to act as a transmitter to out-couple an optical signal for target illumination. Optical signal $E_1$ in waveguide 921 is out-coupled by sub-coupler 1101 into free space as an outgoing optical signal $E_{O1}$. Outgoing optical signal $E_{O1}$ is polarized according to the design of sub-coupler 1101. For example, optical signal $E_{O1}$ is linearly polarized along the x direction as illustrated in FIG. 11A.

As shown in FIG. 11A, a primary function of sub-coupler 1102 is to act as a receiver to in-couple an incoming optical signal into coherent sensing unit 900 in FIG. 9, wherein the polarization state of the incoming optical signal is orthogonal to the polarization of the outgoing optical signal. With reference to FIG. 11A, an incoming optical signal $E_{24}$ that has a polarization orthogonal to outgoing optical signal $E_{O1}$, may be in-coupled by sub-coupler 1102 to give rise to in-coupled optical signal $E_2$ in waveguide 922. The polarization of incoming optical signal $E_{24}$ that is optimally in-coupled by sub-coupler 1102 is determined according to the design of sub-coupler 1102. As an example, optical signal $E_{24}$ that is optimally in-coupled is linearly polarized along the y direction as illustrated in FIG. 11A.

As shown in FIG. 11A, a primary function of sub-coupler 1103 is to act as a receiver to in-couple an incoming optical signal into coherent sensing unit 900 in FIG. 9, wherein the polarization state of the incoming optical signal is orthogonal to the polarization of the incoming optical signal coupled by sub-coupler 1102 into waveguide 922. With reference to FIG. 11A, an incoming optical signal $E_{34}$ that has a polarization orthogonal to optical signal $E_{24}$ is in-coupled by sub-coupler 1103 to give rise to the in-coupled optical signal $E_3$ in waveguide 933. The polarization of incoming optical signal $E_{34}$ that is optimally in-coupled by sub-coupler 1103 is determined according to the design of sub-coupler 1103. For example, optical signal $E_{34}$ that is optimally in-coupled is linearly polarized along the x direction as illustrated in FIG. 11A.

Figure 11B:
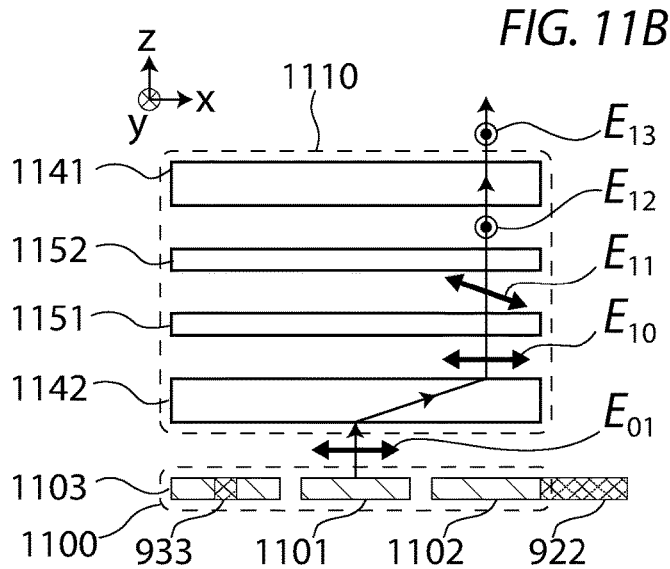
FIG. 11B show a side view of a polarization transformation-separation configuration for use with a three-wave guide polarization-diversified free-space-to-waveguide coupler for out-coupling optical signals, in accordance with another embodiment of the present disclosure.
Figure 11D:
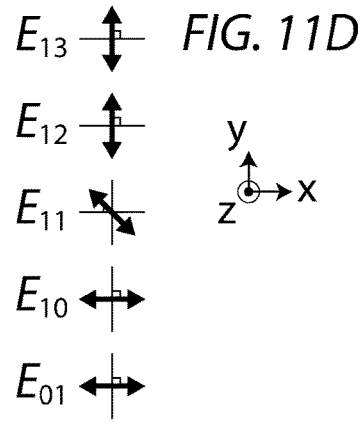
FIG. 11D shows a top view of the polarization states of the optical signals in FIG. 11B.
Figure 11C:
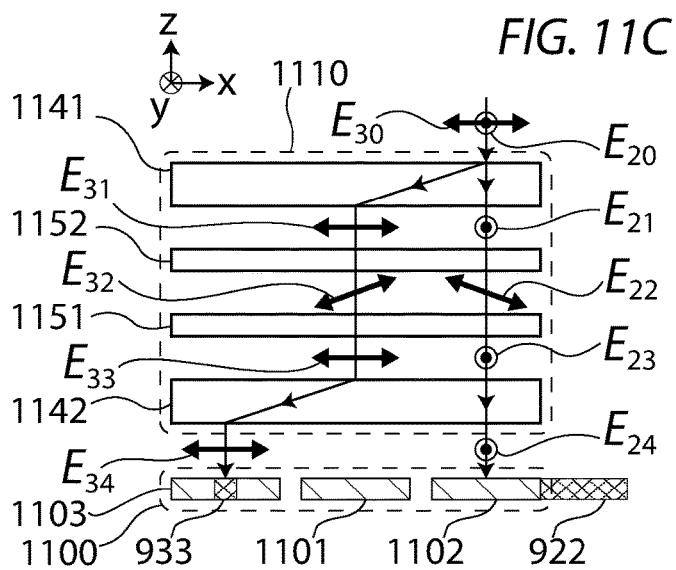
FIG. 11C show a side view of the configuration illustrated in FIG. 11B used for in-coupling optical signals.
Figure 11E:
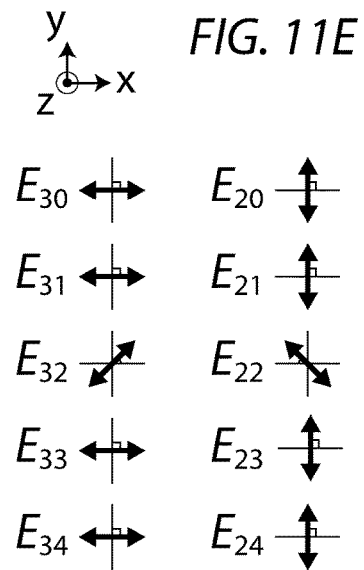
FIG. 11E shows a top view of the polarization states of the optical signals in FIG. 11C.

FIG. 11B show a side view of a polarization transformation-separation configuration 1110 for use with three-waveguide polarization-diversified free-space-to-waveguide coupler 1100 for out-coupling optical signals, in accordance with another embodiment of the present disclosure. FIG. 11C show a side view of the configuration 1110 illustrated in FIG. 11B used for in-coupling optical signals. As shown in FIGS. 11B and 11C, configuration 1110 enables the incoming optical signals $E_{24}$ and $E_{34}$ arriving at coupler 1100 and outgoing optical signal $E_{O1}$ emitted by coupler 1100 to propagate along a common optical path, wherein the common optical path lies between configuration 1110 and the target. The polarization transformation-separation configuration 1110 comprises Faraday rotator 1151, an optional polarization rotator 1152, and polarization-dependent beam-separators 1141 and 1142 as illustrated in FIGS. 11B and 11C. For illustrative purpose, FIG. 11D shows a top view of the polarization states of the optical signals in FIG. 11B. Similarly, FIG. 11E shows a top view of the polarization states of the optical signals in FIG. 11C.

Polarization transformation-separation configuration 1110 in FIGS. 11B and 11C is similar to polarization transformation-separation configuration 1010 in FIGS. 10C and 10D. The primary difference between configuration 1110 and configuration 1010 is that configuration 1110 as illustrated in FIGS. 11B and 11C has an additional polarization-dependent beam-separator 1142 that is disposed between Faraday rotator 1151 and polarization-diversified free-space-to-waveguide coupler 1100. More specifically, component 1141 in FIGS. 11B and 11C is a polarization-dependent beam-separator that is similar to polarization-dependent beam-separator 1041 in FIGS. 10C and 10D. Component 1152 in FIGS. 11B and 11C is an optional polarization rotator that is similar to polarization rotator 1052 in FIGS. 10C and 10D. Component 1151 in FIGS. 11B and 11C is a Faraday rotator that is similar to Faraday rotator 1051 in FIGS. 10C and 10D.

With reference to FIGS. 11A and 11B, sub-coupler 1101 of coupler 1100 may output an outgoing optical signal $E_{O1}$ into free space. According to some embodiments, the additional polarization-dependent beam-separator 1142 in configuration 1110 may be configured in such a way that optical signal $E_{O1}$ may be laterally displaced on the x-y plane to give rise to optical signal $E_{10}$ that has the same polarization as optical signal $E_{01}$, wherein optical signal $E_{01}$ may manifest as an e-ray with respect to polarization-dependent beam-separator 1142. As shown in FIG. 11B, optical signal $E_{01}$ is linearly polarized along the x direction and the outgoing optical signal is displaced towards the positive x direction. Similar to polarization transformation-separation configuration 1010 in FIG. 10C, Faraday rotator 1151, polarization rotator 1152, and polarization-dependent beam-separator 1141 of polarization transformation-separation configuration 1110 may transform optical signal $E_{10}$ in FIG. 11B to give rise to optical signal $E_{13}$. As shown in FIG. 11B, optical signal $E_{13}$ is linearly polarized along a direction orthogonal to that of optical signal $E_{01}$ (i.e., along the y direction).

For optical signal reception, an incoming optical signal from a target that propagates along an optical path that is the same as, but in an opposite direction to, optical signal Ela in FIG. 11B may comprise either one or both of two incoming optical signal components with polarizations that are the same as that of incoming optical signals $E_{20}$ and $E_{30}$, as illustrated in FIG. 11C, wherein optical signal $E_{20}$ is linearly polarized along the same direction as the polarization of optical signal Ela and optical signal $E_{30}$ is linearly polarized along a direction orthogonal to the polarization of optical signal $E_{20}$. For example, as shown in FIG. 11C, $E_{20}$ is linearly polarized along the y direction and $E_{30}$ is linearly polarized along the x direction. Similar to polarization transformation-separation configuration 1010, polarization-dependent beam-separator 1141, polarization rotator 1152, and Faraday rotator 1151 of polarization transformation-separation configuration 1110 may transform optical signal $E_{20}$ in FIG. 11C to give rise to optical signal $E_{23}$ that has a polarization orthogonal to that of optical signal $E_{10}$ in FIG. 11B. As shown in FIGS. 11B and 11C, the additional polarization-dependent beam-separator 1142 in configuration 1110 is configured in such a way that optical signal $E_{23}$ may give rise to an optical signal $E_{24}$ that has a polarization orthogonal to that of optical signal $E_{01}$ in FIG. 11B and propagates along an optical path to reach sub-coupler 1102. That is, optical signal $E_{24}$ may manifest as an o-ray with respect to polarization-dependent beam-separator 1142. Optical signal $E_{24}$ may then be in-coupled by sub-coupler 1102 to give rise to in-coupled optical signal $E_2$ that is directed to waveguide 922 as illustrated in FIG. 11A.

Similarly, polarization-dependent beam-separator 1141, polarization rotator 1152, and Faraday rotator 1151 of polarization transformation-separation configuration 1110 may transform optical signal $E_{30}$ in FIG. 11C to give rise to optical signal $E_{33}$ that has a polarization orthogonal to that of optical signal $E_{23}$ in FIG. 11C. Due to the configuration of the additional polarization-dependent beam-separator 1142, optical signal $E_{33}$ may be laterally displaced on the x-y plane to give rise to optical signal $E_{34}$, that has a polarization orthogonal to that of optical signal $E_{24}$, in a way the same as optical signal $E_{01}$ giving rise to optical signal $E_{10}$ but in an opposite direction. As shown in FIG. 11C, optical signal $E_{33}$ is linearly polarized along the x direction and is displaced towards the negative x direction to give rise to optical signal $E_{34}$ that is also linearly polarized along the x direction. Similar to optical signal $E_{01}$, optical signal $E_{33}$ may manifest as an e-ray with respect to polarization-dependent beam-separator 1142. Optical signal $E_{34}$ may then be in-coupled by sub-coupler 1103 to give rise to the in-coupled optical signal $E_3$ that is directed to waveguide 933 as illustrated in FIG. 11A.

According to some embodiments, optional polarization rotator 1152 in polarization transformation-separation configuration 1110 may be omitted, so that an outgoing optical signal with a polarization state that is the same as optical signal $E_{11}$ may be used for target illumination. Similar to the omission of optional polarization rotator 1052 from polarization transformation-separation configuration 1010, omission of polarization rotator 1152 in polarization-separation configuration 1110 may require polarization-dependent beam-separator 1141 to be reconfigured, such as by orientating the optic axis of polarization-dependent beam-separator 1141, in accordance with the polarization direction of optical signal $E_{11}$. Either or both of the positions of sub-couplers 1102 and 1103 may also need to be adjusted on the substrate surface accordingly in order to compensate for the different orientation of the optic axis of polarization-dependent beam-separator 1141.

Similar to polarization transformation-separation configuration 1010, according to some embodiments, the components of polarization transformation-separation configuration 1110 may exhibit as separate components as illustrated in FIG. 11B. According to other embodiments, some or all components of polarization transformation-separation configuration 1110 may exhibit as a single combined component. Additionally, according to some embodiments, polarization transformation-separation configuration 1110 may be an optical assembly that is separate from the PIC chip comprising polarization-diversified free-space-to-waveguide coupler 1100 as illustrated in FIG. 11B. According to other embodiments, some or all components of polarization transformation-separation configuration 1110 may be attached to the surface of the PIC chip comprising coupler 1100. According to further embodiments, some or all components of polarization transformation-separation configuration 1110 may be within or be part of the PIC chip comprising coupler 1100.

In FIGS. 11A, 11B and 11C, for illustrative purpose, the optical signals are depicted to propagate along the z direction and are at normal incident on coupler 1100, polarization-dependent beam-separators 1141 and 1142, Faraday rotator 1151, and polarization rotator 1152. In general, the propagation directions of the optical signals may be at normal incidence or at incident angles other than normal incidence with respect to these components.

FIG. 12A show a side view of a polarization transformation-separation configuration 1210 for use with three-waveguide polarization-diversified free-space-to-waveguide coupler 1100 for out-coupling optical signals, in accordance with a further embodiment of the present disclosure. FIG. 12B show a side view of configuration 1210 illustrated in FIG. 12A used for in-coupling optical signals. Configuration 1210 enables incoming optical signals $E_{24}$ and $E_{34}$ arriving at coupler 1100 and outgoing optical signal $E_{01}$ emitted by coupler 1100 to propagate along a common optical path, wherein the common optical path lies between configuration 1210 and the target. As shown in FIGS. 12A and 12B, polarization transformation-separation configuration 1210 comprises Faraday rotator 1251, an optional polarization rotator 1252, polarization-dependent beam-separators 1241 and 1242, and an optional quarter-wave plate 1261. For illustrative purpose, FIG. 12C shows a top view of the polarization states of the optical signals in FIG. 12A. Similarly, FIG. 12D shows a top view of the polarization states of the optical signals in FIG. 12B.

Polarization transformation-separation configuration 1210 in FIGS. 12A and 12B is a modified embodiment of polarization transformation-separation configuration 1110 in FIGS. 11B and 11C. Primary modifications of configuration 1210 from configuration 1110 comprise the followings: (1) polarization rotator 1252 of configuration 1210, if present, is configured in such a way that effects a polarization rotation in a direction opposite to the rotation direction effected by polarization rotator 1152 of configuration 1110; (2) polarization-dependent beam-separator 1241 of configuration 1210 is configured by, for example, orienting the optic axis of 1241 in such a way that effects a lateral displacement, if any, in a direction opposite to the lateral displacement effected by polarization-dependent beam-separator 1242 for the case when optional polarization rotator 1252 is present; and (3) configuration 1210 comprises an additional quarter-wave plate 1261 that is disposed between polarization-dependent beam-separator 1241 and the target. Accordingly, polarization-dependent beam-separator 1242 of configuration 1210 is similar to polarization-dependent beam-separator 1142 of configuration 1110, and Faraday rotator 1251 of configuration 1210 is similar to Faraday rotator 1151 of configuration 1110.

On one hand, with reference to FIG. 12B, modifications (1) and (2) in configuration 1210 described above may result in an optical path for optical signals $E_{20}$, $E_{21}$, $E_{22}$, $E_{23}$, and $E_{24}$ with a path length that is similar to the path length of the optical path for optical signals $E_{30}$, $E_{31}$, $E_{32}$, $E_{33}$, and $E_{34}$, in comparison to the corresponding optical paths in configuration 1110 as illustrated in FIG. 11C. Modifications (1) and (2) may thus have an advantage of minimizing the phase difference between optical signals $E_{24}$ and $E_{34}$ arriving respectively at sub-couplers 1102 and 1103. With reference to FIG. 12A, modifications (1) and (2) described above may, if optional polarization rotator 1252 is present, also enable optical signal $E_{13}$ to be emitted at a location and direction on the surface of polarization-dependent beam-separator 1241 that are similar to the emitting location and direction of optical signal $E_{01}$ on the surface of sub-coupler 1101. Modifications (1) and (2) may thus have another advantage of enabling simplified optical alignment for the installation of polarization transformation-separation configuration 1210 with coupler 1100 by using the outgoing optical signal from sub-coupler 1101 of coupler 1100.

On the other hand, with reference to FIGS. 12A and 12C, modification (3) described above may enable the use of a circularly-polarized optical signal $E_{1C}$ for target illumination. More specifically, quarter-wave plate 1261 may transform a linearly polarized optical signal $E_{13}$ to give rise to a circularly-polarized optical signal $E_{1C}$ for target illumination. As shown in FIGS. 12A and 12C, optical signal $E_{13}$ is linearly polarized along the x direction and optical signal $E_{1C}$ is right-circularly polarized with respect to its propagation direction. For optical signal reception, an incoming optical signal from a target may be decomposed according to any two orthogonal polarizations. As shown in FIGS. 12B and 12D, an incoming optical signal from the target, which propagates towards the negative z direction, may comprise either one or both of two polarization components $E_{tC}$ and $E_{3C}$, wherein one of them is right-circularly polarized and the other one of them is left-circularly polarized with respect to their propagation direction. As illustrated in FIGS. 12B and 12D, $E_{tC}$ is right-circularly polarized and $E_{3C}$ is left-circularly polarized with respect to the negative z direction. As shown in FIG. 12B, quarter-wave plate 1261 may transform optical signal $E_{tC}$ to give rise to a linearly polarized optical signal $E_{20}$, and transform optical signal $E_{3C}$ to give rise to optical signal $E_{30}$ that has a polarization orthogonal to $E_{20}$. As illustrated in FIGS. 12B and 12D, $E_{20}$ is linearly polarized along the x direction and $E_{30}$ is linearly polarized along the y direction. In some aspects, using a circularly-polarized optical signal instead of a linearly-polarized optical signal for target illumination that is enabled by modification (3) may have an advantage of minimizing the odd of significant signal loss due to certain properties of the target or target surface. Such significant signal loss may arise in circumstances such as, but not limited to, when a target surface preferentially reflects light with a linear polarization that is by coincidence orthogonal to a linearly polarized illuminating optical signal. A circularly-polarized illuminating optical signal always comprises a pair of orthogonal linearly-polarized components that may avoid the vanishing of reflected optical signal under such a situation.

According to some embodiments, optional polarization rotator 1252 in polarization transformation-separation configuration 1210 may be omitted. Similar to the omission of optional polarization rotator 1152 from polarization transformation-separation configuration 1110, the omission of polarization rotator 1252 in polarization transformation-separation configuration 1210 may require polarization-dependent beam-separator 1241 and quarter-wave plate 1261 to be reconfigured, such as by orientating the optic axes of polarization-dependent beam-separator 1241 and quarter-wave plate 1261 in accordance with the polarization direction of optical signal $E_{11}$. Either or both of the positions of sub-couplers 1102 and 1103 may also need to be adjusted on the substrate surface accordingly in order to compensate for the different orientations of the optic axes of polarization-dependent beam-separator 1241 and quarter-wave plate 1261.

Similar to polarization transformation-separation configuration 1110, according to some embodiments, the components of polarization transformation-separation configuration 1210 may exhibit as separate components as illustrated in FIG. 12A. According to other embodiments, some or all components of polarization transformation-separation configuration 1210 may exhibit as a single combined component. Additionally, according to some embodiments, polarization transformation-separation configuration 1210 may be an optical assembly that is separate from the PIC chip comprising polarization-diversified free-space-to-waveguide coupler 1100 as illustrated in FIG. 12A. According to other embodiments, some or all components of polarization transformation-separation configuration 1210 may be attached to the surface of the PIC chip comprising coupler 1100. According to further embodiments, some or all components of polarization transformation-separation configuration 1210 may be within or be part of the PIC chip comprising coupler 1100.

In FIGS. 12A and 12B, for illustrative purpose, the optical signals are depicted to propagate along the z direction and are at normal incident on coupler 1100, polarization-dependent beam-separators 1241 and 1242, Faraday rotator 1251, polarization rotator 1252, and quarter-wave plate 1261. In general, the propagation directions of the optical signals may be at normal incidence or at incident angles other than normal incidence with respect to these components.

Figure 13B:
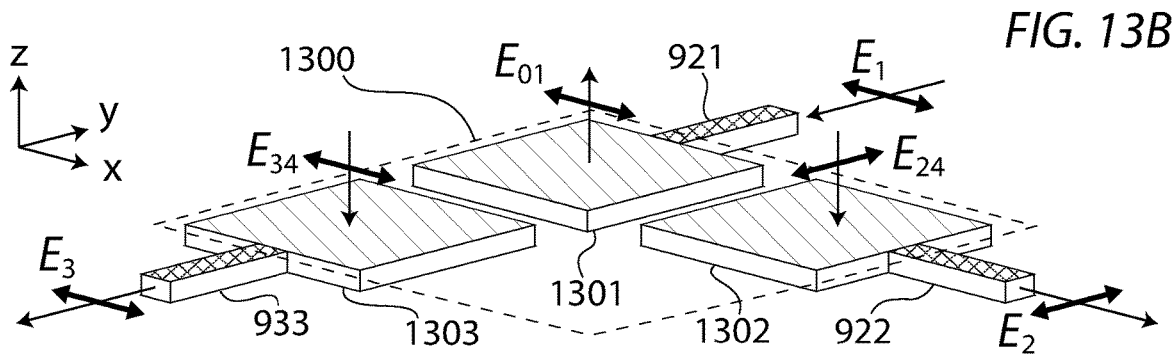
FIG. 13B shows a perspective view of the coupler illustrated in FIG. 13A.

FIG. 13A shows a top view of a three-waveguide polarization-diversified free-space-to-waveguide coupler 1300, in accordance with a further embodiment of the present disclosure. FIG. 13B shows a perspective view of coupler 1300 illustrated in FIG. 13A. In addition, FIG. 13B shows polarized outgoing and incoming optical signals $E_{01}$, $E_{24}$, and $E_{34}$ coupling respectively with sub-couplers 1301, 1302, and 1303. Three-waveguide polarization-diversified free-space-to-waveguide coupler 1300 (herein referred to as coupler 1300 for simplicity), as indicated by the dash line in FIGS. 13A and 13B, comprises three sub-couplers 1301, 1302, and 1303. According to some embodiments, each of sub-couplers 1301, 1302, and 1303 may be realized by a free-spaceto-waveguide coupler, including but not limited to a grating coupler, that is coupled to a single waveguide. According to other embodiments, each of sub-couplers 1302 and 1303 may be realized by a polarization-independent free-space-to-waveguide coupler. Coupler 1300 is a modified embodiment of coupler 1100 as illustrated in FIG. 11A. Sub-coupler 1301 of coupler 1300 in FIGS. 13A and 13B is similar to sub-coupler 1101 of coupler 1100 in FIG. 11A. Sub-coupler 1302 of coupler 1300 in FIGS. 13A and 13B is similar to sub-coupler 1102 of coupler 1100 in FIG. 11A. Sub-coupler 1303 of coupler 1300 in FIGS. 13A and 13B is similar to sub-coupler 1103 of coupler 1100 in FIG. 11A. Comparing coupler 1300 and coupler 1100, the spatial arrangement of sub-couplers of coupler 1300 may be advantageous (for example, being more compact) to some embodiments of coherent sensing unit 900 in FIG. 9.

Figure 13C:
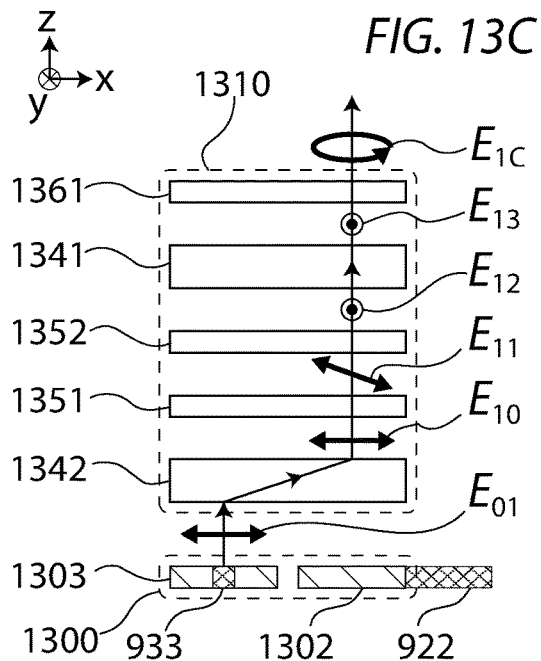
FIG. 13C shows a side view of a polarization transformation-separation configuration for use with a three-waveguide polarization-diversified free-space-to-waveguide coupler for out-coupling optical signals, in accordance with a yet further embodiment of the present disclosure.
Figure 13D:
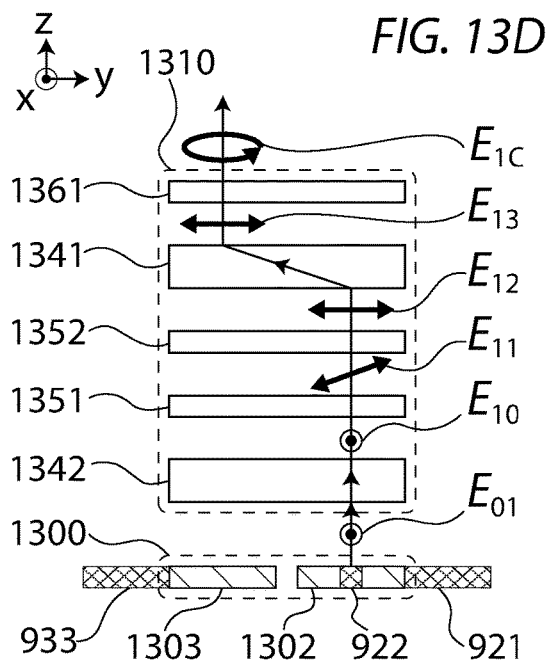
FIG. 13D shows another side view of the configuration illustrated in FIG. 13C.

FIG. 13C shows a side view of a polarization transformation-separation configuration 1310 for use with three-waveguide polarization-diversified free-space-to-waveguide coupler 1300 for out-coupling optical signals, in accordance with a yet further embodiment of the present disclosure. FIG. 13D shows another side view of configuration 1310 illustrated in FIG. 13C. FIG. 13E shows a side view of configuration 1310 as illustrated in FIG. 13C used for in-coupling optical signals. FIG. 13F shows another side view of configuration 1310 illustrated in FIG. 13E. As shown in FIGS. 13C and 13E, configuration 1310 enables incoming optical signals $E_{24}$ and $E_{34}$ arriving at coupler 1300 and outgoing optical signal $E_{01}$ emitted by coupler 1300 to propagate along a common optical path, wherein the common optical path lies between configuration 1310 and the target.

For illustrative purpose, FIG. 13G shows a top view of the polarization states and path locations on the x-y plane of the optical signals in FIGS. 13C and 13D. Also shown in FIG. 13G is an inset showing the top view of coupler 1300 indicating the locations of sub-couplers 1301, 1302, and 1303 on the x-y plane as a reference for the path locations of the optical signals in FIG. 13G. Similarly, FIG. 13H shows a top view of the polarization states and path locations on the x-y plane of the optical signals in FIGS. 13E and 13F. The path locations on the x-y plane in FIG. 13H may be referenced to the locations of sub-couplers 1301, 1302, and 1303 indicated in the inset of FIG. 13G.

According to FIGS. 13C, 13D, 13E, and 13F, the polarization transformation-separation configuration 1310 comprises Faraday rotator 1351, an optional polarization rotator 1352, polarization-dependent beam-separators 1341 and 1342, and an optional quarter-wave plate 1361.

Polarization transformation-separation configuration 1310 shown in FIGS. 13C, 13D, 13E, and 13F is a modified embodiment of polarization transformation-separation configuration 1110 in FIGS. 11B and 11C. Primary modifications of configuration 1310 from configuration 1110 comprise the followings: (1) polarization-dependent beam-separator 1341 of configuration 1310 is configured such as, but not limited to, by orienting the optic axis of polarization-dependent beam-separator 1341 in such a way that effects a lateral displacement, if any, in a direction on the x-y plane that is perpendicular to the lateral displacement effected by polarization-dependent beam-separator 1342 for the case when optional polarization rotator 1352 is present; and (2) configuration 1310 comprises an additional quarter-wave plate 1361 disposed between polarization-dependent beam-separator 1341 and the target. Accordingly, polarization-dependent beam-separator 1342 of configuration 1310 is similar to polarization-dependent beam-separator 1142 of configuration 1110, Faraday rotator 1351 of configuration 1310 is similar to Faraday rotator 1151 of configuration 1110, and polarization rotator 1352 of configuration 1310 is similar to polarization rotator 1152 of configuration 1110.

More specifically, in polarization transformation-separation configuration 1310, polarization-dependent beam-separator 1342 effects a lateral displacement, if any, along the x direction as shown in FIGS. 13C and 13E, whereas polarization-dependent beam-separator 1341 effects a lateral displacement, if any, along the y direction as shown in FIGS. 13D and 13F. This is in contrast to polarization transformation-separation configurations 1110 and 1210 wherein the polarization-dependent beam-separators in either configuration effect lateral displacements, if any, along the x direction.

Similar to polarization transformation-separation configuration 1210 in FIGS. 12A and 12B, with reference to FIGS. 13E and 13F, modification (1) in configuration 1310 described above may result in an optical path for optical signals $E_{20}$, $E_{21}$, $E_{22}$, $E_{23}$, and $E_{24}$ with a path length that is similar to the path length of the optical path for optical signals $E_{30}$, $E_{31}$, $E_{32}$, $E_{33}$, and $E_{34}$, in comparison to the corresponding optical paths in configuration 1110 as illustrated in FIG. 11C. Each of optical signals $E_{2C}$ and $E_{3C}$ as illustrated in FIGS. 13E and 13F experiences one lateral displacement when propagating from quarter-wave plate 1361 through polarization-dependent beam-separator 1341, polarization rotator 1352, Faraday rotator 1351, and polarization-dependent beam-separator 1342 to coupler 1300. Modification (1) may thus have an advantage of minimizing the phase difference between optical signals $E_{2C}$ and $E_{3C}$ arriving respectively at sub-couplers 1302 and 1303.

On the other hand, similar to configuration 1210 in FIGS. 12A and 12B, with reference to configuration 1310 in FIGS. 13C and 13D, modification (2) described above may also enable the use of a circularly polarized optical signal $E_{1C}$ for target illumination.

According to some embodiments, optional polarization rotator 1352 in polarization transformation-separation configuration 1310 may be omitted. Similar to the omission of optional polarization rotator 1252 from polarization transformation-separation configuration 1210, the omission of polarization rotator 1352 in polarization-separation configuration 1310 may require polarization-dependent beam-separator 1341 and quarter-wave plate 1361 to be reconfigured by, for example, orientating the optic axes of polarization-dependent beam-separator 1341 and quarter-wave plate 1361 in accordance with the polarization direction of optical signal $E_{11}$. Either or both of the positions of sub-couplers 1302 and 1303 may also need to be adjusted on the substrate surface accordingly in order to compensate for the different orientations of the optic axes of polarization-dependent beam-separator 1341 and quarter-wave plate 1361.

Similar to polarization transformation-separation configuration 1110, according to some embodiments, the components of polarization transformation-separation configuration 1310 may exhibit as separate components as illustrated in FIG. 13C. According to other embodiments, some or all components of polarization transformation-separation configuration 1310 may exhibit as a single combined component. Additionally, according to some embodiments, polarization transformation-separation configuration 1310 may be an optical assembly that is separate from the PIC chip comprising polarization-diversified free-space-to-waveguide coupler 1300 as illustrated in FIG. 13C. According to other embodiments, some or all components of polarization transformation-separation configuration 1310 may be attached to the surface of the PIC chip comprising coupler 1300. According to further embodiments, some or all components of polarization transformation-separation configuration 1310 may be within or be part of the PIC chip comprising coupler 1300.

In FIGS. 13B, 13C, 13D, 13E, and 13F, for illustrative purpose, the optical signals are depicted to propagate along the z direction and are at normal incident on coupler 1300, polarization-dependent beam-separators 1341 and 1342, Faraday rotator 1351, polarization rotator 1352, and quarter-wave plate 1361. In general, the propagation directions of the optical signals may be at normal incidence or at incident angles other than normal incidence with respect to these components.

Coherent sensing units 100, 700, 710, 800, and 900, respectively illustrated in FIGS. 1A, 7A, 7B, 8, and 9, may give rise to outgoing optical signals with a fixed polarization for target illumination. In some applications of optical coherent sensing, it may be desirable for the polarization state of an illuminating optical signal to be adjustable dynamically.

Figure 14:
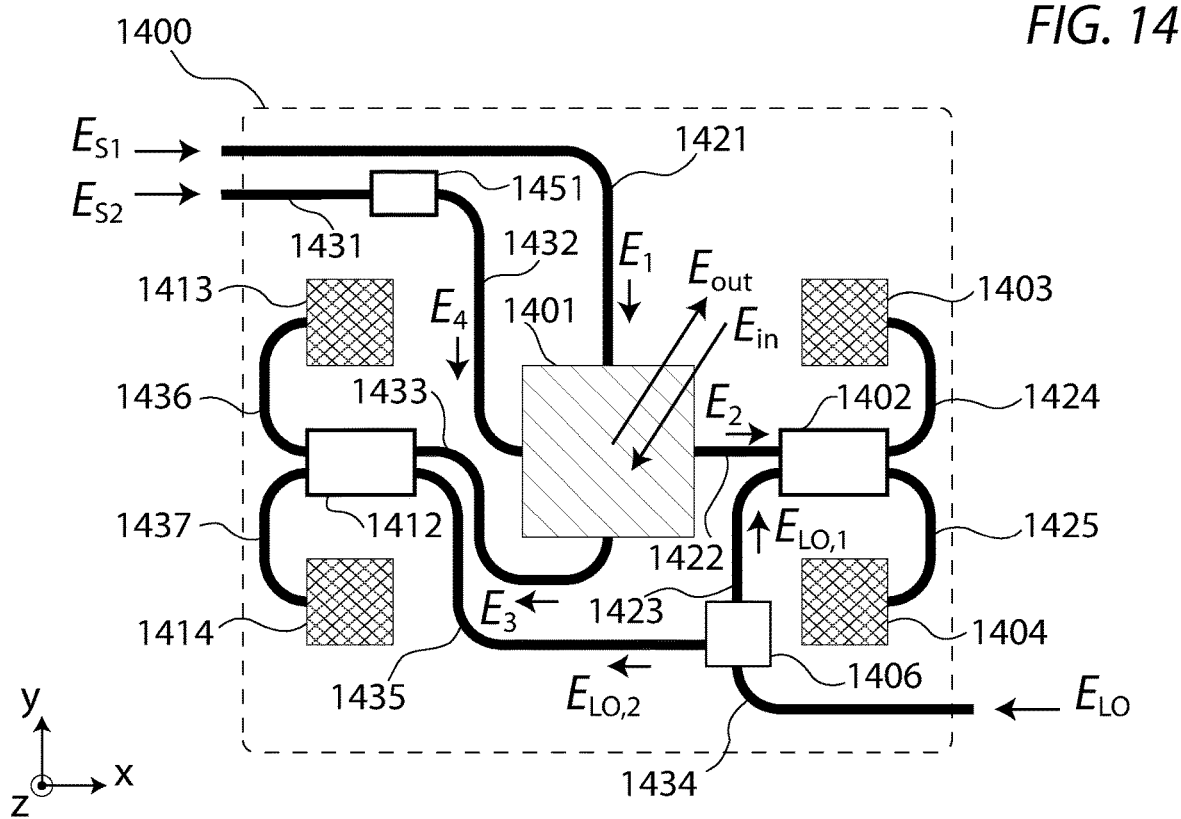
FIG. 14 shows a plan view of a coherent sensing unit for transmitting and receiving optical signals based on polarization diversity, wherein the polarization of the transmitted optical signal is adjustable, in accordance with an embodiment of the present disclosure.

FIG. 14 shows a plan view of a coherent sensing unit 1400 for transmitting and receiving optical signals based on polarization diversity, wherein the polarization of the transmitted optical signal is adjustable, in accordance with an embodiment of the present disclosure. Coherent sensing unit 1400 is similar to coherent sensing units 700, 710, 800, and 900 that detect an incoming optical signal with any polarization state. The primary difference between coherent sensing unit 1400 and coherent sensing unit 900 is that coherent sensing unit 1400 comprises a polarization-diversified free-space-to-waveguide coupler that may be used to out-couple an outgoing optical signal with any polarization state, in addition to directing in-coupled optical signals with any polarization states to waveguides that are distinct from the waveguides carrying the outgoing optical signals.

More specifically, referring to FIG. 14, at least one of optical source signals $E_{S1}$ and $E_{S2}$ are supplied to coherent sensing unit 1400. Optical source signals $E_{S1}$ and $E_{S2}$ are respectively guided into coherent sensing unit 1400 through waveguides 1421 and 1431. According to some embodiments, optical source signals $E_{S1}$ and $E_{S1}$ may come from the same light source. In such a circumstance, the outgoing optical signals arising from $E_{S1}$ and $E_{S1}$ may be coherently combined to form a single optical signal. According to other embodiments, optical source signals $E_{S1}$ and $E_{S2}$ may come from different light sources. Either one or both of waveguides 1421 and 1431 may be connected to an optional phase shifter, which is used to adjust the relative phase between the optical signals in waveguides 1421 and 1431. As an example, in FIG. 14, waveguide 1431 may be connected to phase shifter 1451, which directs phase-shifted optical source signal $E_{S2}$ as optical signal $E_4$ to waveguide 1432. According to some embodiments, phase shifter 1451 may be, but not limited to, an electro-optic phase shifter or a thermo-optic phase shifter. Local oscillator (LO) $E_{LO}$ is supplied to coherent sensing unit 1400 through waveguide 1434.

In FIG. 14, polarization-diversified free-space-to-waveguide coupler 1401 (herein referred to as coupler 1401 for simplicity) is a four-waveguide coupler that is connected to waveguides 1421, 1422, 1432, and 1433. Coupler 1401 may function as both a transmitter and a receiver.

As a transmitter, with reference to FIG. 14, coupler 1401 may couple optical signal $E_1$ (which is essentially the same as optical source signal $E_{S1}$) from waveguide 1421 and optical signal $E_4$ from waveguide 1432 into free space as one or more outgoing optical signals, which may be used for target illumination by the optical coherent imager. The outgoing optical signals output by coupler 1401 propagate in a direction that is out of the x-y plane (i.e., the propagation direction of $E_{out}$ has a nonzero z component). The outgoing optical signals are polarized with polarization states defined by the design of coupler 1401. According to some embodiments, the outgoing optical signal arising from optical signal $E_1$ may be orthogonally polarized with respect to the outgoing optical signal arising from optical signal $E_4$. According to some embodiments wherein optical signals $E_1$ and $E_4$ are coherent, the outgoing optical signals may manifest as a single outgoing optical signal $E_{out}$ with a polarization state defined by the design of coupler 1401, and the amplitudes and the relative phase of optical signals $E_1$ and $E_4$.

As a receiver, coupler 1401 may couple an incoming optical signal $E_{in}$ into coherent sensing unit 1400. Incoming optical signal $E_{in}$ coupled by coupler 1401 may be directed to either or both waveguides 1422 and 1433, depending on the polarization state of incoming optical signal $E_{in}$. The polarization components of incoming optical signal $E_{in}$ that are coupled to waveguides 1422 and 1433 depend on the design of coupler 1401. According to some embodiments wherein optical signal $E_1$ is nonzero, the polarization component of incoming optical signal $E_{in}$ that is orthogonal to the polarization component of outgoing optical signal Emit arising from optical signal $E_1$ may be directed to waveguide 1422 as an in-coupled optical signal $E_2$, and the polarization component of incoming optical signal $E_{in}$ that is orthogonal to the polarization component of incoming optical signal $E_{in}$ directed to waveguide 1422 may be directed to waveguide 1433 as an in-coupled optical signal $E_3$. According to other embodiments wherein optical signal $E_4$ is nonzero, the polarization component of incoming optical signal $E_{in}$ that is orthogonal to the polarization component of outgoing optical signal $E_{out}$ arising from optical signal $E_4$ may be directed to waveguide 1433 as an in-coupled optical signal $E_3$, and the polarization component of incoming optical signal $E_{in}$ that is orthogonal to the polarization component of incoming optical signal $E_{in}$ directed to waveguide 1433 may be directed to waveguide 1422 as an in-coupled optical signal $E_2$.

Figure 15A:
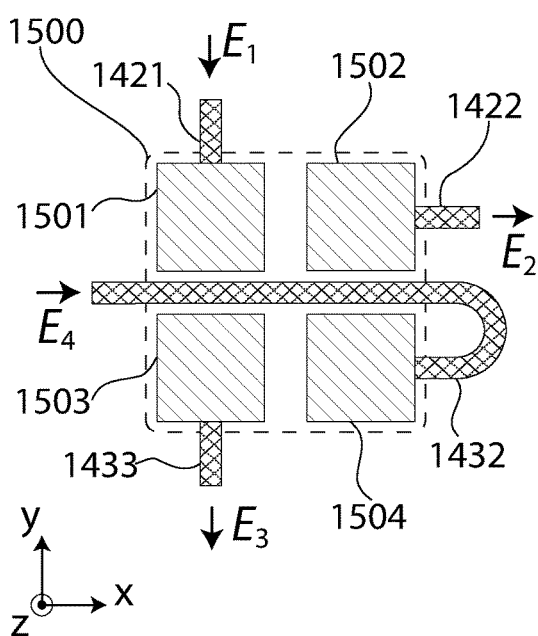
FIG. 15A shows a top view of a four-waveguide polarization-diversified free-space-to-waveguide coupler, in accordance with an embodiment of the present disclosure.
Figure 16A:
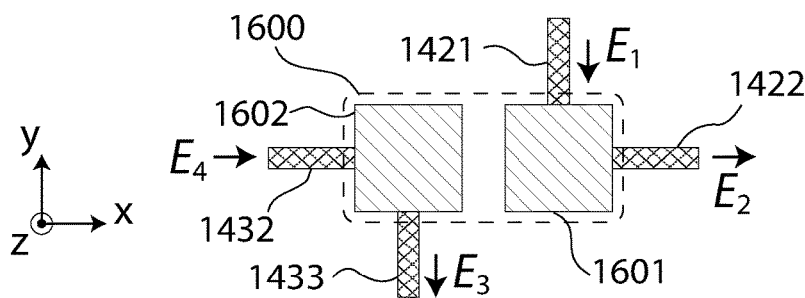
FIG. 16A shows a top view of a four-waveguide polarization-diversified free-space-to-waveguide coupler, in accordance with another embodiment of the present disclosure.

In FIG. 14, although coupler 1401 is drawn as a single entity, coupler 1401 in general may comprise a single photonic component or multiple photonic components. Embodiments of coupler 1401 are illustrated in FIGS. 15A, 16A, and 17A to be described below. According to some embodiments, similar to coupler 101 in FIGS. 1A and 1B, coupler 1401 may also comprise any of TE-TM mode converters, splitters, and combiners.

In FIG. 14, splitting coupler 1406 splits the LO $E_{LO}$ from waveguide 1434 and directs a fraction of the LO to waveguide 1423 as the LO $E_{LO,1}$ and a fraction of the LO to waveguide 1435 as the LO $E_{LO,2}$. The fractions of the LO that are passed respectively to waveguides 1423 and 1435 depend on the splitting ratio and loss of splitting coupler 1406. According to some embodiments, splitting coupler 1406 may be a 50/50 splitting coupler. According to other embodiments, splitting coupler 1406 may have a splitting ratio other than 50/50.

In FIG. 14, component 1402 is a 2×2 optical coupler that mixes in-coupled optical signal $E_2$ from waveguide 1422 and the LO $E_{LO,1}$ from waveguide 1423, and splits and directs the mixed signal to waveguides 1424 and 1425. According to some embodiments, 2×2 optical coupler 1402 may be similar to 2×2 optical coupler 902 of coherent sensing unit 900 in FIG. 9.

In FIG. 14, component 1403 is a square-law photodetector that receives and detects the optical signal from waveguide 1424. Similarly, in FIG. 14, component 1404 is a square-law photodetector that receives and detects the optical signal from waveguide 1425. According to some embodiments, photodetectors 1403 and 1404 may be similar to photodetectors 903 and 904 of coherent sensing unit 900 in FIG. 9.

In FIG. 14, similar to 2×2 optical coupler 912 of coherent sensing unit 900 in FIG. 9, component 1412 is a 2×2 optical coupler that mixes in-coupled optical signal $E_3$ from waveguide 1433 and the LO $E_{LO,2}$ from waveguide 1435, and splits and directs the mixed signal to waveguides 1436 and 1437.

In FIG. 14, component 1413 is a square-law photodetector that receives and detects the optical signal from waveguide 1436. Similarly, in FIG. 14, component 1414 is a square-law photodetector that receives and detects the optical signal from waveguide 1437. According to some embodiments, photodetectors 1413 and 1414 may be similar to photodetectors 913 and 914 of coherent sensing unit 900 in FIG. 9.

Figure 15B:
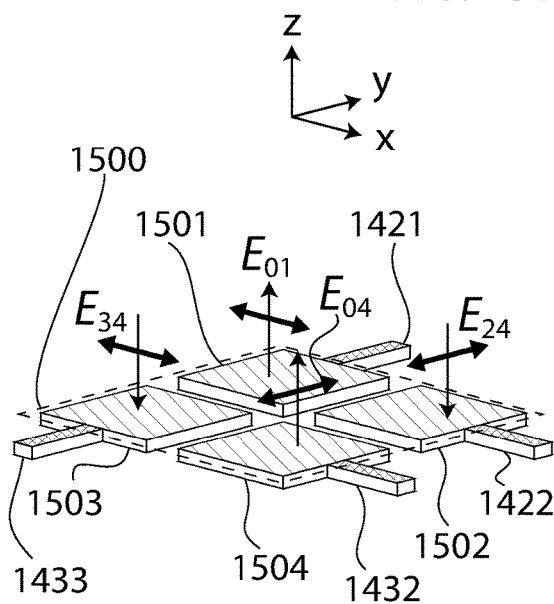
FIG. 15B shows a perspective view of the coupler illustrated in FIG. 15A.

FIG. 15A shows a top view of a four-waveguide polarization-diversified free-space-to-waveguide coupler 1500 (herein referred to as coupler 1500 for simplicity), in accordance with an embodiment of the present disclosure. FIG. 15B shows a perspective view of coupler 1500 illustrated in FIG. 15A. FIG. 15B additionally shows polarized outgoing and incoming optical signals $E_{01}$, $E_{24}$, $E_{34}$, and $E_{04}$ coupling respectively with sub-couplers 1501, 1502, 1503, and 1504. Coupler 1500, as indicated by the dash line in FIG. 15A, comprises four sub-couplers 1501, 1502, 1503, and 1504. According to some embodiments, each of the sub-couplers 1501, 1502, 1503, and 1504 may be realized by a free-space-to-waveguide coupler, including but not limited to a grating coupler, that is coupled to a single waveguide. According to some embodiments, each of the sub-couplers 1502 and 1503 may be realized by a polarization-independent free-space-to-waveguide coupler. Coupler 1500 is a modified embodiment of coupler 1300 as illustrated in FIG. 13A, with an addition of sub-coupler 1504 that is connected to waveguide 1432 of coherent sensing unit 1400 in FIG. 14.

FIG. 15C shows a side view of a polarization transformation-separation configuration 1510 for use with four-waveguide polarization-diversified free-space-to-waveguide coupler 1500 for out-coupling optical signals, in accordance with an embodiment of the present disclosure. FIG. 15F shows a side view of configuration 1510 as illustrated in FIG. 15C used for in-coupling optical signals. Configuration 1510 enables incoming optical signals $E_{24}$ and $E_{34}$ arriving at coupler 1500 and outgoing optical signals $E_{01}$ and $E_{04}$ emitted by coupler 1500 to propagate along a common optical path, wherein the common optical path lies between configuration 1510 and the target. FIG. 15D shows another side view of configuration 1510 illustrated in FIG. 15C. FIG. 15G shows another side view of configuration 1510 illustrated in FIG. 15F. Embodiments of the optical paths and the polarization states of the outgoing optical signals arising from optical signals $E_1$ and $E_4$ and the incoming optical signals that give rise to $E_2$ and $E_3$ are shown in FIGS. 15C, 15D, 15F, and 15G. For simplicity, waveguides 1421, 1422, 1432, and 1433 are not shown explicitly in FIGS. 15C, 15D, 15F, and 15G.

For illustrative purpose, FIG. 15E shows a top view of the polarization states and path locations on the x-y plane of the optical signals in FIGS. 15C and 15D. FIG. 15E additionally shows an inset for the top view of coupler 1500 indicating the locations of sub-couplers 1501, 1502, 1503, and 1504 on the x-y plane as a reference for the path locations of the optical signals in FIG. 15E. Similarly, FIG. 15H shows a top view of the polarization states and path locations on the x-y plane of the optical signals in FIGS. 15F and 15G. The inset in FIG. 15H shows the top view of coupler 1500 indicating the locations of sub-couplers 1501, 1502, 1503, and 1504 on the x-y plane as a reference for the path locations of the optical signals in FIG. 15H.

Polarization transformation-separation configuration 1510 shown in FIGS. 15C, 15D, 15F, and 15G is essentially the same as polarization transformation-separation configuration 1310 shown in FIGS. 13C, 13D, 13E, and 13F, except for the omission of quarter-wave plate 1361 that is used to produce a circularly polarized outgoing optical signal for target illumination. Coherent sensing unit 1400 operating with coupler 1500 and polarization transformation-separation configuration 1510 may produce an outgoing optical signal with any polarization state, including linear polarization, circular polarization or elliptical polarization, for target illumination by adjusting the amplitudes and relative phase of optical signals $E_1$ and $E_4$ in waveguides 1421 and 1432. According to some embodiments, to produce an outgoing optical signal with a particular polarization state using polarization transformation-separation configuration 1510, sub-couplers 1501, 1502, 1503, and 1504 of coupler 1500 may need to be designed and configured in such a way that maximizes the spatial overlap of outgoing optical signals $E_{13}$ and $E_{43}$ as illustrated in FIGS. 15C, 15D, and 15E, so as to minimize the spatial variation of the polarization of the outgoing optical signal combined from optical signals $E_{13}$ and $E_{43}$.

In FIGS. 15B, 15C, 15D, 15F, and 15G, for illustrative purpose, the optical signals are depicted to propagate along the z direction and are at normal incident on coupler 1500, polarization-dependent beam-separators 1541 and 1542, Faraday rotator 1551, and polarization rotator 1552. In general, the propagation directions of the optical signals may be at normal incidence or at incident angles other than normal incidence with respect to these components.

Figure 16B:
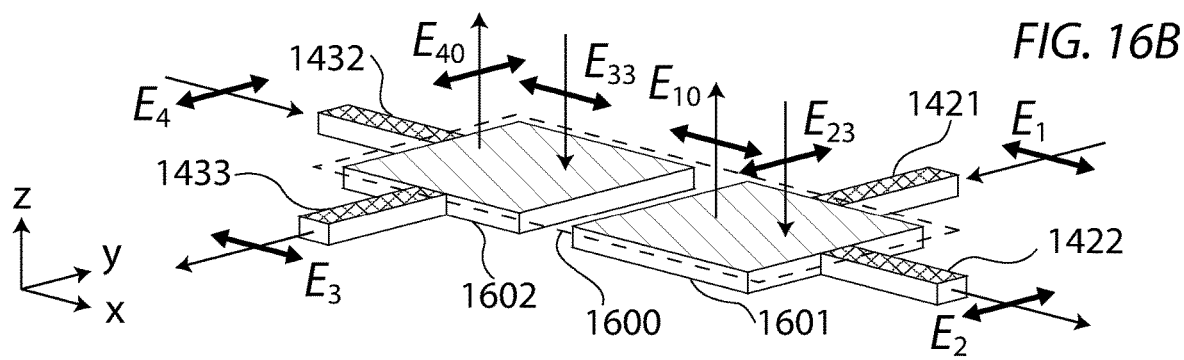
FIG. 16B shows a perspective view of the coupler illustrated in FIG. 16A.

FIG. 16A shows a top view of a four-waveguide polarization-diversified free-space-to-waveguide coupler 1600 (herein referred to as coupler 1600 for simplicity), in accordance with another embodiment of the present disclosure. FIG. 16B shows a perspective view of coupler 1600 illustrated in FIG. 16A. FIG. 16B additionally shows polarized outgoing and incoming optical signals $E_{10}$, $E_{40}$, $E_{23}$, and $E_{33}$ coupling with sub-couplers 1601 and 1602. Coupler 1600, as indicated by the dash line in FIG. 16A, comprises two sub-couplers 1601 and 1602. According to some embodiments, each of sub-couplers 1601 and 1602 may be realized by either polarization-diversified free-space-to-waveguide coupler 101 as illustrated in FIG. 1B or polarization-diversified free-space-to-waveguide coupler 200 as illustrated in FIG. 2. Coupler 1600 is a modified embodiment of coupler 1000 as illustrated in FIG. 10A, with an additional waveguide 1432 connecting to sub-coupler 1602 of coherent sensing unit 1600 in FIG. 16A for out-coupling optical signal $E_4$.

In FIG. 16B, for illustrative purpose, outgoing optical signal $E_{10}$ and incoming optical signal $E_{23}$ are drawn to couple with sub-coupler 1601 at different spatial locations. In general, outgoing optical signal $E_{10}$ and incoming optical signal $E_{23}$ may couple with sub-coupler 1601 at the same spatial locations according to some embodiments, or at different spatial locations according to other embodiments. Similarly, outgoing optical signal $E_{40}$ and incoming optical signal $E_{33}$ may couple with sub-coupler 1602 at the same spatial locations according to some embodiments, or at different spatial locations according to other embodiments.

Figure 16C:
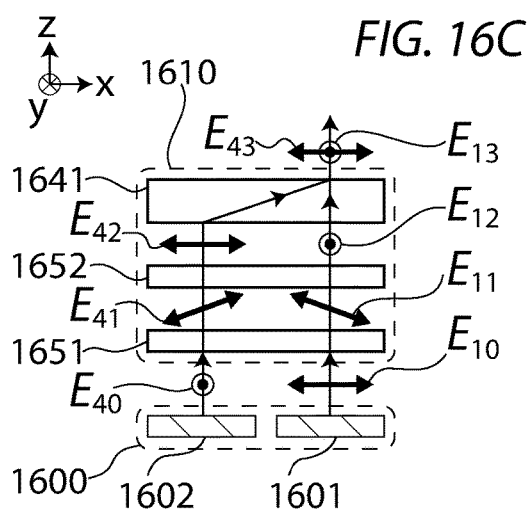
FIG. 16C shows a side view of a polarization transformation-separation configuration for use with a four-waveguide polarization-diversified free-sp ace-to-waveguide coupler for out-coupling optical signals, in accordance with another embodiment of the present disclosure.
Figure 16D:
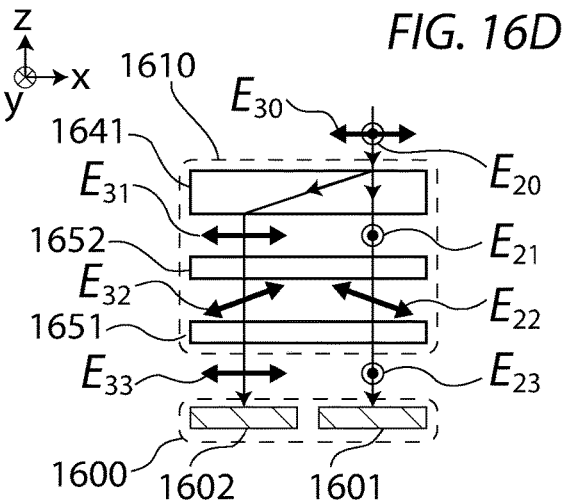
FIG. 16D shows a side view of the configuration illustrated in FIG. 16C used for in-coupling optical signals.
Figure 16E:
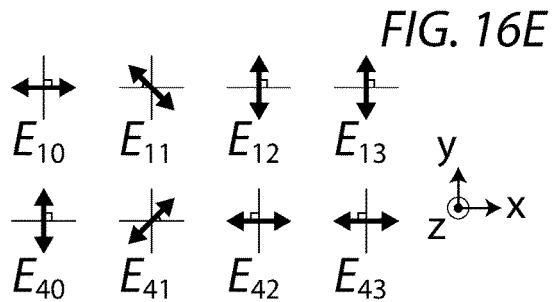
FIG. 16E shows a top view of the polarization states of the optical signals in FIG. 16C.
Figure 16F:
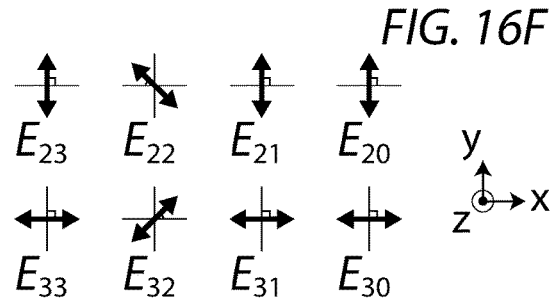
FIG. 16F shows a top view of the polarization states of the optical signals in FIG. 16D.

FIG. 16C shows a side view of a polarization transformation-separation configuration 1610 for use with four-waveguide polarization-diversified free-space-to-wave guide coupler 1600 for out-coupling optical signals, in accordance with another embodiment of the present disclosure. FIG. 16D shows a side view of configuration 1610 illustrated in FIG. 16C used for in-coupling optical signals. For illustrative purpose, FIG. 16E shows a top view of the polarization states of the optical signals in FIG. 16C, while FIG. 16F shows a top view of the polarization states of the optical signals in FIG. 16D. Polarization transformation-separation configuration 1610 is essentially the same as polarization transformation-separation configuration 1010 as illustrated in FIGS. 10C and 10D. Embodiments of the optical paths and the polarization states of the outgoing optical signals arising from optical signals $E_1$ and $E_4$ and the incoming optical signals that give rise to optical signals $E_2$ and $E_3$ are shown in FIGS. 16C, 16D, 16E, and 16F. For simplicity, waveguides 1421, 1422, 1432, and 1433 are not shown explicitly in FIGS. 16C and 16D.

In FIGS. 16B, 16C, and 16D, for illustrative purpose, the optical signals are depicted to propagate along the z direction and are at normal incident on coupler 1600, polarization-dependent beam-separator 1641, Faraday rotator 1651, and polarization rotator 1652. In general, the propagation directions of the optical signals may be at normal incidence or at incident angles other than normal incidence with respect to these components.

FIG. 17A shows a perspective view of a four-waveguide polarization-diversified free-space-to-waveguide coupler 1700 (herein referred to as coupler 1700 for simplicity), in accordance with a further embodiment of the present disclosure. FIG. 17A additionally shows polarized outgoing and incoming optical signals $E_{01}$, $E_{04}$, $E_{24}$, and $E_{34}$ coupling with sub-couplers 1701, 1702, and 1703. Coupler 1700, as indicated by the dash line in FIG. 17A, comprises three sub-couplers 1701, 1702, and 1703. According to some embodiments, sub-coupler 1701 may be realized by either polarization-diversified free-space-to-waveguide coupler 101 as illustrated in FIG. 1B or polarization-diversified free-space-to-waveguide coupler 200 as illustrated in FIG. 2, whereas each of sub-couplers 1702 and 1703 may be realized by a free-space-to-waveguide coupler, including but not limited to a grating coupler, that is coupled to a single waveguide. According to other embodiments, each of sub-couplers 1702 and 1703 may be realized by a polarization-independent free-space-to-waveguide coupler. Coupler 1700 is a modified embodiment of coupler 1100 as illustrated in FIG. 11A, with an additional waveguide 1432 connecting to sub-coupler 1701 of coherent sensing unit 1700 in FIG. 17A for out-coupling optical signal $E_4$ in addition to the out-coupling of optical signal $E_1$ from waveguide 1421.

In FIG. 17A, for illustrative purpose, outgoing optical signal $E_{01}$ and outgoing optical signal $E_{04}$ are drawn to couple with sub-coupler 1701 at different spatial locations. According to some embodiments, outgoing optical signal $E_{01}$ and outgoing optical signal $E_{04}$ may couple with sub-coupler 1701 at the same spatial locations so as to ensure maximal spatial overlap of the two outgoing optical signals. According to other embodiments, outgoing optical signal $E_{01}$ and outgoing optical signal $E_{04}$ may couple with sub-coupler 1701 at different spatial locations.

FIG. 17B show a side view of a polarization transformation-separation configuration 1710 for use with four-waveguide polarization-diversified free-space-to-wave guide coupler 1700 for out-coupling optical signals, in accordance with a further embodiment of the present disclosure. FIG. 17C show a side view of configuration 1710 illustrated in FIG. 17B used for in-coupling optical signals. For illustrative purpose, FIG. 17D shows a top view of the polarization states of the optical signals in FIG. 17B, while FIG. 17E shows a top view of the polarization states of the optical signals in FIG. 17C. Polarization transformation-separation configuration 1710 is essentially the same as polarization transformation-separation configuration 1110 as illustrated in FIGS. 11B and 11C. Embodiments of the optical paths and the polarization states of the outgoing optical signals arising from optical signals $E_1$ and $E_4$ and the incoming optical signals that give rise to optical signals $E_2$ and $E_3$ are shown in FIGS. 17B, 17C, 17D, and 17E. The use of polarization transformation-separation configuration 1710 with coupler 1700 may ensure that the optical path length of the signals $E_{01}$, $E_{10}$, $E_{11}$, $E_{12}$, and $E_{13}$ is essentially the same as the optical path length of the signals $E_{04}$, $E_{40}$, $E_{41}$, $E_{42}$, and $E_{43}$, so that the polarization of the coherently combined optical signal from optical signals $E_{13}$ and $E_{43}$ is essentially the same as the polarization of the coherently combined optical signal from optical signals $E_{01}$ and EA. For simplicity, waveguides 1421, 1422, 1432, and 1433 are not shown explicitly in FIGS. 17B and 17C.

In FIGS. 17A, 17B, and 17C, for illustrative purpose, the optical signals are depicted to propagate along the z direction and are at normal incident on coupler 1700, polarization-dependent beam-separators 1741 and 1742, Faraday rotator 1751, and polarization rotator 1752. In general, the propagation directions of the optical signals may be at normal incidence or at incident angles other than normal incidence with respect to these components.

Figure 18A:
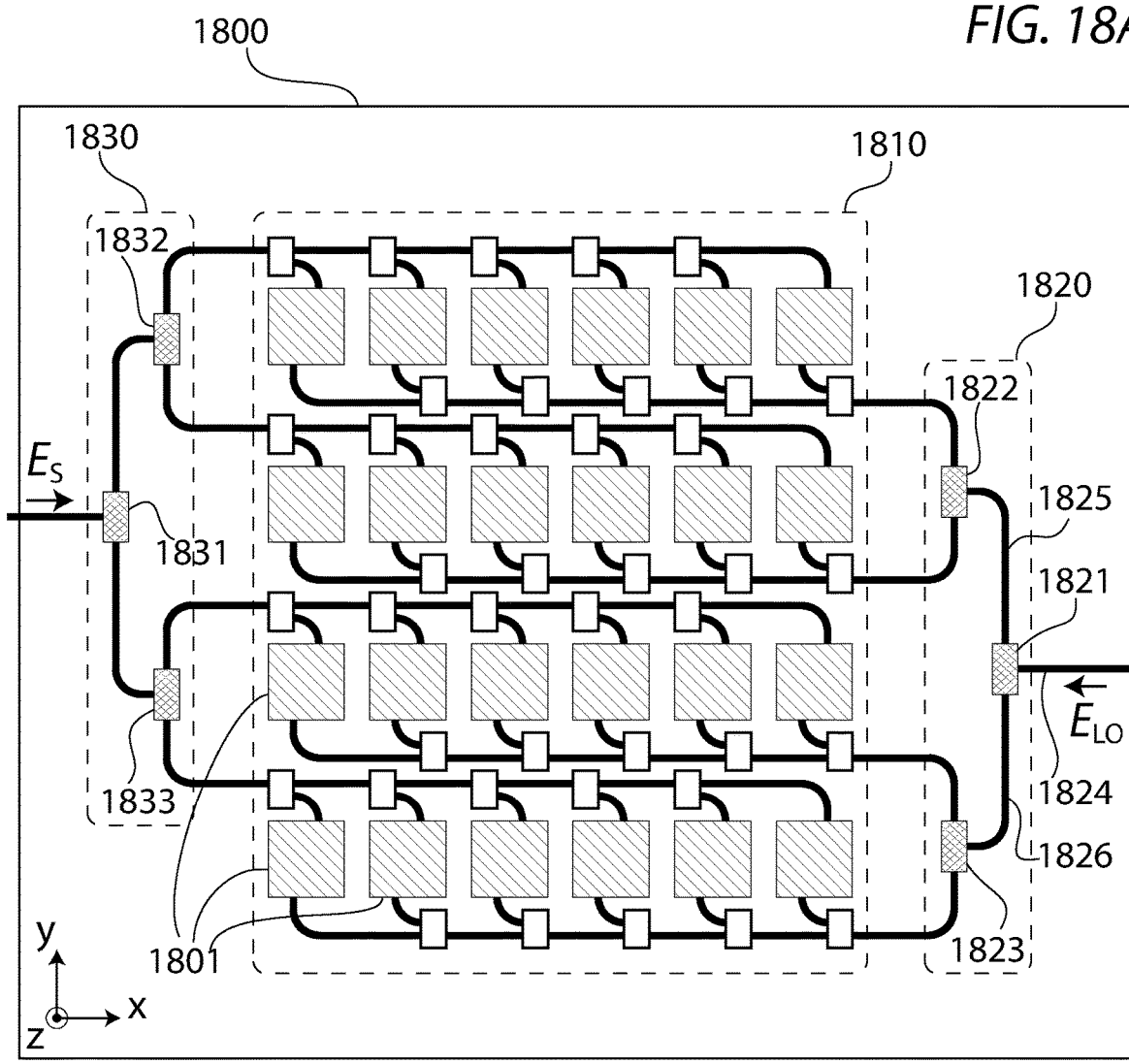
FIG. 18A shows a plan view of a coherent optical sensor, in accordance with an embodiment of the present disclosure.

FIG. 18A shows a plan view of a coherent optical sensor 1800 in accordance with an embodiment of the present disclosure. Coherent optical sensor 1800 comprises a coherent sensing array 1810 and optical routing circuits 1820 and 1830 that are implemented on a PIC chip.

In FIG. 18A, optical routing circuit 1820 is used for routing the LO $E_{LO}$ into coherent sensing array 1810. For example, optical routing circuit 1820 in FIG. 18A routes the LO $E_{LO}$ into the different rows of coherent sensing array 1810. Optical routing circuit 1820 comprises a network of optical waveguides wherein the flow of the LO $E_{LO}$ is controlled by a plurality of optical switches in the network. As an example, in FIG. 18A, optical routing circuit 1820 comprises optical switches 1821, 1822, and 1823, which may be, but not limited to, Mach-Zehnder interferometer (MZI)-based optical switches, or MEMS-based optical switches.

It is appreciated that other implementations of optical routing circuit 1820 are possible. For example, optical routing circuit 1820 in FIG. 18A may be in the form of a binary tree. An optical switch directs the LO $E_{LO}$ from an input to one or more output ports of the switch. According to some embodiments, optical switch 1821 in FIG. 18A may direct the LO $E_{LO}$ in waveguide 1824 to either one or both of waveguides 1825 and 1826.

Optical routing circuit 1830 is used for routing optical source signal $E_S$ into coherent sensing array 1810. According to some embodiments, optical routing circuit 1830 may exhibit a structure similar to that of optical routing circuit 1820. In one embodiment, optical routing circuit 1830 may be in the form of a binary tree comprising optical switches 1831, 1832, and 1833. According to other embodiments, optical routing circuit 1830 may exhibit a structure different from that of optical routing circuit 1820.

Figure 18B:
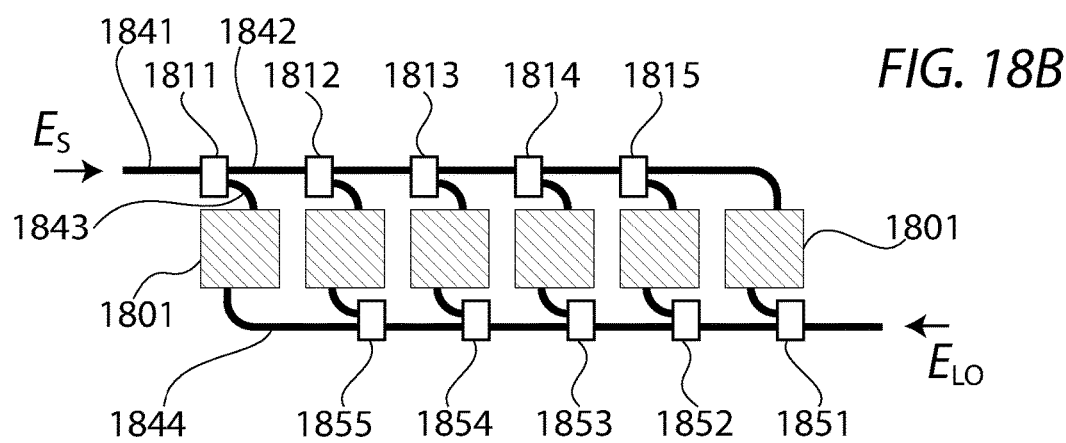
FIG. 18B shows a row of coherent sensing units of a coherent sensing array, in accordance with an embodiment of the present disclosure.

In FIG. 18A, coherent sensing array 1810 comprises an array of coherent sensing units 1801. In one embodiment, coherent sensing array 1810 comprises 24 coherent sensing units 1801 arranged in a 4×6 rectangular format (i.e., 4 rows and 6 columns). FIG. 18B shows a row of 6 coherent sensing units of coherent sensing array 1810, in accordance with an embodiment of the present disclosure.

In FIG. 18A, each coherent sensing unit 1801 of coherent sensing array 1810 is connected to two waveguides that function as optical input ports for the coherent sensing unit. According to some embodiments, coherent sensing unit 1801 may be coherent sensing unit 100 as illustrated in FIG. 1A. According to other embodiments, coherent sensing unit 1801 may be coherent sensing unit 700 as illustrated in FIG. 7A. According to yet other embodiments, coherent sensing unit 1801 may be coherent sensing unit 800 as illustrated in FIG. 8. According to further embodiments, coherent sensing unit 1801 may be coherent sensing unit 900 as illustrated in FIG. 9.

In FIG. 18A, the two waveguides that are connected to coherent sensing unit 1801 may be used to direct optical source signal $E_S$ and the LO $E_{LO}$ into that sensing unit 1801. For example, with reference to FIG. 18B, waveguide 1843 may be used to direct optical source signal $E_S$ into coherent sensing unit 1801 that is connected to waveguides 1843 and 1844 in FIG. 18B, whereas waveguide 1844 may be used to direct the LO $E_{LO}$ into the same coherent sensing unit. Splitting couplers may be used in coherent sensing array 1810 to distribute optical source signal $E_S$ and the LO $E_{LO}$ into different coherent sensing units 1801. As shown in FIG. 18B, splitting couplers 1811, 1812, 1813, 1814, and 1815 may be used to distribute optical source signal $E_S$ into the six coherent sensing units 1801. Splitting couplers 1811, 1812, 1813, 1814. and 1815 may have the same or different splitting ratios. According to some embodiments that distribute the optical source signal $E_S$ evenly into the six coherent sensing units 1801, splitting coupler 1811 may have a splitting ratio of 5:1, splitting coupler 1812 may have a splitting ratio of 4:1, splitting coupler 1813 may have a splitting ratio of 3:1, splitting coupler 1814 may have a splitting ratio of 2:1, and splitting coupler 1815 may have a splitting ratio of 1:1. Similarly, according to the embodiment in FIG. 18B, splitting couplers 1851, 1852, 1853, 1854, and 1855 may be used to distribute the LO $E_{LO}$ into the six coherent sensing units 1801, wherein splitting couplers 1851, 1852, 1853, 1854, and 1855 are similar to splitting couplers 1811, 1812, 1813, 1814, and 1815 that may or may not evenly distribute the LO $E_{LO}$ to the six coherent sensing units 1801.

Coherent optical sensor 1800 in FIG. 18A may also comprise laser sources, electrical control circuits, and electrical readout circuits that are not shown explicitly in the figure.

Figure 19A:
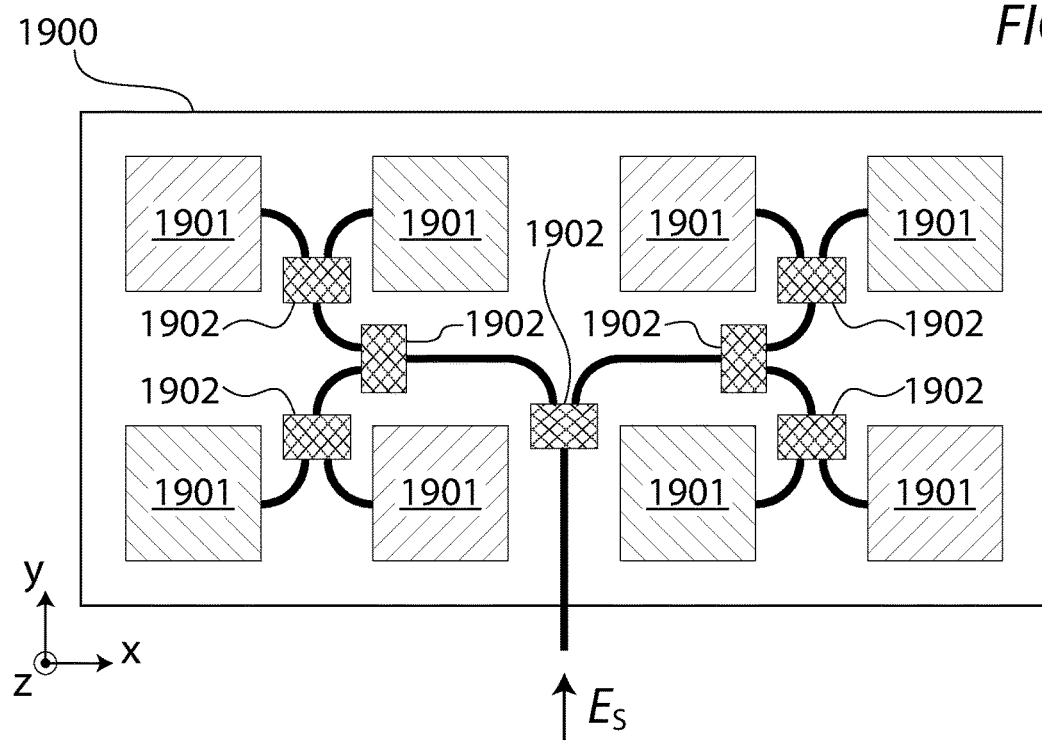
FIG. 19A shows a plan view of a coherent optical sensor, in accordance with another embodiment of the present disclosure.

FIG. 19A shows a plan view of a coherent optical sensor 1900, in accordance with another embodiment of the present disclosure. Coherent optical sensor 1900 comprises an array of coherent sensing units 1901 that are coupled to optical source signal $E_S$ through an optical routing circuit in the topology of an H-tree. For example, coherent optical sensor 1900 as shown in FIG. 19A manifests as a three-level H-tree with eight coherent sensing units 1901. The H-tree optical routing circuit in coherent optical sensor 1900 is constructed by a network of waveguides that are coupled with a plurality of optical switches 1902. Optical switches 1902 in FIG. 19A may be similar to optical switches 1821, 1822, 1823, 1831, 1832, and 1833 of coherent optical sensor 1800 in FIG. 18A.

Figure 19B:
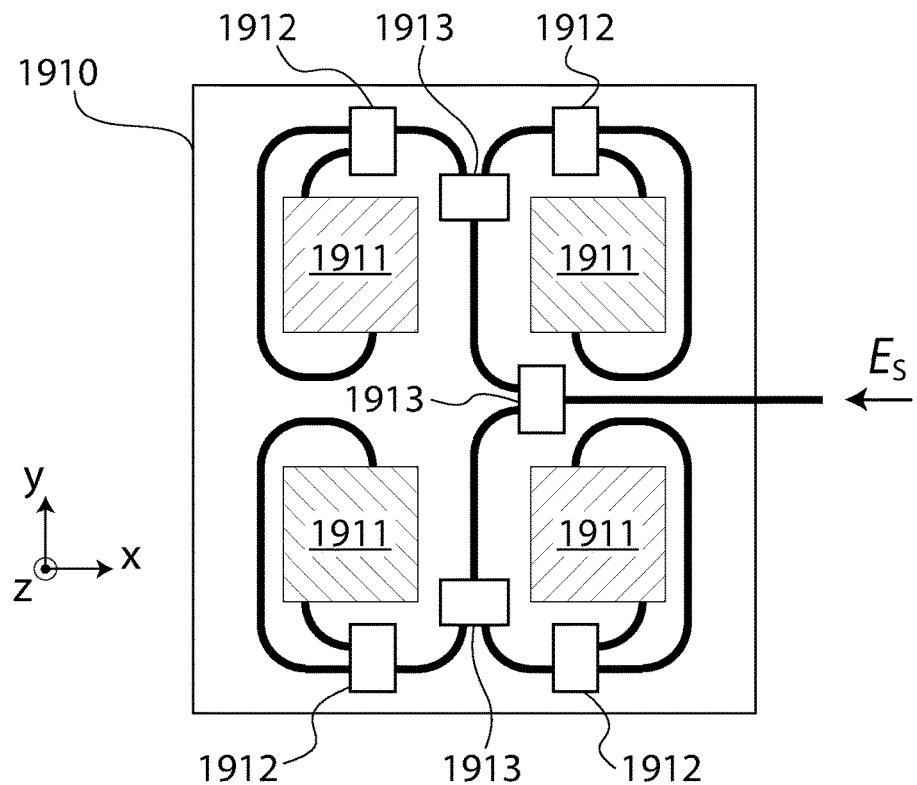
FIG. 19B shows a plan view of a coherent sensing unit group, in accordance with an embodiment of the present disclosure.

As illustrated in FIG. 19A, each of coherent sensing units 1901 may be coupled to a single waveguide that supplies optical source signal $E_S$ to the coherent sensing unit. The optical source signal $E_S$ may be used as both the optical source signal for target illumination and the LO for heterodyne detection in a coherent sensing unit 1901. According to some embodiments, each of coherent sensing units 1901 may be a coherent sensing unit 710 as illustrated in FIG. 7B. According to other embodiments, each of coherent sensing units 1901 may be a coherent sensing unit 100 as illustrated in FIG. 1A, a coherent sensing unit 700 as illustrated in FIG. 7A, a coherent sensing unit 800 as illustrated in FIG. 8, or a coherent sensing unit 900 as illustrated in FIG. 9, wherein a splitting coupler may be used to split optical source signal $E_S$ that is supplied to each coherent sensing unit 1901 into a fraction of optical source signal $E_S$ that is used as the source signal and a fraction of $E_S$ that is used as the LO $E_{LO}$ for the coherent sensing unit. According to further embodiments, each of coherent sensing units 1901 may be a coherent sensing unit group 1910 as illustrated in FIG. 19B. Coherent optical sensor 1900 in FIG. 19A may also comprise laser sources, electrical control circuits, and electrical readout circuits that are not shown explicitly in the figure.

FIG. 19B shows a plan view of a coherent sensing unit group 1910, in accordance with an embodiment of the present disclosure. In one embodiment, coherent sensing unit group 1910 comprises a plurality of coherent sensing units 1911 arranged in an H-tree topology. For example, coherent optical sensor 1910 in FIG. 19B manifests as a two-level H-tree with four coherent sensing units 1911. In FIG. 19B, components 1913 are splitting couplers that may be used to split optical source signal $E_S$ so as to supply a fraction of optical source signal $E_S$ to each of coherent sensing units 1911 of coherent sensing unit group 1910. According to some embodiments, the splitting ratios of splitting couplers 1913 may be 50/50 so as to distribute the source signal evenly to all coherent sensing units 1911 of coherent sensing unit group 1910. In FIG. 19B, components 1912 are splitting couplers that may be used to split optical source signal $E_S$ that is supplied to each coherent sensing unit 1911 into a fraction of optical source signal $E_S$ as the optical source signal and a fraction of optical source signal $E_S$ as the LO for the coherent sensing unit. The splitting ratio of splitting coupler 1912 may or may not be 50/50.

In FIG. 19B, each of coherent sensing unit 1911 may be coherent sensing unit 100 as illustrated in FIG. 1A, coherent sensing unit 700 as illustrated in FIG. 7A, coherent sensing unit 800 as illustrated in FIG. 8, or coherent sensing unit 900 as illustrated in FIG. 9.

Figure 20A:
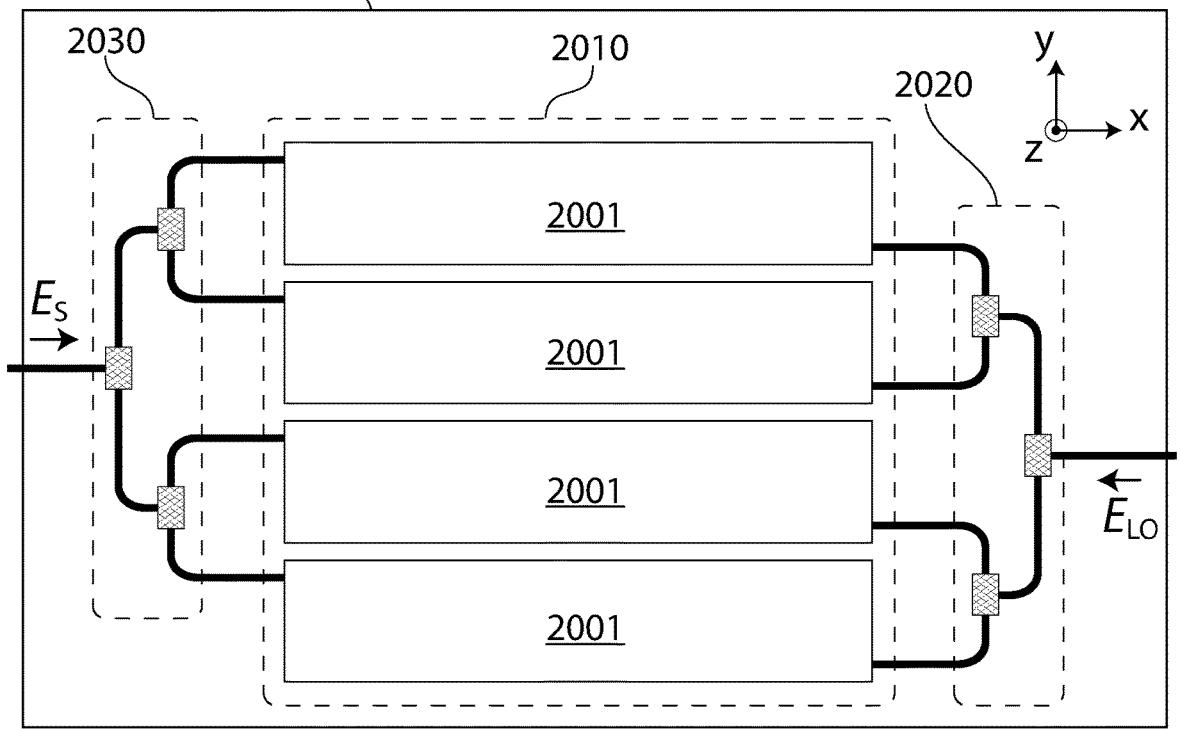
FIG. 20A shows a plan view of a coherent optical sensor, in accordance with a further embodiment of the present disclosure.

FIG. 20A shows a plan view of a coherent optical sensor 2000, in accordance with a further embodiment of the present disclosure. Coherent optical sensor 2000 comprises a sensing region 2010 and optical routing circuits 2020 and 2030 that are implemented on a PIC chip. According to some embodiments, sensing region 2010 comprises a plurality of coherent sensing unit groups 2001. Each coherent sensing unit group 2001 comprises a plurality of coherent sensing units that emit outgoing optical signals for target illumination wherein the polarization of the outgoing optical signals is adjustable.

In FIG. 20A, optical routing circuit 2020 may be used for routing the local oscillator $E_{LO}$ to coherent sensing unit groups 2001 in sensing region 2010. According to some embodiments, optical routing circuit 2020 may be similar to optical routing circuit 1820 of coherent optical sensor 1800. In FIG. 20A, optical routing circuit 2030 may be used for routing source light $E_S$ to coherent sensing unit groups 2001 in sensing region 2010. According to some embodiments, optical routing circuit 2030 may be similar to optical routing circuit 1830 of coherent optical sensor 1800.

Figure 20B:
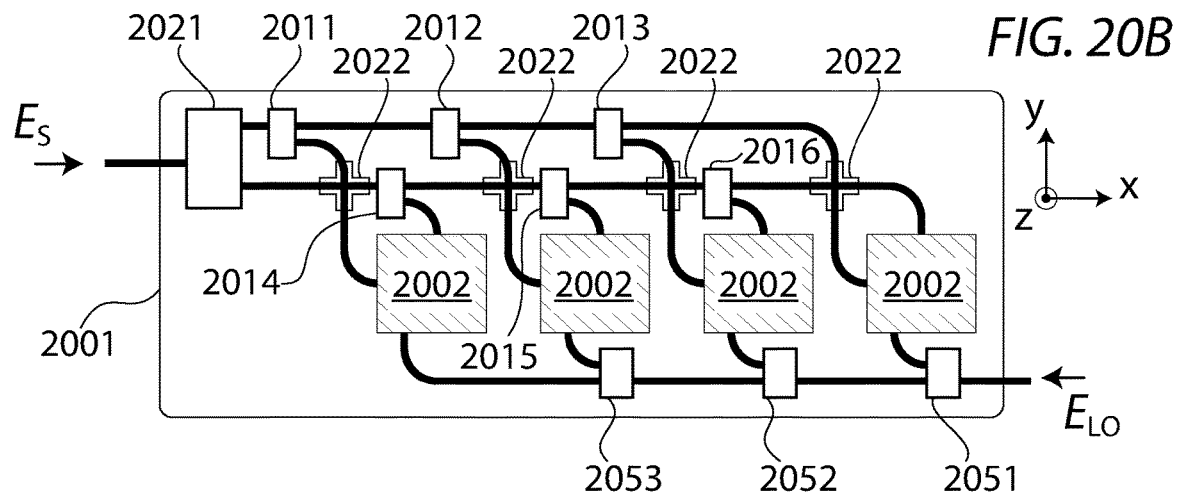
FIG. 20B shows a plan view of a coherent sensing unit group, in accordance with an embodiment of the present disclosure.

FIG. 20B shows a plan view of a coherent sensing unit group 2001, in accordance with another embodiment of the present disclosure. Coherent sensing unit group 2001 comprises a plurality of coherent sensing units 2002 that emit outgoing optical signals with adjustable polarizations for target illumination. For illustrative purpose, coherent sensing unit group 2001 is drawn to comprise four coherent sensing units 2002 in FIG. 20B. Each coherent sensing unit 2002 comprises one input waveguide for in-coupling the LO $E_{LO}$ and two input waveguides for in-coupling source light, wherein the amplitudes and the relative phase of the source light in the two waveguides determine the polarization state of the outgoing optical signal emitted from coherent sensing unit 2002. According to some embodiments, a coherent sensing unit 2002 may be realized by coherent sensing unit 1400 as illustrated in FIG. 14.

As illustrated in FIG. 20B, each coherent sensing unit group 2001 comprises a plurality of splitting couplers 2051, 2052, and 2053 to distribute the LO $E_{LO}$ to each of coherent sensing units 2002 of coherent sensing unit group 2001. According to some embodiments, splitting couplers 2051, 2052, and 2053 may be similar to splitting couplers 1851, 1852, 1853, 1854, and 1855 that may or may not distribute the LO $E_{LO}$ evenly to each coherent sensing unit 2002 of coherent sensing unit group 2001.

As illustrated in FIG. 20B, each coherent sensing unit group 2001 may comprise an optical switch 2021 that divides source light $E_S$ into two fractions. The two fractions of source light $E_S$ may then be distributed to each coherent sensing unit 2002 through splitting couplers. For example, a fraction of source light $E_S$ may be distributed to coherent sensing units 2002 through splitting couplers 2011, 2012, and 2013. According to some embodiments, splitting couplers 2011, 2012, and 2013 may be similar to splitting couplers 1811, 1812, 1813, 1814, and 1815 that may or may not distribute source light $E_S$ evenly to each coherent sensing unit 2002 of coherent sensing unit group 2001. Similarly, a fraction of source light $E_S$ may be distributed to each coherent sensing unit 2002 through splitting couplers 2014, 2015, and 2016 that are similar to splitting couplers 2011, 2012, and 2013. According to some embodiments, coherent sensing unit group 2001 may comprise waveguide crossings 2022 to enable optical signals to cross each other with minimal loss and cross-talk in a compact PIC layout.

Figure 20C:
FIG. 20C shows a plan view of a Mach-Zehnder interferometer-based optical switch in accordance with an embodiment of the present disclosure.

FIG. 20C shows a plan view of a Mach-Zehnder interferometer-based optical switch 2021, in accordance with an embodiment of the present disclosure. Optical switch 2021, which is a Mach-Zehnder interferometer, includes a phase shifter 2031 to control the output fractions of optical switch 2021. According to some embodiments, phase shifter 2031 may be an electro-optic phase shifter or a thermo-optic phase shifter.

Coherent optical sensor 2000 in FIG. 20A may comprise laser sources, electrical control circuits, and electrical readout circuits that are not shown explicitly. Also, coherent sensing unit group 2001 in FIG. 20B may comprise electrical control circuits and electrical readout circuits that are not shown explicitly.

Figure 21A:
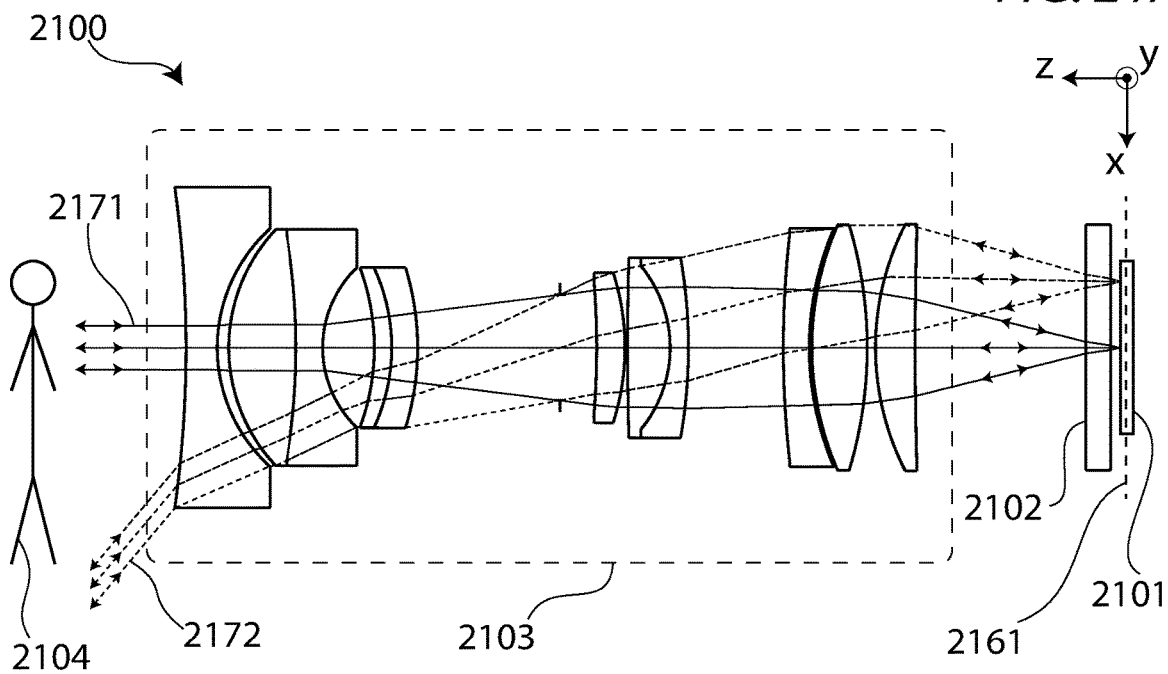
FIG. 21A shows a side view of an optical coherent imager, in accordance with an embodiment of the present disclosure.

FIG. 21A shows a side view of an optical coherent imager 2100, in accordance with an embodiment of the present disclosure. Optical coherent imager 2100 comprises a coherent optical sensor 2101, a polarization transformation-separation assembly 2102, and an imaging optics system 2103. Optical coherent imager 2100 may also comprise other components including but not limited to any one or more of laser sources, electronic controllers, electronic interfaces, and digital signal processors that are not shown explicitly in FIG. 21A for simplicity.

Coherent optical sensor 2101 in FIG. 21A is a sensor comprising a plurality of coherent sensing units of the present disclosure. According to some embodiments, coherent optical sensor 2101 may be one of coherent optical sensors 1800, 1900, and 2000 respectively illustrated in FIGS. 18A, 19A, and 20A. Outgoing optical signals are emitted from coherent optical sensor 2101 for target illumination. Outgoing optical signals emitted from different coherent sensing units of coherent optical sensor 2101 through imaging optics system 2103 may give rise to illuminating beams of different field-of-view positions, so that each field-of-view position corresponds to a coherent sensing unit of the coherent optical sensor. The details of imaging optics system 2103 in FIG. 21A are shown only for illustrative purpose. Other optical setups may be used for imaging optics system 2103. Depending on the specific design of coherent sensing units used in coherent optical sensor 2101, according to some embodiments, polarization transformation-separation assembly 2102 may be one of the configurations shown in FIGS. 4C, 5A, 5C, 6A, 6C, 10C, 11B, 12A, 13C, 15C, 16C, and 17B. Polarization transformation-separation assembly 2102 may be used to enable the outgoing optical signals emitted from coherent optical sensor 2101 for target illumination and the incoming optical signals (i.e., target signals) received by coherent optical sensor 2101 to propagate along common optical paths, wherein the common optical paths lie between assembly 2102 and target 2104.

In FIG. 21A, light rays 2171 illustrate example optical paths of a field-of-view position of optical coherent imager 2100, and light rays 2172 illustrate example optical paths of another field-of-view position of optical coherent imager 2100. Imaging optics system 2103 may have at least one image plane. Polarization transformation-separation assembly 2102 may be disposed at a location proximate an image plane of imaging optics system 2103. For example, in FIG. 21A, polarization transformation-separation assembly 2102 is disposed at a location proximate coherent optical sensor 2101, which is disposed at the final image plane 2161 of imaging optics system 2103.

Figure 21B:
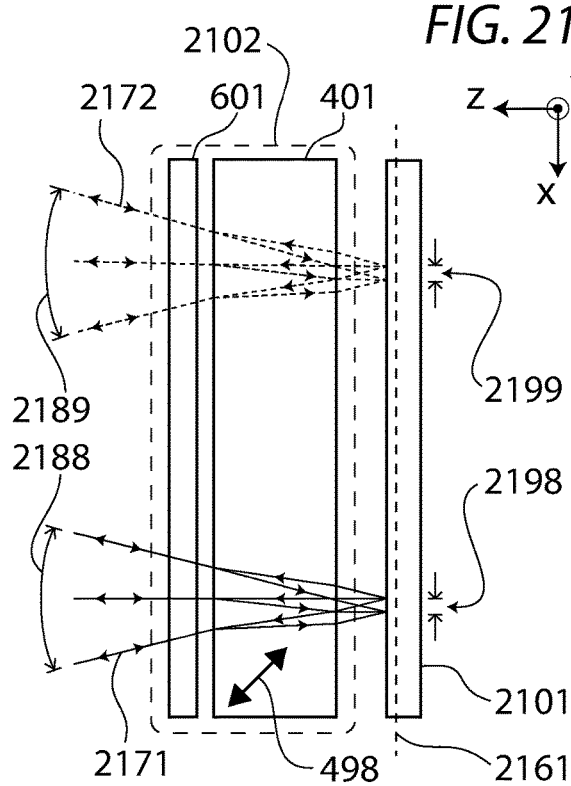
FIG. 21B shows a closeup view of the imager in FIG. 21A near the final image plane.

FIG. 21B shows a closeup view of imager 2100 in FIG. 21A near the final image plane 2161. For illustrative purpose, in FIG. 21B, polarization transformation-separation assembly 2102 may be manifested as the polarization transformation-separation configuration illustrated in FIG. 6C. As illustrated in FIG. 21B, for each of the field-of-view positions of optical coherent imager 2100, incoming optical signals from the target that share common optical paths with respect to outgoing optical signals may be spatially separated on the final image plane by polarization-dependent beam-separator 401. In FIG. 21B, spatial separation 2198 is the spatial separation of the incoming and outgoing light rays 2171 effected by polarization-dependent beam-separator 401, and spatial separation 2199 is the spatial separation of the incoming and outgoing light rays 2172 effected by polarization-dependent beam-separator 401. According to some embodiments, imaging optics system 2103 may possess image space telecentricity that enables the spatial separations by polarization-dependent beam-separator 401 to be uniform across the field of view of optical coherent imager 2100. Spatial separation 2198 of light rays 2171 may thus be similar to spatial separation 2199 of light rays 2172. Additionally, angular subtense 2188 of light rays 2171 may also be similar to angular subtense 2189 of light rays 2172. In such a circumstance, the polarization-diversified free-space-to-waveguide couplers of the coherent sensing units in coherent optical sensor 2101 may be designed to optimally couple with optical signals according to a common incident angle (e.g., normal incidence), a common angular subtense and, if applicable, a common separation between sub-couplers. According to other embodiments wherein imaging optics system 2103 may not possess image space telecentricity, each of the polarization-diversified free-space-to-waveguide couplers of the coherent sensing units in coherent optical sensor 2101 may be designed individually to optimally couple with optical signals according to the specifications of polarization transformation-separation assembly 2102 and imaging optics system 2103.

Figure 21C:
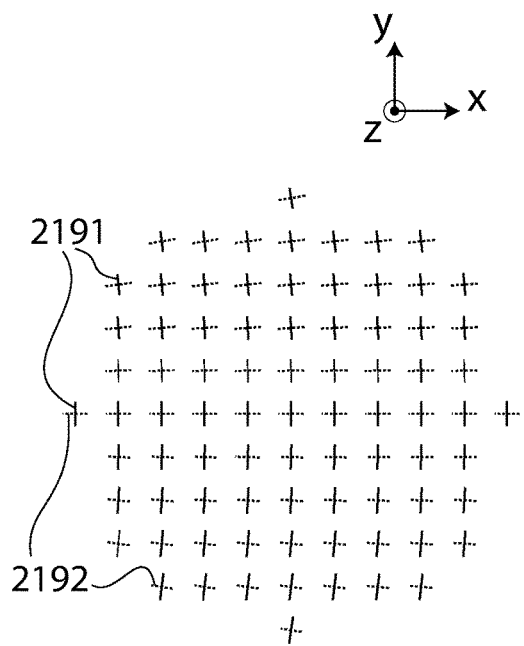
FIG. 21C shows a polarization map of example ordinary rays and extraordinary rays on the final image plane over the field of view of the optical coherent imager in FIG. 21B.

FIG. 21C shows a polarization map of example ordinary rays (o-rays) and extraordinary rays (e-rays) with respect to polarization-dependent beam-separator 401 on coherent optical sensor 2101 over the field of view of the optical coherent imager in FIG. 21B. In FIG. 21C, polarizations 2191 illustrate examples of the o-ray polarizations, and polarizations 2192 illustrate examples of the e-ray polarizations. As an example, according to the orientation of optic axis 498 which lies on the x-z plane in FIG. 21B, the o-ray polarizations are linear polarizations that have dominant components along the y direction, whereas the e-ray polarizations are linear polarizations that have dominant components along the x direction. According to some embodiments wherein imaging optics system 2103 is exactly image-space telecentric, both the o-ray and e-ray polarizations may be unform over the field of view of the optical coherent imager. According to other embodiments, such as the embodiment illustrated in FIG. 21C, the polarizations of the o-rays and e-rays may depart from uniformity when imaging optics system 2103 is not exactly image-space telecentric. According to some embodiments, the polarization-diversified free-space-to-waveguide couplers of the coherent sensing units in coherent optical sensor 2101 may be designed wherein the non-uniformity is ignored. According to other embodiments, each of the polarization-diversified free-space-to-waveguide couplers of the coherent sensing units in coherent optical sensor 2101 may be designed individually to optimally couple with optical signals according to the variations of the polarizations of the o-rays and e-rays over the field of view of imaging optics system 2103.

Figure 22A:
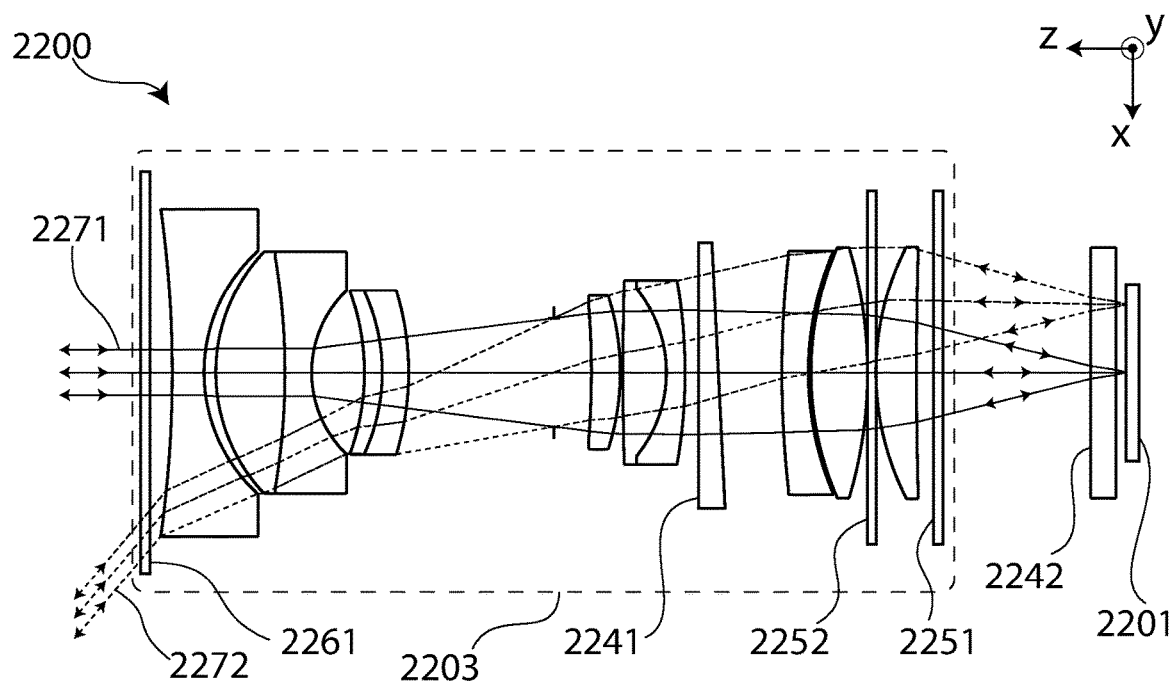
FIG. 22A shows a side view of an optical coherent imager, in accordance with another embodiment of the present disclosure.

FIG. 22A shows a side view of an optical coherent imager 2200, in accordance with another embodiment of the present disclosure. Optical coherent imager 2200 comprises a coherent optical sensor 2201, an imaging optics system 2203, and a polarization transformation-separation assembly with components disposed with the optical components of imaging optics system 2203. As an illustration, the polarization transformation-separation assembly comprises polarization-dependent beam-separators 2241 and 2242, Faraday rotator 2251, polarization rotator 2252, and quarter-wave plate 2261. This polarization transformation-separation assembly is similar to polarization transformation-separation configuration 1210 in FIGS. 12A and 12B, except for the use of a polarization-dependent beam-separator 2241 that effects angular displacements instead of lateral displacements effected by polarization-dependent beam-separator 1241 in configuration 1210. According to some embodiments, polarization-dependent beam-separator 2241 may be a birefringent wedge. In FIG. 22A, light rays 2271 illustrate example optical paths of a field-of-view position of optical coherent imager 2200, and light rays 2272 illustrate example optical paths of another field-of-view position of optical coherent imager 2200.

Figure 22B:
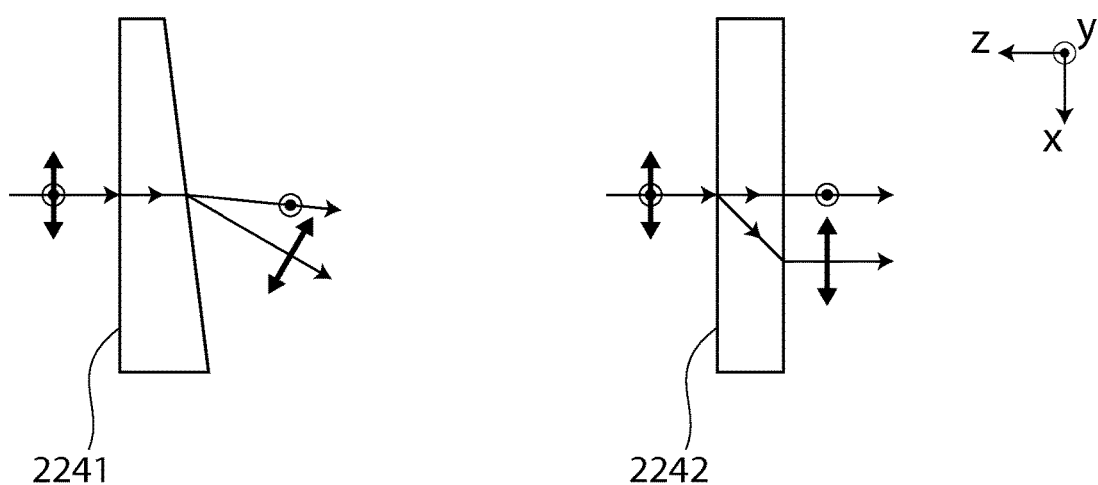
FIG. 22B shows side views of light rays propagating through a polarization-dependent beam-separator that effects angular displacement and light rays propagating through a polarization-dependent beam-separator that effects lateral displacement, in accordance with embodiments of the present disclosure.

FIG. 22B shows side views of light rays propagating through a polarization-dependent beam-separator 2241 that effects angular displacement and light rays propagating through a polarization-dependent beam-separator 2242 that effects lateral displacement, in accordance with embodiments of the present disclosure. With reference to FIG. 22B, polarization-dependent beam-separator 2242 may give rise to a lateral displacement to an incoming light ray with the lateral displacement depending on the polarization of the light ray. For example, in FIG. 22B, the x polarization component and the y polarization component of a light ray is laterally displaced with different displacements when the light ray passes through polarization-dependent beam-separator 2242. In contrast, polarization-dependent beam-separator 2241 may give rise to an angular displacement to an incoming light ray with the angular displacement depending on the polarization of the light ray. For example, in FIG. 22B, the x polarization component and the y polarization component of a light ray is angularly displaced at different angles when the light ray passes through polarization-dependent beam-separator 2241.

Referring back to FIG. 22A, polarization-dependent beam-separator 2242 is disposed at a location proximate an image plane of imaging optics system 2203, whereas polarization-dependent beam-separator 2241 is disposed at a location proximate a focal plane of imaging optics system 2203. Angular displacements by polarization-dependent beam-separator 2241 on the focal plane may effectively give rise to lateral displacements on the image plane. The use of polarization-dependent beam-separator 2241 may have an advantage of enabling a greater flexibility in various locations for disposing optical components, including but not limited to polarization-dependent beam-separators 2241 and 2242, Faraday rotator 2251, polarization rotator 2252, and quarter-wave plate 2261, in imaging optics system 2203.

As shown in FIG. 22A, Faraday rotator 2251, polarization rotator 2252, and quarter-wave plate 2261 may be disposed at locations in imaging optics system 2203 where the incident angles of light rays are relatively small (i.e., close to normal incidence). According to some embodiments, some polarization-dependent components may have larger performance tolerances than others for certain applications of optical coherent imaging. For example, Faraday rotator 2251 that is tolerant to the incident angles of light rays may be disposed at any location between polarization rotator 2252 and polarization-dependent beam-separators 2242. As another example, quarter-wave plate 2261 may be disposed at a location where there is a larger variation in the incident angles of light rays at different field-of-view positions. Quarter-wave plate 2261 may transform a linearly-polarized outgoing optical signal at normal incidence to a circularly-polarized optical signal, and a linearly-polarized outgoing optical signal at an incident angle other than normal incidence to an elliptically-polarized optical signal. The consequence of the variations in incident angle on quarter-wave plate 2261 at different field-of-view positions may thus essentially result in different elliptically-polarized light for the illumination of different positions of the target scene, which may not impose significant issue for the relevant applications of optical coherent imaging. Additionally, some embodiments of coherent optical sensor 2201, such as coherent optical sensor 2000 illustrated in FIG. 20A, may enable dynamical polarization adjustment, which may mitigate the issue of the different elliptically-polarized light for the illumination of different positions of the target scene.

In FIG. 22A, the components of the polarization transformation-separation assembly are individually disposed with the optical components of imaging optics system 2203. According to some embodiments, one or more of the components of the polarization transformation-separation assembly may be disposed collectively with the optical components of imaging optics system 2203.

Figure 23:
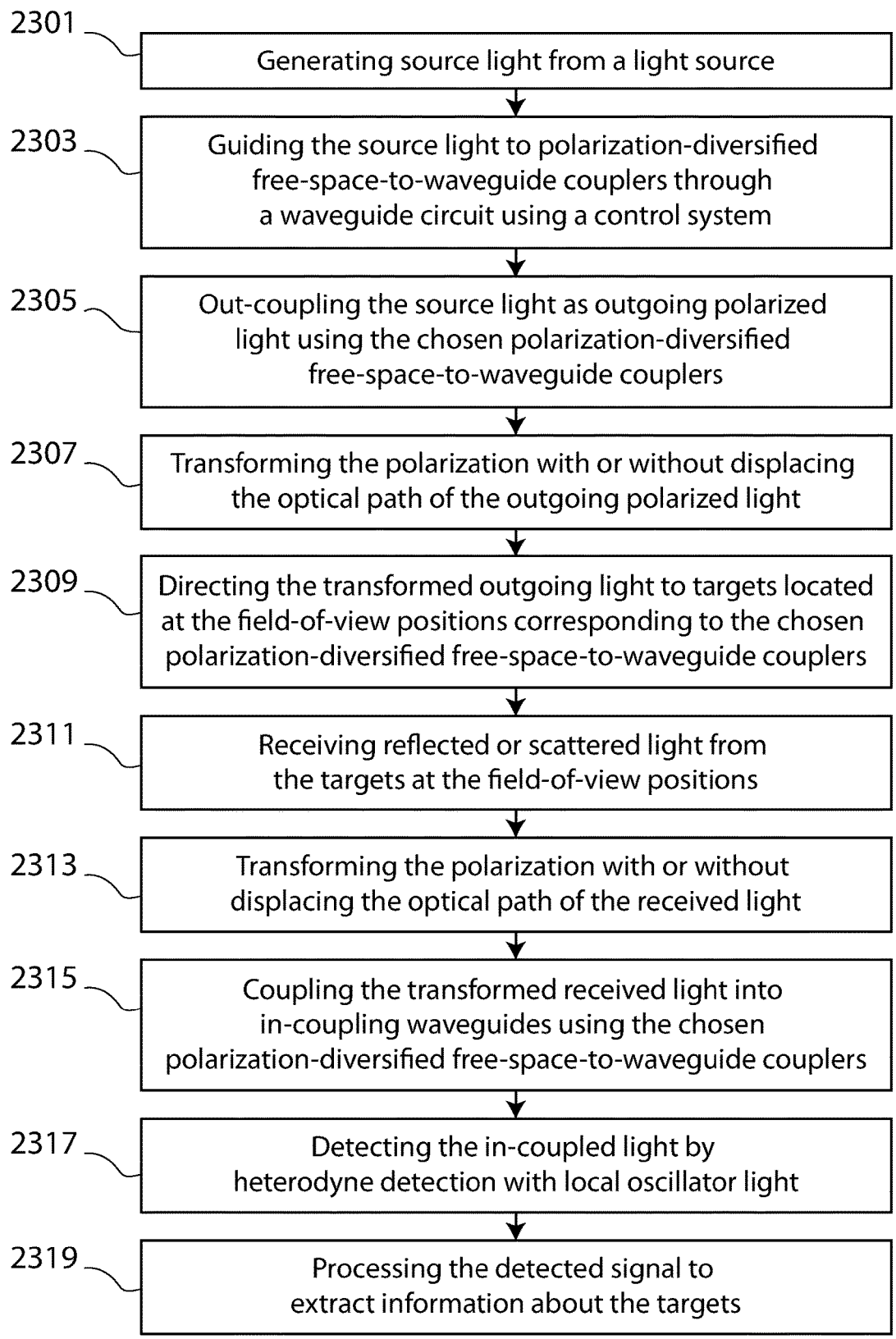
FIG. 23 illustrates a flowchart of a method of optical coherent imaging using polarization diversification to enable shared path for transmitting and receiving optical signals, in accordance with an embodiment of the present disclosure.

FIG. 23 illustrates a flowchart of a method of optical coherent imaging using polarization diversification to enable shared path for transmitting and receiving optical signals, in accordance with an embodiment of the present disclosure.

In Step 2301, source light is generated from a light source.

In Step 2303, the source light is guided through a waveguide circuit to one or more polarization-diversified free-space-to-waveguide couplers in a coherent optical sensor of an optical coherent imager. According to some embodiments, the guiding of the source light through the waveguide circuit may be accomplished by controlling electro-optical or thermo-optical switches in the waveguide circuit using a control system. According to some embodiments, the choice of the polarization-diversified free-space-to-waveguide couplers to which the source light is guided may be determined by the positions of a target scene to be illuminated. More specifically, each target scene position corresponds to a field-of-view position of the optical coherent imager, which in turn corresponds to a polarization-diversified free-space-to-waveguide coupler in the coherent optical sensor of the optical coherent imager.

In Step 2305, for each of the chosen polarization-diversified free-space-to-waveguide couplers (herein referred to as the couplers for simplicity) to which the source light is guided, the source light is out-coupled into free space from the coupler to give rise to outgoing light with a first polarization. Here, free space may refer to vacuum, air, a region above the surface of the coupler, or any homogenous medium with boundaries that have length-scales much larger (e.g., at least 10 times) than the wavelength of the optical signals propagating in it. According to some embodiments, the polarization-diversified free-space-to-waveguide coupler may be realized by coupler 101 shown and described with respect to FIG. 1B, coupler 200 shown and described with respect to FIG. 2, coupler 300 shown and described with respect to FIG. 3, coupler 1000 shown and described with respect to FIG. 10A, coupler 1100 shown and described with respect to FIG. 11A, coupler 1300 shown and described with respect to FIG. 13A, coupler 1500 shown and described with respect to FIG. 15A, coupler 1600 shown and described with respect to FIG. 16A, or coupler 1700 shown and described with respect to FIG. 17A.

In Step 2307, for the outgoing light emitted by each of the chosen polarization-diversified free-space-to-waveguide couplers, the first polarization of the outgoing light may be transformed to a second polarization by a polarization transformation configuration. The second polarization may be the same or different from the first polarization. The second polarization may be any of a linear polarization, a circular polarization, or an elliptical polarization. According to some embodiments, the polarization transformation may be realized by one or a combination of optical components including but not limited to Faraday rotator, polarization rotator, and quarter-wave plate.

In Step 2307, according to some embodiments, the optical path of the outgoing light may additionally be laterally or angularly displaced, or both laterally and angularly displaced. The displacement may be realized by at least one of optical-path-displacing components such as but not limited to polarization-dependent beam-separator. According to some embodiments, the operations of polarization transformation and optical path displacement may be realized by a combination of optical components including but not limited to Faraday rotator, polarization rotator, quarter-wave plate, and polarization-dependent beam-separator. According to some embodiments, such operations may be realized by at least one of, but not limited to, the configurations illustrated in FIGS. 4C, 5A, 5C, 6A, 6C, 10C, 11B, 12A, 13C, 15C, 16C, and 17B. According to some embodiments, the configurations for such operations may or may not be disposed with other optical components of an imaging optics system. For example, with reference to FIG. 22A, a polarization transformation configuration with optical path displacement comprises components 2241, 2242, 2251, 2252, and 2261 that are disposed with the optical components (lenses) of imaging optics system 2203.

In Step 2309, the transformed outgoing light is directed to one or more targets located at the field-of-view positions of the optical coherent imager that correspond to the chosen polarization-diversified free-space-to-waveguide couplers according to Step 2303. According to some embodiments, the transformed outgoing light may be directed to the targets with an additional imaging optics system disposed between the chosen couplers and the targets.

In Step 2311, the targets may reflect or scatter the transformed outgoing light that illuminates them. The reflected or scattered light from the targets may be received by the optical coherent imager at the field-of-view positions of the imager that correspond to the chosen polarization-diversified free-space-to-waveguide couplers described in Step 2309. According to some embodiments, the reflected or scattered light may be received with an additional imaging optics system disposed between the chosen couplers and the targets. According to some embodiments, the optical imaging system may be the same as the imaging optics system in Step 2309.

In Step 2313, the received light that is reflected or scattered from the target may be transformed by the same polarization transformation configuration as described in Step 2307. At each of the field-of-view positions of the imager described in Step 2311, the received light may comprise either one or both of a component with a third polarization that is the same as the second polarization of the transformed outgoing light, and a component with a fourth polarization that is orthogonal to the third polarization component. At each of the field-of-view positions, the polarization transformation configuration may transform the third polarization of the received light to a fifth polarization that is orthogonal to the first polarization of the outgoing light at that position. Similarly, the polarization transformation configuration may transform the fourth polarization of the received light to a sixth polarization that is orthogonal to the fifth polarization of the transformed received light. According to some embodiments, at each of the field-of-view positions, the optical path of at least one polarization component of the received light may additionally be displaced by the same optical-path-displacing components described in Step 2307. According to some embodiments, the polarization components of the received light that are displaced may be either one or both of the third and fourth polarizations.

In Step 2315, the transformed received light may be coupled from free space into in-coupling wave guides using one or more polarization-diversified free-space-to-wave guide couplers. According to some embodiments, these polarization-diversified free-space-to-waveguide couplers may be the same set of polarization-diversified free-free-space-to-waveguide couplers used to emit the outgoing polarized light in Step 2305. For each of the polarization-diversified free-space-to-waveguide couplers, at least one of the in-coupling waveguides receiving some or all of the transformed received light through the polarization-diversified free-space-to-waveguide coupler is different from the waveguide that guides the source light to the coupler (i.e., the out-coupling waveguide) according to Step 2303.

More specifically, on one hand, according to some embodiments, the polarization-diversified free-free-space-to-waveguide coupler may in-couple the fifth polarization of the transformed received light, which is orthogonal to the first polarization of the outgoing light emitted from the coupler, to at least one waveguide that is different from the out-coupling waveguide. This may be accomplished by the design of the polarization-diversified free-space-to-waveguide coupler that couples the fifth polarization of the transformed received light to an in-coupling waveguide that is different from the out-coupling waveguide. According to some embodiments, this may be accomplished by the optical path displacement of the third polarization of the received light, so that the fifth polarization of the transformed received light may arrive at the coupler at a spatial location that is different from the spatial location where the outgoing light is emitted from the coupler.

On the other hand, according to some embodiments, the polarization-diversified free-space-to-waveguide coupler may in-couple the sixth polarization of the transformed received light, which is orthogonal to the fifth polarization of the transformed received light, to at least one waveguide that is different from the out-coupling waveguide. This may be accomplished by the optical path displacement of the fourth polarization of the received light, so that the sixth polarization of the transformed received light may arrive at the coupler at a spatial location that is different from the spatial location where the outgoing light is emitted from the coupler. According to some embodiments, the optical path displacements of the third and fourth polarizations of the received light may be realized through the same optical-path-displacement components described in Step 2313.

In Step 2317, the in-coupled received light in the in-coupling waveguides may be detected by detectors that are disposed in proximity to the polarization-diversified free-space-to-waveguide couplers that in-couple the transformed received light. The detectors may be arranged as heterodyne detection setups to carry out heterodyne detection with local oscillator light that is supplied to the heterodyne detection setups.

In Step 2319, the detected signals may be processed to extract information about the target. The processing of signals may be performed by a signal processing unit that may or may not be a part of the optical coherent imager. According to some embodiments, the information of the target may include but not limited to the coordinates of the target and the reflectivity of the target surface. According to some embodiments, the information of the target may include the distance of the target from the optical coherent imager. According to some embodiments, the information of the target may include the velocity information of the target. According to some embodiments, the distance and velocity information may be obtained by modulating the source light in Step 2301 according to the approach of FMCW LIDAR and be extracted by means of Fourier transformations of the detected signals.

For the purposes of describing and defining the present disclosure, it is noted that terms of degree (e.g., "substantially," "slightly," "about," "comparable," etc.) may be utilized herein to represent the inherent degree of uncertainty that may be attributed to any quantitative comparison, value, measurement, or other representation. Such terms of degree may also be utilized herein to represent the degree by which a quantitative representation may vary from a stated reference (e.g., about 10% or less) without resulting in a change in the basic function of the subject matter at issue. Unless otherwise stated herein, any numerical value appearing in the present disclosure are deemed modified by a term of degree (e.g., "about"), thereby reflecting its intrinsic uncertainty.

Although various embodiments of the present disclosure have been described in detailed herein, one of ordinary skill in the art would readily appreciate modifications and other embodiments without departing from the spirit and scope of the present disclosure as stated in the appended claims.

What is claimed is:

1. An optical coherent sensor comprising a photonic substrate, a plurality of coherent sensing units disposed on the photonic substrate, and a polarization transformer disposed on the coherent sensing units, wherein each of the coherent sensing units comprises:
   a polarization diversified optical coupler disposed on a substrate surface of the photonic substrate to direct optical signals having a first polarization state to and from free space and a first waveguide disposed on the substrate surface and to direct optical signals having a second polarization state to and from free space and a second waveguide disposed on the substrate surface, the first polarization state being orthogonal to the second polarization state; and
   one or more photodetectors disposed on the substrate surface and optically coupled to the polarization diversified optical coupler;
   wherein said optical signals having the first polarization state propagate along a first direction of an optical path after exiting the polarization transformer; and
   wherein said optical signals having the second polarization state propagate along a second direction of the same optical path before entering the polarization transformer, the second direction being opposite to the first direction.

2. The optical coherent sensor of claim 1, wherein the polarization diversified optical coupler comprises a first sub-coupler and a second sub-coupler.

3. The optical coherent sensor of claim 2, wherein one of the first and second sub-couplers is polarization dependent which optimally couples with optical signals of a predefined polarization state, and wherein the other one of the first and second sub-couplers is polarization independent which optimally couples with optical signals of any polarization states.

4. The optical coherent sensor of claim 2, wherein the second sub-coupler is disposed on and vertically separated from the first sub-coupler.

5. The optical coherent sensor of claim 2, wherein the first and second sub-couplers are disposed on the substrate surface of the photonic substrate and laterally separated from each other.

6. The optical coherent sensor of claim 5, wherein the polarization transformer directs an outgoing optical signal from one of the first and second sub-couplers to an optical path in free space, and separates an incoming optical signal from the optical path into optical signals having a third polarization state and optical signals having a fourth polarization state, at least one of said optical signals having the third polarization state and said optical signals having the fourth polarization state being spatially displaced by the polarization transformer such that said optical signals having the third and fourth polarization states are incident respectively on the first and second sub-couplers.

7. The optical coherent sensor of claim 2, wherein the polarization transformer comprises at least one polarization-dependent beam-separator.

8. The optical coherent sensor of claim 2, wherein the polarization diversified optical coupler further comprises a third sub-coupler.

9. The optical coherent sensor of claim 8, wherein the first, second, and third sub-couplers are disposed on the substrate surface of the photonic substrate and laterally separated from each other.

10. The optical coherent sensor of claim 8, wherein the polarization transformer directs an outgoing optical signal from one of the first, second, and third sub-couplers to an optical path in free space, and separates an incoming optical signal from the optical path into optical signals having a third polarization state and optical signals having a fourth polarization state, at least one of said optical signals having the third polarization state and said optical signals having the fourth polarization state being spatially displaced by the polarization transformer such that said optical signals having the third and fourth polarization states are incident respectively on two of the first, second, and third sub-couplers.

11. The optical coherent sensor of claim 8, wherein the polarization diversified optical coupler further comprises a fourth sub-coupler.

12. The optical coherent sensor of claim 11, wherein the polarization transformer directs an outgoing optical signal from two of the first, second, third, and fourth sub-couplers to an optical path in free space, and separates an incoming optical signal from the optical path into optical signals having a third polarization state and optical signals having a fourth polarization state, at least one of said optical signals having the third polarization state and said optical signals having the fourth polarization state being spatially displaced by the polarization transformer such that said optical signals having the third and fourth polarization states are incident respectively on two of the first, second, third, and fourth sub-couplers.

13. The optical coherent sensor of claim 1, wherein the polarization transformer comprises one or more polarization converters that rotate a linearly polarized optical signal by a predefined angle.

14. The optical coherent sensor of claim 13, wherein at least one of the one or more polarization converters is a Faraday rotator.

15. The optical coherent sensor of claim 1, wherein the polarization transformer comprises one or more quarter-wave plates.

16. The optical coherent sensor of claim 1, wherein each of the coherent sensing units further comprises:
one or more 2×2 optical couplers disposed on the substrate surface and optically coupled to the polarization diversified optical coupler through at least one of the first and second waveguides; wherein said one or more photodetectors are optically coupled to the polarization diversified optical coupler through the one or more 2×2 optical couplers.

17. An optical coherent imager comprising the optical coherent sensor of claim 1 and an imaging optics system including a plurality of lenses, wherein the imaging optics system is disposed such that the optical coherent sensor is located proximate an image plane of the imaging optics system.

18. An apparatus comprising an imaging optics system, a coherent sensor, and a polarization transformer on the coherent sensor, wherein the coherent sensor comprises:
a photonic substrate;
a polarization diversified optical coupler disposed on a substrate surface of the photonic substrate to direct optical signals having a first polarization state to and from free space and a first waveguide disposed on the substrate surface and to direct optical signals having a second polarization state to and from free space and a second waveguide disposed on the substrate surface, the first polarization state being orthogonal to the second polarization state; and
one or more photodetectors disposed on the substrate surface and optically coupled to the polarization diversified optical coupler through at least one of the first and second waveguides;
wherein said optical signals having the first polarization state propagate along a first direction of an optical path after exiting the polarization transformer and before entering the imaging optics system; and
wherein said optical signals having the second polarization state propagate along a second direction of the same optical path after exiting the imaging optics system and before entering the polarization transformer, the second direction being opposite to the first direction.

19. The apparatus of claim 18, wherein the optical path corresponds to a field of view position of the imaging optics system.

20. A method for optical coherent imaging, comprising:
emitting, from an optical coherent imager having a photonic substrate with a plurality of coherent detection units disposed on the photonic substrate, one or more outgoing optical signals to one or more targets respectively along one or more optical paths in free space corresponding respectively to one or more field-of-view positions of the optical coherent imager, wherein different coherent detection units correspond to different field of view positions;
receiving, by the optical coherent imager along the one or more optical paths, one or more incoming optical signals reflected from the targets illuminated by the one or more outgoing optical signals;
converting, by a polarization transformer of the optical coherent imager, each of the one or more incoming optical signals into a first optical component having a first polarization state and a second optical component having a second polarization state, wherein the first polarization state is orthogonal to the second polarization state; and
guiding, by one or more polarization diversified optical couplers disposed on the photonic substrate of the optical coherent imager, the first and second optical components of the one or more incoming optical signals to one or more photodetectors disposed on the photonic substrate of the optical coherent imager so as to perform heterodyne detection at each of the one or more field-of-view positions of the optical coherent imager, thereby determining information of the targets at the one or more field-of-view positions;
wherein one of the one or more outgoing optical signals corresponding to a first one of the one or more field-of-view positions of the optical coherent imager propagates along a same one of the one or more optical paths as that of one of the one or more incoming optical signals corresponding to said first one of the one or more field-of-view positions of the optical coherent imager.

21. The method of claim 20, wherein emitting the one or more outgoing optical signals comprises:
generating one or more source optical signals from a light source;
converting the one or more source optical signals into the one or more outgoing optical signals, wherein each of the one or more outgoing optical signal has a first emission polarization state, by the one or more polarization diversified optical couplers; and
emitting the one or more outgoing optical signals from the one or more polarization diversified optical couplers.

22. The method of claim 21, after emitting the one or more outgoing optical signals from the one or more polarization diversified optical couplers, further comprising transforming each of the one or more outgoing optical signals from the first emission polarization state to a second emission polarization state by the polarization transformer of the optical coherent imager.

23. The method of claim 20, wherein converting the one or more incoming optical signals comprises rotating the first polarization state of each of the one or more incoming optical signals by a first predefined polarization angle and the second polarization state of each of the one or more incoming optical signals by a second predefined polarization angle.

24. The method of claim 20, wherein converting the one or more incoming optical signals comprises spatially displacing at least one of the first and second optical components of each of the one or more incoming optical signals in accordance with the first and second polarization states such that the first and second optical components are incident respectively on first and second sub-couplers of each of the one or more polarization diversified optical couplers.

\* \* \* \* \*